(12) United States Patent
Huang et al.

(10) Patent No.: US 8,530,465 B2
(45) Date of Patent: *Sep. 10, 2013

(54) 1, 2-DISUBSTITUTED AMIDO-ANTHRAQUINONE DERIVATIVES, PREPARATION METHOD AND APPLICATION THEREOF

(75) Inventors: Hsu-Shan Huang, Taipei (TW); Chia-Chung Lee, Taipei (TW)

(73) Assignee: National Defense Medical Center, Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 13/564,002

(22) Filed: Aug. 1, 2012

(65) Prior Publication Data

US 2013/0059862 A1    Mar. 7, 2013

Related U.S. Application Data

(62) Division of application No. 12/712,644, filed on Feb. 25, 2010, now Pat. No. 8,304,415.

(51) Int. Cl.
| | |
|---|---|
| *A61K 31/495* | (2006.01) |
| *A61K 31/496* | (2006.01) |
| *A61K 31/167* | (2006.01) |
| *A61K 31/54* | (2006.01) |
| *A61K 31/5375* | (2006.01) |
| *C07D 295/15* | (2006.01) |
| *C07D 213/56* | (2006.01) |
| *C07D 261/18* | (2006.01) |
| *C07D 401/04* | (2006.01) |
| *C07D 491/113* | (2006.01) |
| *C09B 1/16* | (2006.01) |

(52) U.S. Cl.
USPC ............. 514/227.5; 514/237.8; 514/252.14; 514/253.01; 514/278; 514/325; 514/378; 514/428; 514/448; 514/471; 514/467; 514/617; 544/59; 544/156; 544/295; 544/360; 544/380; 546/19; 546/204; 546/285; 548/248; 548/528; 549/72; 549/452; 549/483; 552/237

(58) Field of Classification Search
None
See application file for complete search history.

(56) References Cited

U.S. PATENT DOCUMENTS

| | | | |
|---|---|---|---|
| 4,197,249 | A | 4/1980 | Murdock et al. |
| 4,692,447 | A | 9/1987 | Cignarella et al. |
| 5,436,243 | A | 7/1995 | Sachs et al. |
| 6,777,564 | B2 | 8/2004 | Lee et al. |
| 8,304,415 | B2 * | 11/2012 | Huang et al. ............ 514/252.12 |
| 2005/0009924 | A1 | 1/2005 | Huang |

* cited by examiner

*Primary Examiner* — Emily Bernhardt
(74) *Attorney, Agent, or Firm* — Muncy, Geissler, Olds & Lowe, PLLC

(57) ABSTRACT

The invention provides a series of novel 1,2-disubstituted amido-anthraquinone derivatives. Further, the invention also provides the preparation method and application of said derivatives, said application comprises: said derivatives with therapeutically effective amount are prepared into pharmaceutical compositions for inhibition of cancer cell growth, further treating cancer.

3 Claims, 13 Drawing Sheets

US 8,530,465 B2

1, 2-DISUBSTITUTED AMIDO-ANTHRAQUINONE DERIVATIVES, PREPARATION METHOD AND APPLICATION THEREOF

CROSS REFERENCE TO RELATED APPLICATIONS

This application is a Divisional of application Ser. No. 12/712,644, filed on 25 Feb. 2010, and for which priority is claimed under 35 U.S.C. §120; the entire contents of which are hereby incorporated by reference.

BACKGROUND OF THE INVENTION

1. Field of the Invention

The invention relates to development of cancer drug, especially relates to the development of novel 1,2-disubstituted amido-anthraquinone derivatives, preparation method and application thereof.

2. Description of the Prior Art

Telomere

A telomere is a region of repetitive DNA at the end of a chromosome, which protects the end of the chromosome from deterioration, recombination, and end-to-end fusion. Telomere is composed of short and repeated DNA sequences. A high percentage of guanine (G) is present in this DNA sequence from 5'-end to 3'-end. The telomere DNA sequence (TTAGGG)n is conserved among vertebrates, including human.

In normal somatic cell, the terminal end of the chromosome will lose a part of RNA primer after each replication, and will shorten off about 50-60 bp after each cell division. When the telomere is shortened to a certain extent, cell will go to apoptosis, this phenomenon is called an end-replication problem of a cell.

Telomerase

Telomerase is the enzyme that synthesizes telomeric DNA, the terminal DNA at chromosome ends which, together with telomere-binding proteins, confers stability to chromosomes. In most of organism, the replication and maintenance of the length of telomere has to rely on telomerase. The telomerase is composed of RNA and protein subunits. At present, part of important telomerase subunits had been identified. The composition of human telomerase comprising: human telomerase reverse transcriptase (hTERT) having reverse transcriptase activity, human telomerase RNA component used as a template, and some telomere-binding proteins such as human telomerase-associated protein, p23, hsp90, hsp40, hsp70 and the like.

Many research studies had indicated that the activity of human telomerase can only be detected in cells having high proliferation ability, for example, germ cells, hemopoietic cells, part of stem cells, most of immortalized cells and most of tumor cells. In the somatic cell, the telomere will be shorten gradually as the number of cell division increased, which may be considered as the mitotic clock for counting the number of cell division. When a telomere is shortened to a certain extent, cell will stop division and entering aging stage, stay at this stage for a period of time, and then goes to death. This period of time is called mortality stage 1 (M1 stage). When a tumor suppressor gene such as p53 or Rb is mutated within M1 stage, the cell might escape from aging stage and keeps on cell division in this period of time which is called mortality stage 2 (M2 stage). If a cell lacks of telomerase activity during this period, the length of a telomere will be reduced still, the telomere will not be able to protect the terminal end of the chromosome, and this might result into the instability of the chromosome, as well as the cell can not transfer genetic information completely and enters apoptosis in the end. Therefore, M2 stage is also called a crisis stage. Most of cells will die in M2 stage, except small part of cells with telomerase activity will be survived. This small part of cells will continue to divide without limitation and become an immortalized cell (or a cancer cell).

In view of the foregoing, it is thought generally that the activation of telomerase can maintain the length of a telomere so as to prevent a cell from entering the ageing stage; or the inhibition of telomerase activity can be used to limit the division of a cancer cell. Both thought may become the key factors in the development of a cell toward immortalization or cancerization. In summary, using the telomerase inhibitors to treat the cancer have been considered as a novel cancer-specific therapy, as most tumor cells have high expression of telomerase, whereas most normal somatic cells express low or undetectable levels of telomerase and is therefore an attractive target for the design of anticancer agents.

Anthraquinone-containing extracts from different plant sources such as senna, cascara, aloe, frangula, and rhubarb have been found to have wide variety of pharmacological activities such as anti-inflammatory, wound healing, analgesic, antipyretic, antimicrobial, and antitumor activities. And some of the anthraquinone derivatives had also shown the antitumor activity. Therefore, many investigators consider them as highly promising lead candidates in drug design.

In view of the importance of the development of cancer therapy drugs, the invention provides the inventive 1,2-disubstituted amido-anthraquinone derivatives, preparation method and application thereof.

SUMMARY OF THE INVENTION

One object of the invention is to provide a series of novel 1,2-disubstituted amido-anthraquinone derivatives, said 1,2-disubstituted amido-anthraquinone derivatives represented by formula I, wherein $R_a$ and $R_b$ are as defined herein.

Another object of the invention is to provide a method for preparing novel 1,2-disubstituted amido-anthraquinone derivatives represented by formula I, wherein $R_a$ and $R_b$ are as defined herein.

In addition, another object of the invention is to provide a pharmaceutical composition containing said novel 1,2-disubstituted amido-anthraquinone derivatives as represented by formula I (wherein $R_a$, and $R_b$ are as defined herein), said pharmaceutical composition is used to treat cancer.

In order to achieve the above-described objects of the invention, the inventor used commercial 1,2-diaminoanthraquinone as the reaction starting materials to carry out modification on various functional groups through chemical synthetic reaction, so as to produce a series of novel 1,2-disubstituted amido-anthraquinone derivatives, namely, compounds CC-01 to CC-50.

In addition, the invention investigates and evaluate in following examples whether the derivatives of the invention serve as a target drug or a chemotherapy drug, so as to provide inhibition effect on the growth of tumor cell or cancer cell, and further treat cancer.

These features and advantages of the present invention will be fully understood and appreciated from the following detailed description of the accompanying Drawings.

DETAILED DESCRIPTION OF THE PREFERRED EMBODIMENT

Figure 1:
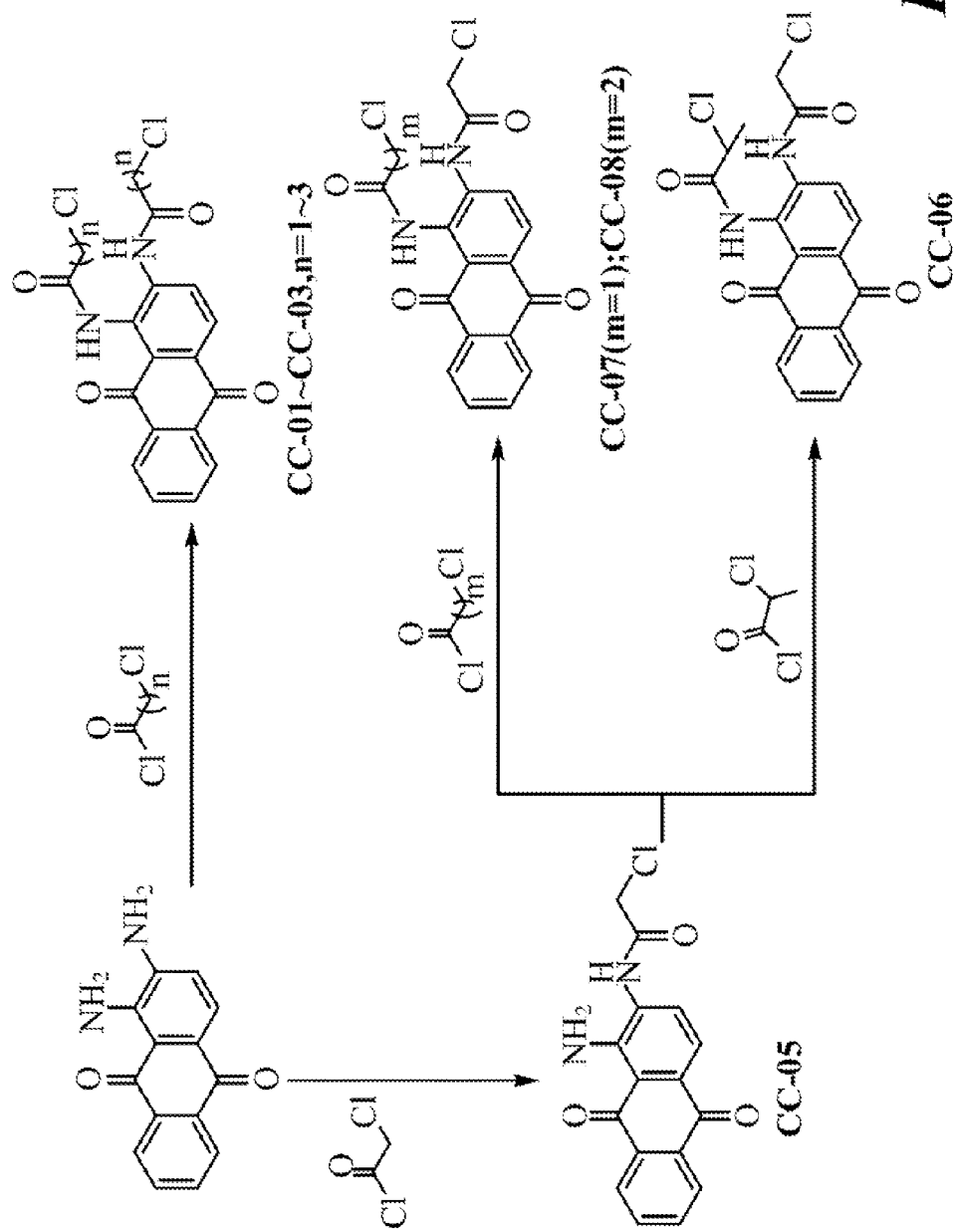
FIG. 1 depicts the preparation process of compound CC-01 to CC-03, CC-05 to CC-08.

The invention provides a series of novel 1,2-disubstituted amido-anthraquinone derivatives, preparation methods and applications thereof, wherein said application comprises: said derivatives with therapeutically effective amount are prepared into pharmaceutical compositions for treating cancer; wherein said pharmaceutical composition comprises at least one selected from the group consisting of therapeutically effective amount of compounds represented by general formula I and a pharmaceutically acceptable excipient, wherein $R_a$ and $R_b$ are as defined herein:

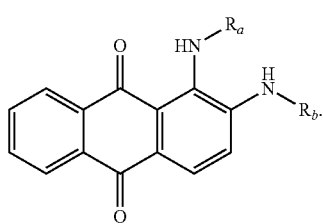

formula I

Said pharmaceutical composition with therapeutically elective amount is used to treat cancer and inhibit the growth of cancer cell, wherein said cancer include, but are not limited to, leukemia, non-small cell lung cancer, colon cancer, cns cancer, melanoma, ovarian cancer, renal cancer, prostate cancer, breast cancer.

The excipient that can be used in the invention comprises, but is not limited to, diluent, filler, binder, disintegrating agent, lubricant and the like. Further, said excipient include, but not limited to microcrystalline cellulose, polyvinylpyrrolidone (PVP), corn starch, modified starches, sodium carboxymethylstarch, resin, gelatinized starches, sugars, polyethylene glycol (PEG), polyvinyl alcohol, hydroxypropyl cellulose, methyl cellulose, hydroxymethyl cellulose, hydroxypropyl methyl cellulose and the like.

The term "therapeutically effective amount" or "pharmaceutically effective dosage" refers to the amount of a compound or a combination of compounds used to treat disease (such as cancer), to improve, attenuate or eliminate one or more symptoms of a particular disease (such as cancer), or to inhibit or delay the outbreak of one or more symptoms caused by growth or proliferation of cancer cells.

The term "pharmaceutically acceptable" is intended to mean that a substance or a combination has to be compatible with other components in the same formulation, and also has to be not harmful or cause no other side effect to a patient.

The invention will be illustrated with the examples as follows, without the intention that the invention is limited thereto. The substance or material herein are easily obtained, the source of material is not limited to following examples.

Example 1

Source of Material

From Merck:
TLC 60 $F_{254}$, methanol, dichloromethane, Chloroform-$d_1$, Dimethyl sulfoxide-$d_6$ 99.8%, DMSO-$d_6$.

From Aldrich:
1,2-diaminoanthraquinone, N,N-Diisopropylethylamine (DIPEA), triethylamine (TEA), pyridine, N,N-dimethylformamide anhdrous 99.8% (DMF), tetrahydrofuran anhdrous 99.9% (THF), chloroacetyl chloride, 3-chloropropionyl chloride, 4-chlorobutyryl chloride, 2-chloropropionyl chloride, 5-chlorovaleroyl chloride, benzoyl chloride, 4-toluoyl chloride, 3-toluoyl chloride, 2-toluoyl chloride, 4-fluorobenzoyl chloride, 3-fluorobenzoyl chloride, 2-fluorobenzoyl chloride, 4-chlorobenzoyl chloride, 3-chlorobenzoyl chloride, 2-chlorobenzoyl chloride, 4-(trifluoromethyl)benzoyl chloride, 3-(trifluoromethyl)benzoyl chloride, 2-(trifluoromethyl)benzoyl chloride, 2,5-(trifluoromethyl)benzoyl chloride, phenylacetyl chloride, cyclopropane carbonyl chloride, cyclohexanecarbonyl chloride, 2-furoyl chloride, 2-thiophenecarbonyl chloride, isoxazole-5-carbonyl chloride, 2,5-dimethylfuran-3-carbonyl chloride, phenoxyacetyl chloride, (phenylthio)acetyl chloride, N-phenylpiperazine, 1-(2-fluorophenyl)piperazine, dimethylamine, 2-methylaminomethyl-1,3-dioxolane, 2-(2-methylaminoethyl pyridine), piperidine, 1,4-dioxa-8-azaspiro[4.5]decane, morpholine, thiomorpholine, N-methylpiperazine, 2-(piperazin-1-yl)ethanol, 1-(2-cyanophenyl)piperazine, 1-(2-methoxyphenyl)piperazine, 1-(2-pyridyl)piperazine, 1-(2-pyrimidyl)piperazine.

From Mallinckrodt (J. T. Baker):
Ethyl acetate, n-Hexane, N,N-dimethyl acetamide, Ether, Sodium sulfate anhydrous ($Na_2SO_4$), Magnesium sulfate ($MgSO_4$)

Example 2

Chemical Synthesis

Scheme I, Referring to FIG. 1:
1. General Procedure A 1,2-diaminoanthraquinone was dissolved in DMF, added thereto successively with pyridine and a series of acyl chlorides under stirring. After completion of reaction, the mixed solution was cooled down, filtered to obtain precipitate and finally, the precipitate was washed with ethanol, then compounds CC-01 to CC-03 can be obtained.

2. General Procedure B 1,2-diaminoanthraquinone was dissolved in DMF, and added thereto with chloroacetyl chloride under stirring. After completion of reaction, the mixed solution was cooled down, filtered to obtain precipitate, and finally, the precipitate was washed with ethanol, then compounds CC-05 can be obtained.

3. General Procedure C

Compound CC-05 was dissolved in DMF, and added thereto successively with (1) pyridine and 2-chloropropionyl chloride, (2) pyridine and 3-chloropropionyl chloride, or (3) pyridine and 4-chlorobutyryl chloride under stirring. After completion of reaction, the well mixed solution was cooled down, filtered to obtain precipitate, and finally, the precipitate was washed with ethanol and recrystallized, then the compounds CC-06, CC-07 and CC-08 can be obtained, respectively.

Figure 2:
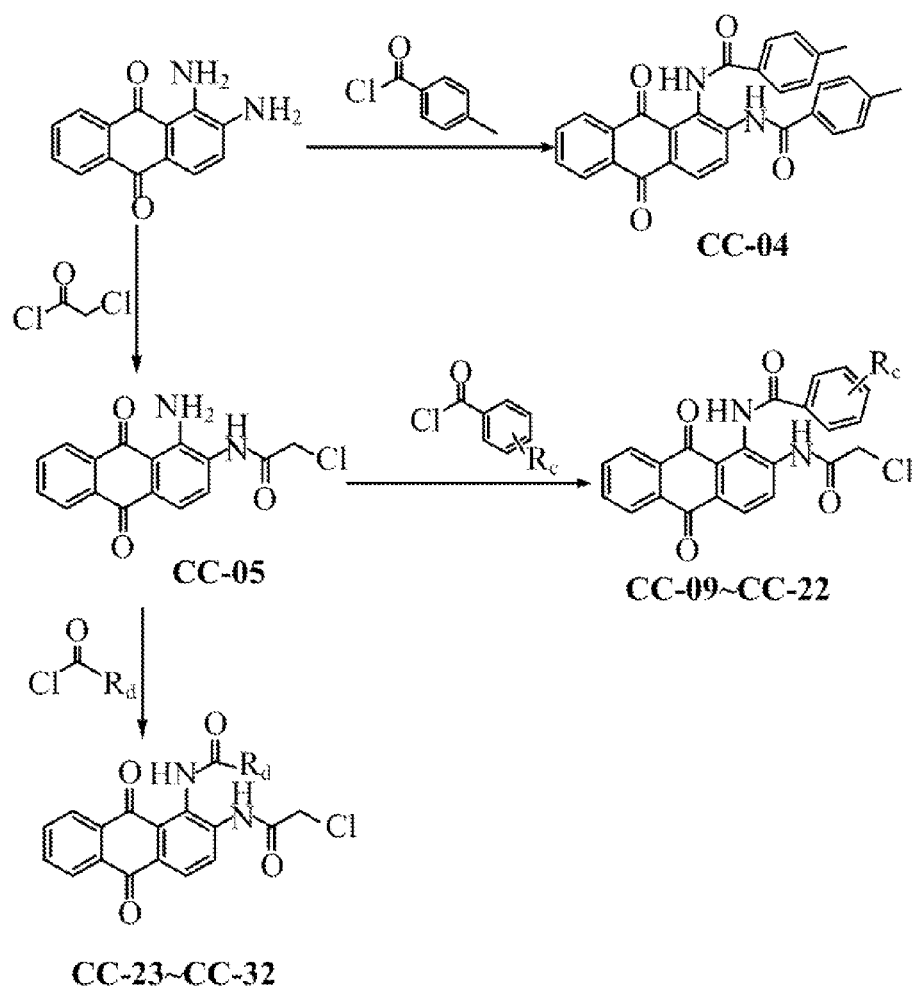
FIG. 2 depicts the preparation process of compound CC-04, CC-09 to CC-22, CC-23 to CC-32.

Scheme II, Referring to FIG. 2:

1. General Procedure A 1,2-diaminoanthraquinone was dissolved in THF, to the solution added successively with pyridine and 4-toluoyl chloride under stirring. The resultant residue was heated by stirring in a oil bath at temperature of 120-130° C. After completion of the reaction, the mixture was filtered and the filtrate was concentrated by reduced pressure concentrator (such as Vacuum Evaporator). The mixture was extracted with ethyl acetate, dried with $MgSO_4$, and concentrated under reduced pressure. The crude product was washed with ethyl acetate/n-hexane, and finally, crystallized in ethanol to obtain compound CC-04.

2. General Procedure B

Compound CC-05 was dissolved in THF, and to the solution was added successively with pyridine and a series of benzoyl chloride under stirring. The mixture was then heated by stirring in a oil bath at temperature of 120-130° C. After completion of the reaction, the mixture was filtered and the filtrate was concentrated by reduced pressure concentrator (such as Vacuum Evaporator). The residue was then extracted with ethyl acetate, dried on $MgSO_4$, and then concentrated under reduced pressure. The crude product was washed with ethyl acetate/n-hexane and finally, recrystallized in ethanol to obtain compounds CC-09 to CC-22.

3. General Procedure C

Compound CC-05 was dissolved in THF, and to the solution was added successively with pyridine and a series of acetyl chloride under stirring. The mixture was stirred in an oil bath at temperature of 120-130° C. After completion of reaction, the mixture was filtered and the filtrate was concentrated by reduced pressure concentrator (such as Vacuum Evaporator). The residue was extracted with ethyl acetate, dried on $MgSO_4$, and concentrated under reduced pressure. The crude product was washed with ethyl acetate/n-hexane, and finally, the crude product was recrystallized in ethanol to obtain compounds CC-23 to CC-32.

Figure 3:
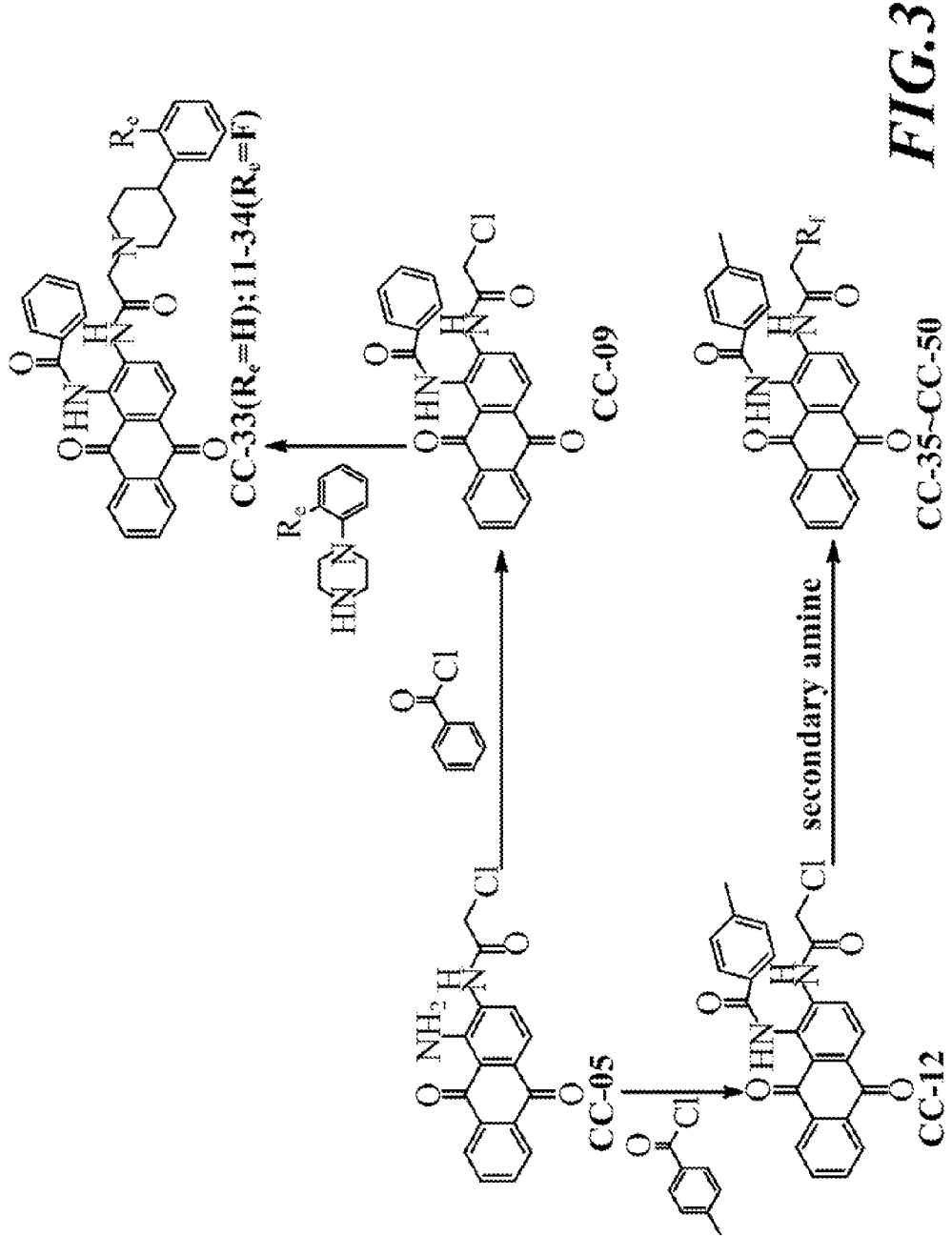
FIG. 3 depicts the preparation process of compound CC-12, CC-33, CC-34, CC-35 to CC-50.

Scheme III, Referring to FIG. 3:

1. General Procedure A

Compound CC-09 was dissolved in THF, and to the solution was added successively with N,N-diisopropyl ethylamine (DIPEA) and a series of piperazine under stirring. This mixture was heated under reflux. After completion of reaction, the mixture was filtered and the crude product was isolated from the upper layer of the filtrate and recrystallized in ethanol to obtain compounds CC-33 and CC-34.

2. General Procedure B

Compound CC-12 was dissolved in THF, and to the solution was added successively with N,N-diisopropyl ethylamine (DIPEA) and a series of secondary amines under stirring. This mixture was heated under reflux. After completion of reaction, the mixture was filtered and the filtrate was concentrated by reduced pressure concentrator (such as Vacuum Evaporator). The residue was extracted with ethyl acetate, dried on $MgSO_4$, and concentrated under reduced pressure. The crude product was washed with ethyl acetate/n-hexane, and finally, the crude product was recrystallized in ethanol to obtain compounds CC-35 to CC-50.

Example 3

Telomerase Activity Assays

Compounds CC-01 to CC-50 (total 50 compounds) chemically synthesized above were subjected to following three sections of telomerase activity assays: 3-1. Telomere repeat amplification protocol (TRAP) assays; 3-2. Secreted alkaline phosphatase assay (SEAP assay) and MTT assay, to assay the cell survival rate of cancer cell; 3-3. The United State National Cancer Institute (NCI) had selected 5 compounds from the invention, which were subjected to cell toxicity assay against 55 to 60 kinds of cancer cell lines.

3-1. Telomere Repeat Amplification Protocol (TRAP) Assay:

Telomerase activity was detected by a modified version of the general TRAP protocol. Telomerase products were resolved by 10% polyacrylamide gel electrophoresis and visualized by staining with SYBER Green. As a source of telomerase, the total cell lysates derived from lung cancer cell line H1299 cells were used. Protein concentration of the lysates was assayed using Bio-Rad protein assay kit using BSA standards.

3-2. SEAP Assay and MTT Assay 3-2-1. SEAP Assay

Cell Culture and Assessment of hTERT:

H1299 is a non-small-cell lung cancer cell strain and possesses telomerase activity, therefore, is suitable to be used as a model cell strain for screen telomerase inhibitor. H1299 were grown in RPMI 1640 media supplemented with 10% fetal bovine serum, 100 units/mL penicillin and 100 mg/mL streptomycin in a humidified atmosphere with 5% $CO_2$ at 37° C. Culture media were changed every three days. To establish stable cell lines that the expression of hTERT could be monitored by a reporter system, a about 3.3 kbp DNA fragment ranging from −3338 to +1 bp of the hTERT gene (hTERT promoter, $P_{hTERT}$) was subcloned upstream to a secreted alkaline phosphatase gene (SEAP) and transfected into H1299 by electroporation. The stable clones were selected using G418. The stable clones derived from H1299 were cultured using conditions that are similar to their parental cells.

SEAP Assay:

Secreted alkaline phosphatase was used as the reporter system to monitor the transcriptional activity of hTERT. Here, about $10^4$ cells each were grown in 96-well plates and incubated at 37° C. for 24 hours and changed with fresh media. Varying amounts of drugs were added and cells were incubated for another 24 hours. Culture media were collected and heated at 65° C. for 10 min to inactivate heat-labile phosphatases. An equal amount of SEAP buffer (2 M diethanolamine, 1 mM $MgCl_2$, and 20 mM $_L$-homoarginine) was added to the media and p-nitrophenyl phosphate was added to a final concentration of 12 mM. Absorptions at 405 nm were taken, and the rate of absorption increase is determined (the increasing rate of absorbance at 405 nm was used to represent the activity of SEAP).

Further, cells were subjected to MTT assay to compare the relative toxicity or effect of each compound on cell proliferation and activity.

3-2-2. MTT Assay

MTT assay is a method often used to determine cell survival rate or proliferation, which is described briefly as followed:

The above-described cells are cultured in a 96-well plate, to which was added with 25 μl MTT solution, and cultured in a 37° C. carbon dioxide incubator for 4 hours. Then, 100 μl Lysis buffer is added and incubated in a 37° C. carbon dioxide incubator overnight. An ELISA reader (Bio-Rad Model 450) is used to read optical density (O.D.) at 550 nm.

3-3. The National Cancer Institute (NCI)'s Anticancer Drug Screen

In brief, cellular protein levels were determined after 48 hours of drug exposure by sulforhodamine B colorimetry. Through the use of a time 0 cell control, the cell growth can be determined for each cell line thus allowing calculations of the 50% growth inhibitory concentration ($GI_{50}$), the total growth inhibition (TGI), and the 50% lethal concentration ($LC_{50}$). Comparison to plates not exposed to drug permits determination of concentration and times of exposure conferring 50% net growth inhibition ($GI_{50}$), TGI, and 50% cell kill ($LC_{50}$). These data are then plotted as mean bar graphs and as dose-response curves.

Figure 4:
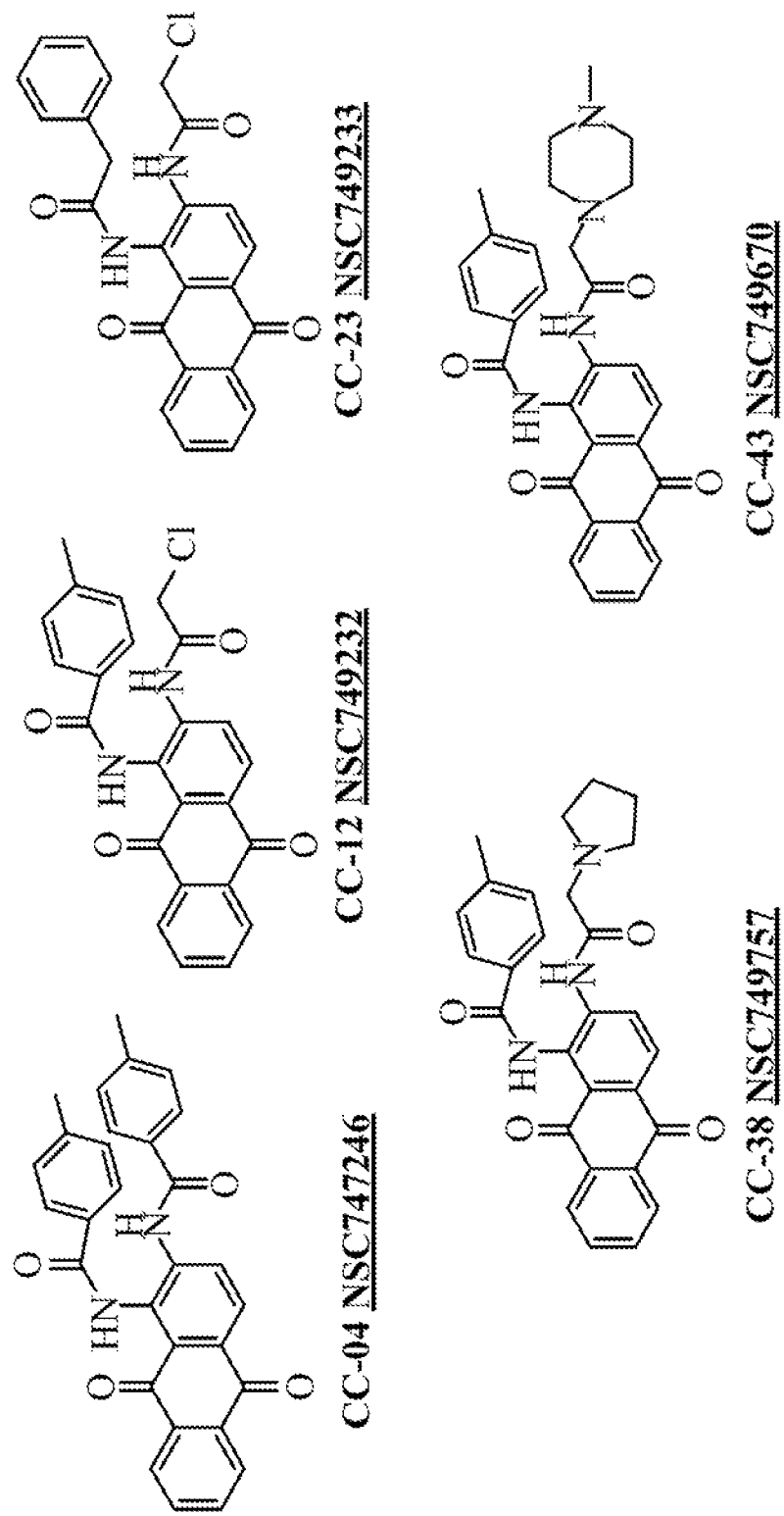
FIG. 4 depicts the compounds were selected by National Cancer Institute (NCI) for NCI Developmental Therapeutics Program (DTP) in-vitro screen of 60 human derived cancer cell lines.

From the data analysis it follows that approximately 95% of the actives (potent anticancer drugs) from the 60 cell line screen can be identified. By these criteria, five compounds (each with its certification number, refer to FIG. 4) of the invention were reported that having anticancer activity.

Synthesis and Analysis of Each Compound:

The chemical synthetic procedure of 1,2-disubstituted amidoanthraquinone derivatives described in Example 2 was disclosed further in following examples.

Testing Instruments:

Melting point determination was carried out on a Büchi 545 melting point tester. IR (Kbr) was recorded on a Perkin-Elmer 983G spectrometer. MS was determined in National Chiao Tung University Instrument Center. $^1$H-NMR and $^{13}$C-NMR were recoded on Varian GEMINI-300 (300 MHz) or BRUKER AV 500 MHz.

Example 4

1,2-bis-(chloroacetamido)-anthraquinone (CC-01)

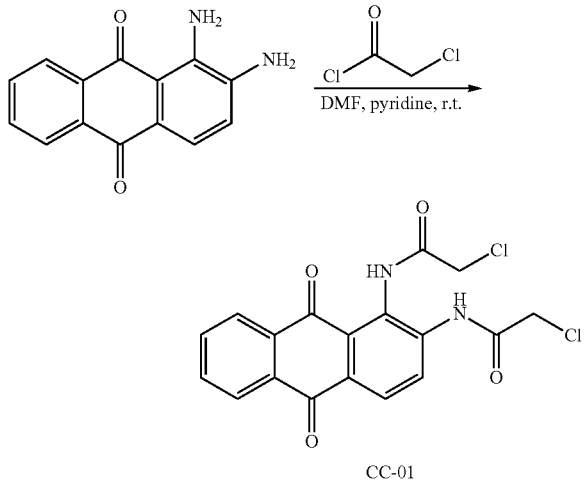

CC-01

1,2-diaminoanthraquinone (0.92 g, 4 mmole) was dissolved in anhydrous N, N-dimethylformamide (30 ml). Nitrogen was insufflated in the reaction flask at room temperature. To the solution, was added successively with pyridine (0.5 ml), and chloroacetyl chloride (1 ml, 1.2 mmole). The mixture was stirred at room temperature for 24 hours. After completion of reaction, the mixture was put in an ice-water bath (200 ml), and stood still for 10 to 20 minutes to allow precipitation. The precipitate was filtered and washed with ethanol to obtain a yellowish brown compound CC-01. Mol. Wt.: 391.2049 ($C_{18}H_{12}Cl_2N_2O_4$); $R_f$: 0.27 (ethyl acetate:n-hexane=1:2); Yield: 56%; Mp.: 254-255° C. (EtOH); HRMS (EI) m/z: calcd [M]$^+$, 390.0174 ($C_{18}H_{12}Cl_2N_2O_4^+$). Found, 390.0170. $^1$H-NMR (300 MHz, DMSO-$d_6$) δ (ppm): 4.43 (s, 2H, —CH$_2$Cl), 4.45 (s, 2H, —CH$_2$Cl), 7.90-7.93 (m, 2H, Ar—H), 8.12-8.18 (m, 2H, Ar—H), 8.22 (d, J=8.1 Hz, 1H, Ar—H), 8.38 (d, J=9.0 Hz, 1H, Ar—H), 9.83 (s, 1H, Ar—NH—), 10.29 (s, 1H, Ar—NH—); $^{13}$C-NMR (75 MHz, DMSO-$d_6$) δ (ppm): 43.25, 126.20, 126.93, 128.14, 130.33, 132.28, 134.25, 134.42, 134.63, 139.77, 165.61 (NCO), 166.02 (NCO), 181.60 (CO), 183.25 (CO).

Example 5

1,2-bis-(3-chloropropionamido)-anthraquinone (CC-02)

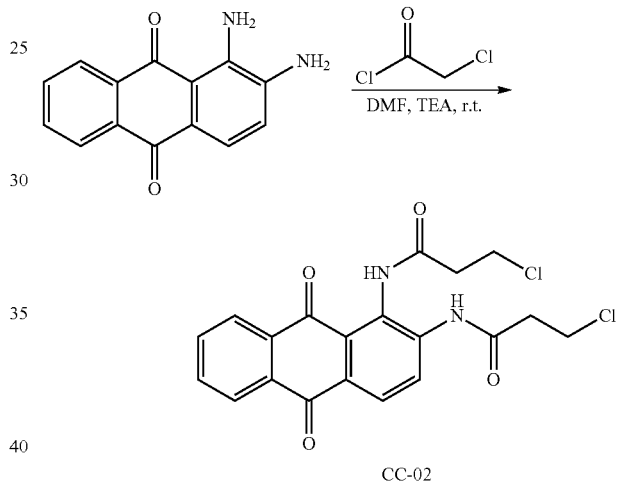

CC-02

1,2-diaminoanthraquinone (0.92 g, 4 mmole) was dissolved in anhydrous N, N-dimethylformamide (30 ml). Nitrogen was insufflated in the reaction flask at room temperature. To the solution, was added successively with triethylamine (TEA) (0.5 ml), and 3-chloropropionyl chloride (1.2 ml, 12 mmole). The mixture was stirred at room temperature for 24 hours. After completion of reaction, the mixture was put in an ice-water bath (200 ml), and stood still for 10 to 20 minutes to allow precipitation. The precipitate was filtered and washed with ethanol to obtain a yellowish brown compound CC-02. Mol. Wt.: 419.2580 ($C_{20}H_{16}Cl_2N_2O_4$); $R_f$: 0.23 (ethyl acetate:n-hexane=1:2); Yield: 51%; Mp.: 179-180° C. (EtOH); HRMS (EI) m/z: calcd [M]$^+$, 418.0487 ($C_{20}H_{16}Cl_2N_2O_4^+$). Found, 418.0494. $^1$H-NMR (300 MHz, DMSO-$d_6$) δ (ppm): 2.94-3.03 (m, 4H, —CH$_2$—), 3.86-3.94 (m, 4H, —CH$_2$Cl), 7.88-7.90 (m, 2H, Ar—H), 8.10-8.15 (m, 2H, Ar—H), 8.08 (d, J=8.1 Hz, 1H, Ar—H), 8.42 (d, J=8.7 Hz, 1H, Ar—H), 9.50 (s, 1H, Ar—NH—), 10.02 (s, 1H, Ar—NH—); $^{13}$C-NMR (75 MHz, DMSO-$d_6$) δ (ppm): 40.20, 40.26, 125.94, 126.29, 126.87, 127.61, 127.79, 128.33, 129.79, 132.27, 134.26, 134.36, 134.52, 140.28, 168.86 (NCO), 169.43 (NCO), 181.63 (CO), 183.22 (CO).

Example 6

1,2-bis-(4-chlorobutyramido)-anthraquinone (CC-03)

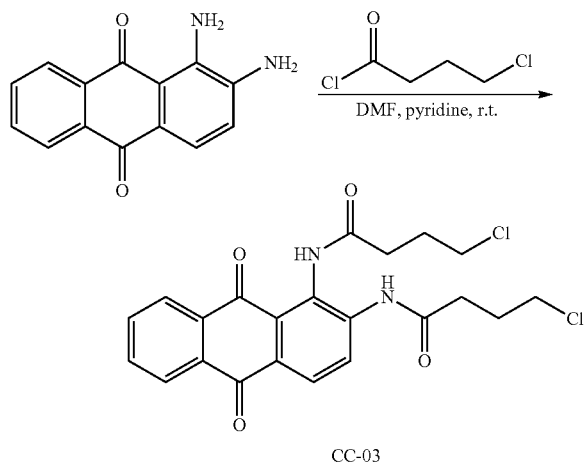

CC-03

1,2-diaminoanthraquinone (0.92 g, 4 mmole) was dissolved in anhydrous N, N-dimethylformamide (30 ml). Nitrogen was insufflated in the reaction flask at room temperature. To the solution, was added successively with pyridine (0.5 ml) (0.5 ml), and 4-chlorobutyryl chloride (1.4 ml, 12 mmole). The mixture was stirred at room temperature for 24 hours. After completion of reaction, the mixture was put in an ice-water bath (200 ml), and stood still for 10 to 20 minutes to allow precipitation. The precipitate was filtered and washed with ethanol to obtain a yellowish brown compound CC-03. Mol. Wt.: 447.3112 ($C_{22}H_{20}Cl_2N_2O_4$); $R_f$: 0.37 (ethyl acetate:n-hexane=1:2); Yield: 45%; Mp.: 154-155° C. (EtOH); HRMS (EI) calcd [M]$^+$, 446.0800 ($C_{22}H_{20}Cl_2N_2O_4{}^+$). Found, 446.0793. $^1$H-NMR (300 MHz, DMSO-d$_6$) δ (ppm): 2.04-2.12 (m, 4H, —CH$_2$—), 2.57-2.66 (m, 4H, —CH$_2$—), 3.71 (t, J=6.6 Hz, 2H, —CH$_2$—), 3.78 (t, J=6.6 Hz, 2H, —CH$_2$—), 7.88-7.91 (m, 2H, Ar—H), 8.08-8.16 (m, 3H, Ar—H), 8.36 (d, J=8.7 Hz, 1H, Ar—H), 9.52 (s, 1H; Ar—NH—), 9.82 (s, 1H, Ar—NH—); $^{13}$C-NMR (300 MHz, DMSO-d$_6$) δ (ppm): 27.68, 27.76, 33.11, 33.37, 44.75, 44.99, 125.55, 126.28, 126.85, 127.88, 128.21 128.40, 129.57, 132.28, 134.23, 134.47, 134.53, 140.45, 171.12 (NCO), 171.60 (NCO), 181.71 (CO), 183.46 (CO).

Example 7

1,2-bis-(4-methylbenzamido)-anthraquinone (CC-04)

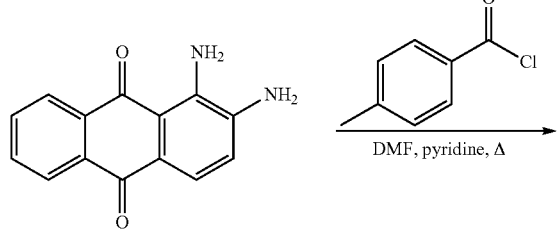

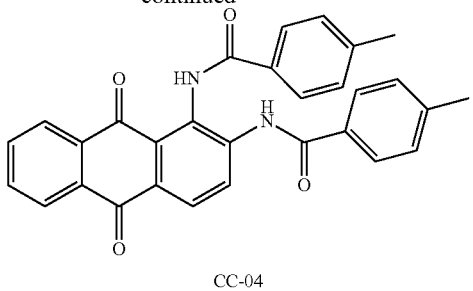

CC-04

1,2-diaminoanthraquinone (0.92 g, 4 mmole) was dissolved in anhydrous tetrahydrofuran (30 ml). To the solution, pyridine (0.5 ml), and 4-toluoyl chloride (1.6 ml, 12 mmole) were added successively at room temperature and the mixture was stirred for 5 to 10 minutes. Then, the mixture was stirred within a mini-reactor in an oil bath at temperature of 120-130° C. for 3 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a drab compound CC-04. Mol. Wt.: 474.5067 ($C_{30}H_{22}N_2O_4$); $R_f$: 0.51 (ethyl acetate:n-hexane=1:2); Yield: 62%; Mp.: 227-229° C. (EtOH); HRMS (EI) m/z: calcd [M]$^+$, 474.1580 ($C_{30}H_{22}N_2O_4{}^+$). Found, 474.1572. $^1$H-NMR (300 MHz, DMSO-d$_6$) δ (ppm): 2.36 (s, 3H, —CH$_3$), 2.42 (s, 3H, —CH$_3$), 7.33 (d, J=8.4 Hz, 2H, Ar—H), 7.42 (d, J=8.4 Hz, 2H, Ar—H), 7.79 (d, J=8.1 Hz, 2H, Ar—H), 7.90-7.93 (m, 2H, Ar—H), 8.01 (d, J=8.1 Hz, 1H, Ar—H), 8.13-8.16 (m, 1H, Ar—H), 8.18-8.20 (m, 1H, Ar—H), 8.42 (d, J=8.7 Hz, 1H, Ar—H), 10.06 (s, 1H, Ar—NH—), 10.90 (s, 1H, Ar—NH—); $^{13}$C-NMR (300 MHz, DMSO-d$_6$) δ (ppm): 20.37, 20.48, 125.02, 125.90, 126.61, 126.90, 127.45, 128.88, 128.92, 129.28, 129.70, 129.99, 130.39, 130.57, 131.79, 133.85, 134.00, 134.14, 138.94, 142.12, 142.20, 164.50 (NCO), 165.85 (NCO), 181.21 (CO), 183.84 (CO).

Example 8

1-(amino)-2-(chloroacetamido)-anthraquinone (CC-05)

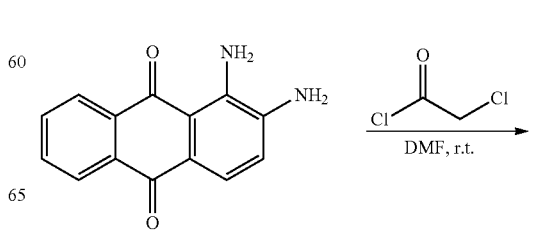

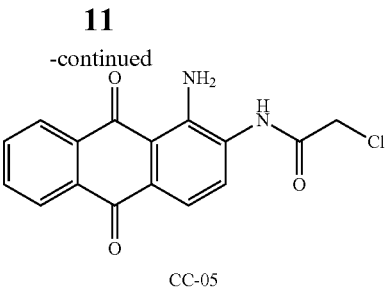

CC-05

1,2-diaminoanthraquinone (1.19 g, 5 mmole) was dissolved in anhydrous N, N-dimethylformamide (30 ml). Nitrogen was insufflated in the reaction flask at room temperature. Chloroacetyl chloride (0.5 ml, 6 mmole) was added into the solution. The mixture was stirred at room temperature for 2 hours. After completion of reaction, the mixture was put in an ice-water bath (200 ml), and stood still for 10 to 20 minutes to allow precipitation. The precipitate was filtered and washed with hot ethanol to obtain a red compound CC-05. Mol. Wt.: 314.7231 ($C_{16}H_{11}N_2O_3$); $R_f$: 0.82 (ethyl acetate:n-hexane=1:4); Yield: 65%; Mp.: 193-194° C. (EtOH); HRMS (EI) m/z: calcd [M]$^+$, 314.0458 ($C_{16}H_{11}N_2O_3^+$). Found, 314.0455. $^1$H-NMR (300 MHz, DMSO-d$_6$) δ (ppm): 4.38 (s, 2H, —CH$_2$Cl), 7.48 (d, J=7.8 Hz, 1H, Ar—H), 7.74 (d, J=8.1 Hz, 1H, Ar—H), 7.84 (dd, J=8.1 Hz, J=1.8 Hz, 1H, Ar—H), 7.88 (t, J=1.5 Hz, 1H, Ar—H), 7.91 (dd, J=7.5 Hz, J=1.5 Hz, 1H, Ar—H), 7.96 (br, 2H, Ar—NH$_2$), 8.14 (dd, J=7.2 Hz, J=1.8 Hz, 1H, Ar—H), 8.22 (dd, J=7.8 Hz, J=1.5 Hz, 1H, Ar—H), 9.80 (s, 1H, Ar—NH—); $^{13}$C-NMR (75 MHz, DMSO-d$_6$) δ (ppm): 43.25, 112.98, 115.62, 126.69, 126.55, 129.88, 128.88, 128.92, 130.25, 131.01, 132.64, 133.65, 134.37, 165.72 (NCO), 182.28 (CO), 184.38 (CO).

Example 9

1-[(2-chloropropanyl)amido]-2-(chloroacetamido)-anthraquinone (CC-06)

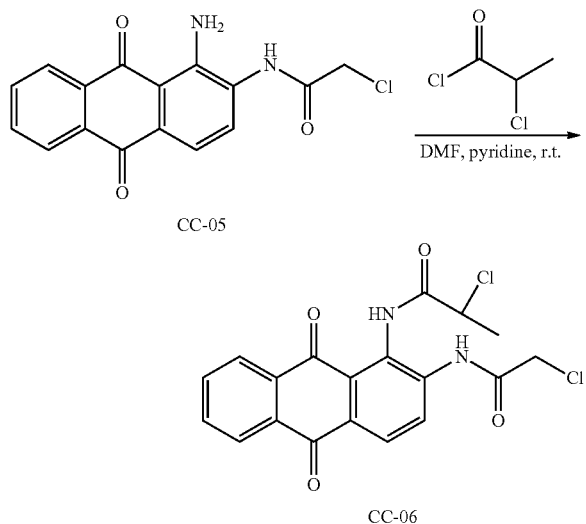

Compound CC-05 (1.28 g, 4 mmole) was dissolved in anhydrous N,N-dimethylformamide (30 ml). Nitrogen was insufflated in the reaction flask at room temperature. To the solution, was added successively with pyridine (0.5 ml) (0.5 ml), and 2-chloropropanoyl chloride (1.32 ml, 12 mmole). The mixture was stirred at room temperature for 1 hours. After completion of reaction, the mixture was put in an ice-water bath (200 ml), and stood still for 10 to 20 minutes to allow precipitation. The precipitate was filtered and washed with ethanol to obtain a yellowish brown compound CC-06. Mol. Wt.: 405.2315 ($C_{19}H_{14}Cl_2N_2O_4$); $R_f$: 0.61 (ethyl acetate:n-hexane=1:2); Yield: 28%; Mp.: 175-176° C. (EtOH); HRMS (EI) m/z: calcd [M]$^+$, 404.0331 ($C_{19}H_{14}Cl_2N_2O_4^+$). Found, 404.0339. $^1$H-NMR (300 MHz, CDCl$_3$) δ (ppm): 1.92 (s, 3H, —CH$_3$), 4.23 (s, 2H, —CH2Cl), 4.67-4.74 (m, 1H, —CH$_2$—), 7.79-7.86 (m, 2H, Ar—H), 8.27-8.37 (m, 4H, Ar—H), 9.50 (s, 1H, Ar—NH—), 11.930 (s, 1H, Ar—NH—); $^{13}$C-NMR (75 MHz, DMSO-d$_6$) δ (ppm): 21.35, 43.04, 54.64, 125.99, 126.29, 126.84, 128.53, 128.68, 130.59, 132.21, 134.19, 134.32, 134.52, 139.18, 165.27 (NCO), 168.58 (NCO), 181.51 (CO), 183.34 (CO).

Example 10

1-[(3-chloropropanyl)amido]-2-(chloroacetamido)-anthraquinone (CC-07)

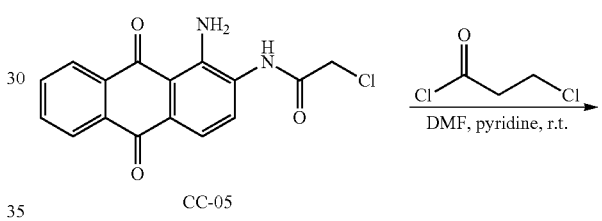

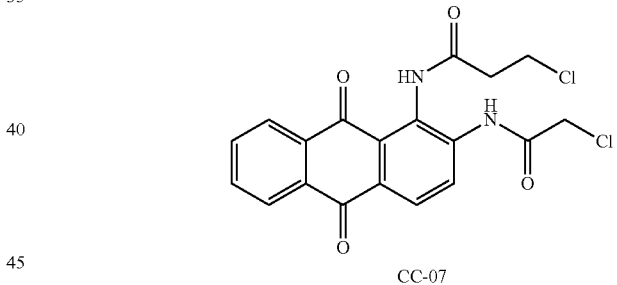

Compound CC-05 (1.28 g, 4 mmole) was dissolved in anhydrous N,N-dimethylformamide (30 ml). Nitrogen was insufflated in the reaction flask at room temperature. To the solution, was added successively with pyridine (0.5 ml) (0.5 ml), and 3-chloropropionyl chloride (1.2 ml, 12 mmole). The mixture was stirred at room temperature for 24 hours. After completion of reaction, the mixture was put in an ice-water bath (200 ml), and stood still for 10 to 20 minutes to allow precipitation. The precipitate was filtered and washed with ethanol to obtain a yellowish brown compound CC-07. Mol. Wt.: 405.2315 ($C_{19}H_{14}C_{12}N_2O_4$); $R_f$: 0.43 (ethyl acetate:n-hexane=1:2); Yield: 33%; Mp: 182-183° C. (EtOH); HRMS (EI) m/z: calcd [M]$^+$, 404.0331 ($C_{19}H_{14}C_{12}N_2O_4^+$). Found, 404.0334. $^1$H-NMR (300 MHz, CDCl$_3$) δ (ppm): 3.13 (t, J=6.3 Hz, 2H, —CH$_3$), 3.96 (t, J=6.6 Hz, 2H, —CH$_3$), 4.21 (s, 2H, —CH2Cl), 7.81-7.84 (m, 2H, Ar—H), 8.25-8.34 (m, 4H, Ar—H), 9.73 (s, 1H, Ar—NH), 11.51 (s, 1H, Ar—NH—); $^{13}$C-NMR (125 MHz, DMSO-d$_6$) δ (ppm): 43.33, 125.92, 126.28, 126.46, 126.82, 126.97, 127.90, 128.00, 128.92, 130.28, 132.18, 134.19, 134.28, 134.52, 139.56, 164.50 (NCO), 165.85 (NCO), 183.09 (CO), 183.09 (CO).

Example 11

1-[(4-chlorobutanyl)amido]-2-(chloroacetamido)-anthraquinone (CC-08)

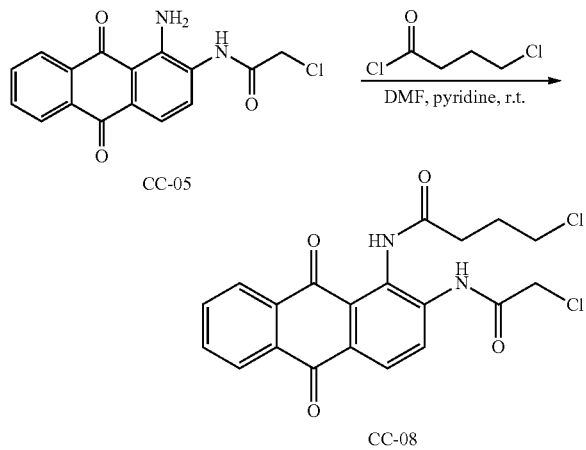

Compound CC-05 (1.28 g, 4 mmole) was dissolved in anhydrous N,N-dimethylformamide (30 ml). Nitrogen was insufflated in the reaction flask at room temperature. To the solution, was added successively with pyridine (0.5 ml) (0.5 ml), and 4-chlorobutyryl chloride (1.4 ml, 12 mmole). The mixture was stirred at room temperature for 24 hours. After completion of reaction, the mixture was put in an ice-water bath (200 ml), and stood still for 10 to 20 minutes to allow precipitation. The precipitate was filtered and washed with ethanol to obtain a yellowish brown compound CC-08. Mol. Wt.: 419.2580 ($C_{20}H_{16}Cl_2N_2O_4$); $R_f$: 0.52 (ethyl acetate:n-hexane=1:2); Yield: 38%; Mp: 163-164° C. (EtOH); HRMS (EI) m/z: calcd [M]$^+$, 418.0487 ($C_{20}H_{16}Cl_2N_2O_4^+$). Found, 418.0494. $^1$H-NMR (300 MHz, CDCl$_3$) δ (ppm): 2.28-2.34 (m, 2H, —CH$_2$—), 3.13 (t, J=6.3 Hz, 2H, —CH$_3$), 2.88 (t, J=7.2 Hz, 2H, —CH$_2$—), 3.73 (t, J=6.3 Hz, 2H, —CH$_2$—), 4.22 (s, 2H, —CH2Cl), 7.81-7.83 (m, 2H, Ar—H), 8.26-8.34 (m, 4H, Ar—H), 9.84 (s, 1H, Ar—NH—), 11.46 (s, 1H, Ar—NH—); $^{13}$C-NMR (125 MHz, DMSO-d$_6$) δ (ppm): 44.99, 125.67, 126.26, 126.79, 127.91, 128.01, 128.73, 130.21, 132.16, 134.23, 134.26, 134.52, 165.34 (NCO), 171.81 (NCO), 181.49 (CO), 183.21 (CO).

Example 12

1-(benzamido)-2-(chloroacetamido)-anthraquinone (CC-09)

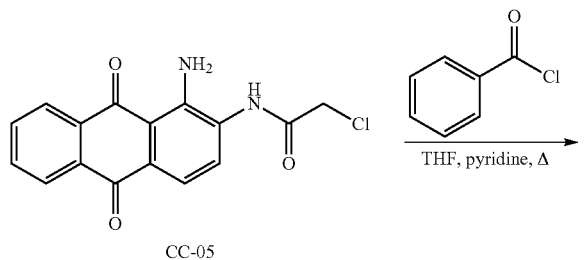

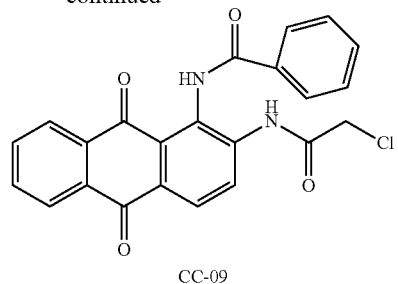

Compound CC-05 (1.28 g, 4 mmole) was dissolved in anhydrous tetrahydrofuran (30 ml). To the solution, pyridine (0.5 ml), and benzoyl chloride (1.23 ml, 12 mmole) were added successively at room temperature and the mixture was stirred for 5 to 10 minutes. Then, the mixture was stirred within a mini-reactor in an oil bath at temperature of 120-130° C. for 3 hours. After the completion of the reaction, the mixture was filtered, and the filtrate was concentrated by reduced pressure concentrator (such as Vacuum Evaporator). The residue was extracted with ethyl acetate for several times. The extract was dried on magnessium sulfate, and concentrated under reduced pressure. The crude product was washed with ethyl acetate/hexane. Finally, the crude product was recrystallized in hot ethanol to obtain a yellowish brown compound CC-09. Mol. Wt.: 418.8292 ($C_{23}H_{15}ClN_2O_4$); $R_f$: 0.83 (ethyl acetate:n-hexane=1:1); Yield: 67%; Mp.: 203-204° C. (EtOH); HRMS (EI) m/z: calcd [M]$^+$, 418.0720 ($C_{23}H_{15}ClN_2O_4^+$). Found, 418.0716. $^1$H-NMR (300 MHz, DMSO-d$_6$) δ (ppm): 4.42 (s, 2H, —CH$_2$Cl), 7.57-7.67 (m, 2H, Ar—H), 7.78-7.92 (m, 2H, Ar—H), 8.09-8.18 (m, 4H, Ar—H), 8.24 (d, J=8.7 Hz, 1H, Ar—H), 8.40 (d, J=8.7 Hz, 1H, Ar—H), 9.86 (s, 1H, Ar—NH—), 10.58 (s, 1H, Ar—NH—); $^{13}$C-NMR (75 MHz, DMSO-d$_6$) δ (ppm): 43.19, 125.76, 126.28, 126.95, 127.79, 127.95, 128.40, 128.51, 129.56, 130.43, 132.00, 132.22, 133.97, 134.23, 134.34, 134.50, 139.44, 165.42 (NCO), 166.35 (NCO), 181.55 (CO), 183.77 (CO).

Example 13

1-(2-methylbenzamido)-2-(chloroacetamido)-anthraquinone (CC-10)

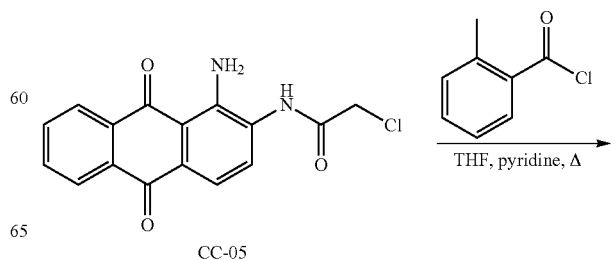

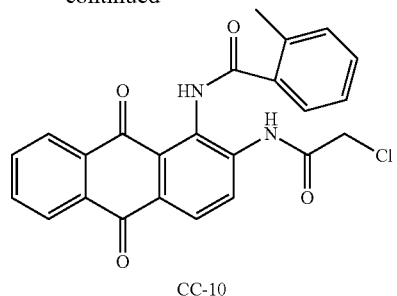

CC-10

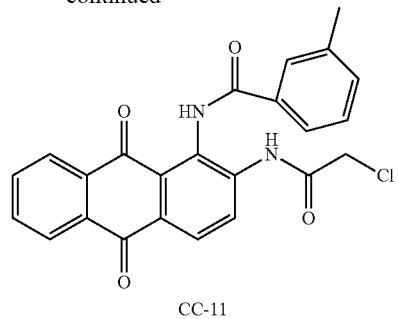

CC-11

Compound CC-05 (1.28 g, 4 mmole) was dissolved in anhydrous tetrahydrofuran (30 ml). To the solution, pyridine (0.5 ml), and 2-toluoyl chloride (1.62 ml, 12 mmole) were added successively at room temperature and the mixture was stirred for 5 to 10 minutes. Then, the mixture was stirred within a mini-reactor in an oil bath at temperature of 120-130° C. for 3 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a yellowish brown compound CC-10. Mol. Wt.: 432.8558 ($C_{24}H_{17}ClN_2O_4$); $R_f$: 0.47 (ethyl acetate:n-hexane=1:2); Yield: 47%; Mp.: 179-180° C. (EtOH); HRMS (EI) m/z: calcd [M]$^+$, 432.0877 ($C_{24}H_{17}ClN_2O_4^+$). Found, 432.0877. $^1$H-NMR (300 MHz, CDCl$_3$) δ (ppm): 2.52 (s, 3H, —CH$_3$), 4.20 (s, 2H, —CH$_2$Cl), 7.48-7.50 (m, 2H, Ar—H), 7.79-7.83 (m, 2H, Ar—H), 7.99-8.01 (m, 2H, Ar—H), 8.26-8.33 (m, 4H, Ar—H), 10.08 (s, 1H, Ar—NH—), 12.35 (s, 1H, Ar—NH—); $^{13}$C-NMR (75 MHz, CDCl$_3$) δ (ppm): 21.39, 43.12, 124.08, 125.16, 125.16, 125.60, 127.24, 127.63, 128.91, 128.91, 129.06, 131.71, 132.07, 132.91, 133.32, 133.81, 134.35, 134.83, 136.53, 139.15 165.44 (NCO), 168.03 (NCO), 181.68 (CO), 187.58 (CO).

Compound CC-05 (1.28 g, 4 mmole) was dissolved in anhydrous tetrahydrofuran (30 ml). To the solution, pyridine (0.5 ml), and 3-toluoyl chloride (1.62 ml, 12 mmole) were added successively at room temperature and the mixture was stirred for 5 to 10 minutes. Then, the mixture was stirred within a mini-reactor in an oil bath at temperature of 120-130° C. for 3 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a yellowish brown compound CC-11. Mol. Wt.: 432.8558 ($C_{24}H_{17}ClN_2O_4$), $R_f$: 0.62 (ethyl acetate:n-hexane=1:2); Yield: 56%; Mp.: 202-203° C. (EtOH); HRMS (EI) m/z calcd [M]$^+$, 432.0877 ($C_{24}H_{17}ClN_2O_4^+$). Found, 432.0873. $^1$H-NMR (300 MHz, CDCl$_3$) δ (ppm): 2.52 (s, 3H, —CH$_3$), 4.20 (s, 2H, —CH$_2$Cl), 7.48-7.50 (m, 2H, Ar—H), 7.80-7.83 (m, 2H, Ar—H), 7.99-8.01 (m, 2H, Ar—H), 8.26-8.32 (m, 4H, Ar—H), 10.08 (s, 1H, Ar—NH—), 12.36 (s, 1H, Ar—NH—); $^{13}$C-NMR (75 MHz, CDCl$_3$) δ (ppm): 21.39, 43.12, 124.07, 125.15, 125.60, 127.24, 127.63, 128.91, 128.91, 129.06, 131.70, 132.08, 132.91, 133.30, 133.81, 134.29, 134.36, 136.84, 136.51, 139.15, 165.45 (NCO), 168.03 (NCO), 181.69 (CO), 187.58 (CO).

Example 14

1-(3-methylbenzamido)-2-(chloroacetamido)-anthraquinone (CC-11)

Example 15

1-(4-methylbenzamido)-2-(chloroacetamido)-anthraquinone (CC-12)

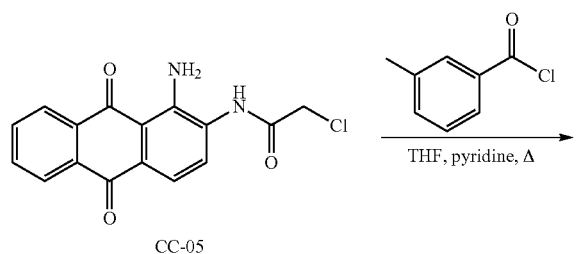

CC-05

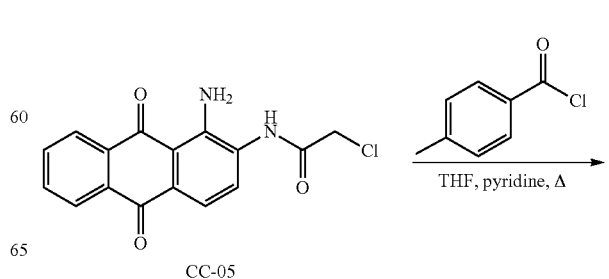

CC-05

-continued

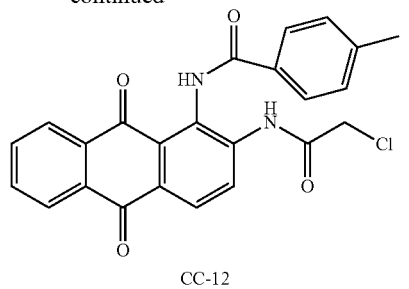

CC-12

-continued

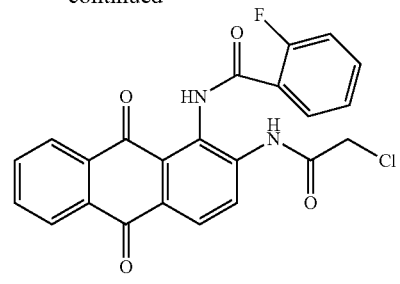

CC-13

Compound CC-05 (1.28 g, 4 mmole) was dissolved in anhydrous tetrahydrofuran (30 ml). To the solution, pyridine (0.5 ml), and 4-toluoyl chloride (1.62 ml, 12 mmole) were added successively at room temperature and the mixture was stirred for 5 to 10 minutes. Then, the mixture was stirred within a mini-reactor in an oil bath at temperature of 120-130° C. for 3 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a yellowish brown compound CC-12. Mol. Wt.: 432.8558 ($C_{24}H_{17}ClN_2O_4$); $R_f$: 0.76 (ethyl acetate:n-hexane=1:2); Yield: 66%; Mp.: 198-199° C. (EtOH); HRMS (EI) m/z: calcd [M]$^+$, 432.0877 ($C_{24}H_{17}ClN_2O_4^+$). Found, 432.0881. $^1$H-NMR (300 MHz, DMSO-$d_6$) δ (ppm): 2.43 (s, 31-1, —CH$_3$), 4.43 (s, 2H, —CH$_2$Cl), 7.41 (d, J=7.8 Hz, 2H, Ar—H), 7.88-7.91 (m, 2H, Ar—H), 8.01 (d, J=8.1 Hz, 2H, Ar—H), 8.10-8.13 (m, 1H, Ar—H), 8.16-8.19 (m, 1H, Ar—H), 8.24 (d, J=8.7 Hz, 1H, Ar—H), 8.39 (d, J=9.0 Hz, 1H, Ar—H), 9.84 (s, 1H, Ar—NH—), 10.58 (s, 1H, Ar—NH—); $^{13}$C-NMR (300 MHz, CDCl$_3$) δ (ppm): 20.90, 43.53, 123.99, 125.52, 127.23, 127.60, 128.24, 129.87, 130.52, 131.66, 132.02, 132.94, 133.01, 134.29, 134.33, 136.80, 136.51, 143.22, 164.83 (NCO), 167.15 (NCO), 181.07 (CO), 187.00 (CO).

Compound CC-05 (1.28 g, 4 mmole) was dissolved in anhydrous tetrahydrofuran (30 ml). To the solution, pyridine (0.5 ml), and 2-fluorobenzoyl chloride (1.42 ml, 12 mmole) were added successively at room temperature and the mixture was stirred for 5 to 10 minutes. Then, the mixture was stirred within a mini-reactor in an oil bath at temperature of 120-130° C. for 3 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a yellowish brown compound CC-13. Mol. Wt.: 436.8197 ($C_{23}H_{14}ClFN_2O_4$); $R_f$: 0.62 (ethyl acetate:n-hexane=1:2); Yield: 31%; Mp.: 245-246° C. (EtOH); HRMS (EI) m/z: calcd [M]$^+$, 436.0626 ($C_{23}H_{14}ClFN_2O_4^+$). Found, 436.0630. $^1$H-NMR (300 MHz, DMSO-$d_6$) δ (ppm): 4.41 (s, 2H, —CH$_2$Cl), 7.40-7.47 (m, 2H, Ar—H), 7.65-7.72 (m, 1H, Ar—H), 7.86-7.93 (m, 2H, Ar—H), 8.03-8.19 (m, 3H, Ar—H), 8.24 (d, J=8.4 Hz, 1H, Ar—H), 8.37 (d, J=8.7 Hz, 1H, Ar—H), 9.83 (s, 1H, Ar—NH—), 10.48 (s, 1H, Ar—NH—); $^{13}$C-NMR (75 MHz, DMSO-$d_6$) δ (ppm): 43.11, 116.43, 116.65, 124.71, 125.86, 126.29, 126.94, 127.83, 128.50, 128.96, 130.98, 132.23, 133.80, 133.92, 134.24, 134.35, 134.51, 139.27, 162.97 (NCO), 165.41 (NCO), 181.55 (CO), 183.82 (CO).

Example 16

1-(2-fluorobenzamido)-2-(chloroacetamido)-anthraquinone (CC-13)

Example 17

1-(3-fluorobenzamido)-2-(chloroacetamido)-anthraquinone (CC-14)

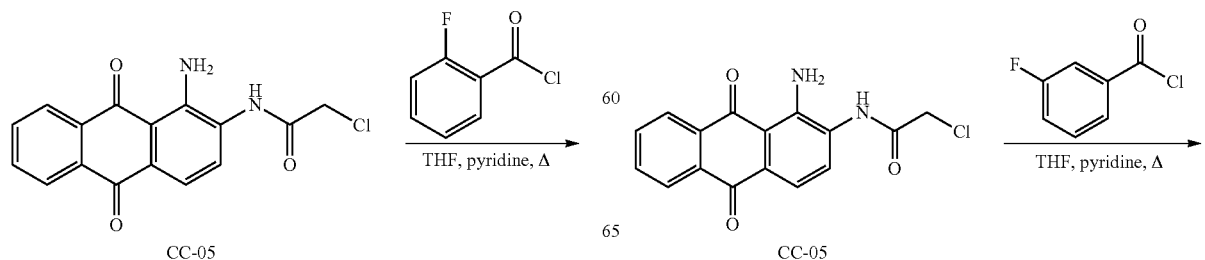

-continued

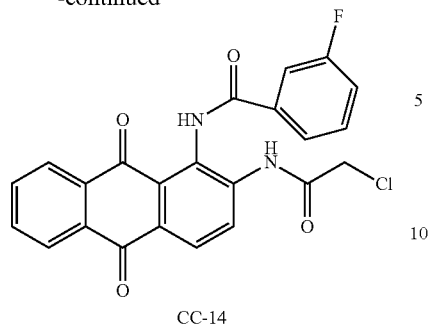

CC-14

Compound CC-05 (1.28 g, 4 mmole) was dissolved in anhydrous tetrahydrofuran (30 ml). To the solution, pyridine (0.5 ml), and 3-fluorobenzoyl chloride (1.42 ml, 12 mmole) were added successively at room temperature and the mixture was stirred for 5 to 10 minutes. Then, the mixture was stirred within a mini-reactor in an oil bath at temperature of 120-130° C. for 3 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a yellowish brown compound CC-14. Mol. Wt.: 436.8197 ($C_{23}H_{14}ClFN_2O_4$); $R_f$: 0.48 (ethyl acetate:n-hexane=1: 2); Yield: 47%; Mp.: 197-198° C. (EtOH); HRMS (EI) m/z: calcd [M]$^+$, 436.0626 ($C_{23}H_{14}ClFN_2O_4^+$). Found, 436.0623. $^1$H-NMR (300 MHz, DMSO-d$_6$) δ (ppm): 4.43 (s, 2H, —CH$_2$Cl), 7.48-7.55 (m, 1H, Ar—H), 7.63-7.70 (m, 1H, Ar—H), 7.86-7.96 (m, 4H, Ar—H), 8.10-8.13 (m, 1H, Ar—H), 8.15-8.19 (m, 1H, Ar—H), 8.26 (d, J=8.7 Hz, 1H, Ar—H), 8.44 (d, J=8.7 Hz, 1H, Ar—H), 9.85 (s, 1H, Ar—NH—), 10.49 (s, 1H, Ar—NH—); $^{13}$C-NMR (75 MHz, DMSO-d$_6$) δ (ppm): 43.21, 114.61, 114.91, 118.63, 118.90, 124.18, 126.12, 126.30, 126.96, 128.14, 128.24, 128.84, 130.37, 130.64, 130.74, 132.23, 134.23, 134.35, 134.54, 136.55, 140.00, 162.97 (NCO), 165.54 (NCO), 181.55 (CO), 183.41 (CO).

Example 18

1-(4-fluorobenzamido)-2-(chloroacetamido)-anthraquinone (CC-15)

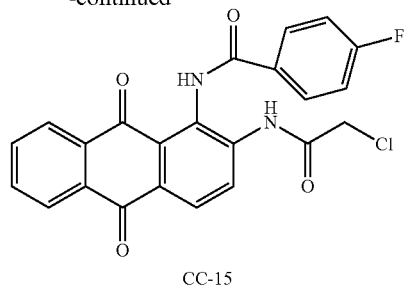

CC-15

Compound CC-05 (1.28 g, 4 mmole) was dissolved in anhydrous tetrahydrofuran (30 ml). To the solution, pyridine (0.5 ml), and 4-fluorobenzoyl chloride (1.42 ml, 12 mmole) were added successively at room temperature and the mixture was stirred for 5 to 10 minutes. Then, the mixture was stirred within a mini-reactor in an oil bath at temperature of 120-130° C. for 3 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a green-brown compound CC-15. Mol. WI: 436.8197 ($C_{23}H_{14}ClFN_2O_4$); $R_f$: 0.72 (ethyl acetate:n-hexane=1:2); Yield: 62%; Mp.: 184-185° C. (EtOH); HRMS (EI) m/z: calcd [M]$^+$, 436.0626 ($C_{23}H_{14}ClFN_2O_4^+$). Found, 436.0625. $^1$H-NMR (300 MHz, DMSO-d) δ (ppm): 4.42 (s, 2H, —CH$_2$Cl), 7.44 (t, J=9.0 Hz, 2H, Ar—H), 7.88-7.91 (m, 2H, Ar—H), 8.09-8.18 (m, 4H, Ar—H), 8.25 (d, J=8.7 Hz, 1H, Ar—H), 8.42 (d, J=8.7 Hz, 1H, Ar—H), 9.84 (s, 1H, Ar—NH—), 10.51 (s, 1H, Ar—NH—); $^{13}$C-NMR (75 MHz, DMSO-d$_6$) δ (ppm): 43.21, 114.61, 114.91, 118.63, 118.90, 124.18, 126.12, 126.30, 126.96, 128.14, 128.24, 128.84, 130.37, 130.64, 130.74, 132.23, 134.23, 134.35, 134.54, 136.55, 140.00, 162.97 (NCO), 165.54 (NCO), 181.55 (CO), 183.41 (CO).

Example 19

1-(2-chlorobenzamido)-2-(chloroacetamido)-anthraquinone (CC-16)

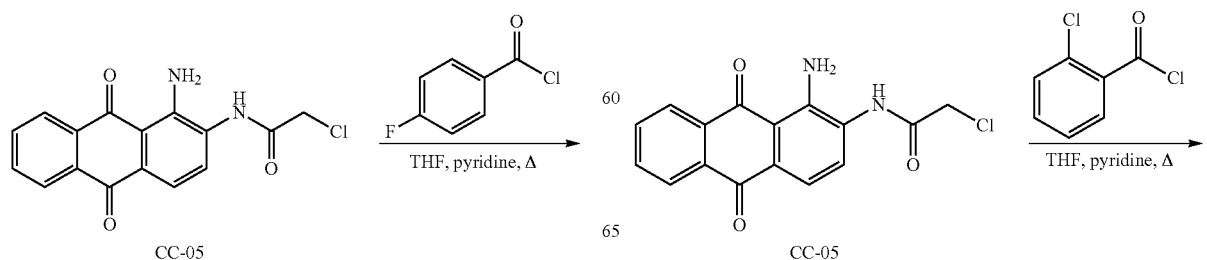

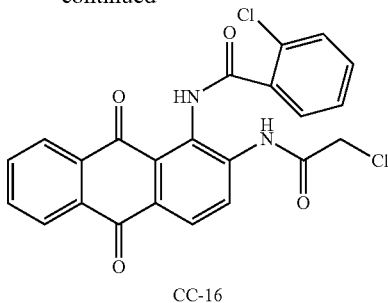

CC-16

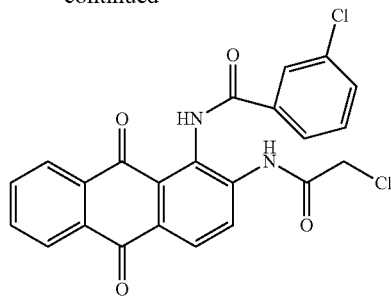

CC-17

Compound CC-05 (1.28 g, 4 mmole) was dissolved in anhydrous tetrahydrofuran (30 ml). To the solution, pyridine (0.5 ml), and 2-chlorobenzoyl chloride (1.42 ml, 12 mmole) were added successively at room temperature and the mixture was stirred for 5 to 10 minutes. Then, the mixture was stirred within a mini-reactor in an oil bath at temperature of 120-130° C. for 3 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a chartreuse compound CC-16. Mol. Wt.: 453.2743 ($C_{23}H_{14}Cl_2N_2O_4$); $R_f$: 0.47 (ethyl acetate:n-hexane=1:2); Yield: 46%; Mp.: 193-194° C. (EtOH); HRMS (EI) m/z: calcd $[M]^+$, 452.0331 ($C_{23}H_{14}Cl_2N_2O_4^+$). Found, 436.0325. $^1$H-NMR (300 MHz, DMSO-$d_6$) δ (ppm): 4.43 (s, 2H, —$CH_2Cl$), 7.57-7.60 (m, 3H, Ar—H), 7.89-7.94 (m, 2H, Ar—H), 8.08-8.19 (m, 3H, Ar—H), 8.26 (d, J=8.7 Hz, 1H, Ar—H), 8.37 (d, J=8.7 Hz, 1H, Ar—H), 9.76 (s, 1H, Ar—NH—), 10.44 (s, 1H, Ar—NH—); $^{13}$C-NMR (75 MHz, DMSO-d) δ (ppm): 43.16, 126.16, 126.32, 126.93, 127.19, 128.37, 128.53, 129.49, 130.14, 130.63, 130.76, 131.73, 134.24, 134.34, 134.56, 135.29, 139.44, 165.36 (NCO), 165.54 (NCO), 181.55 (CO), 183.44 (CO).

Compound CC-05 (1.28 g, 4 mmole) was dissolved in anhydrous tetrahydrofuran (30 ml). To the solution, pyridine (0.5 ml), and 3-chlorobenzoyl chloride (1.42 ml, 12 mmole) were added successively at room temperature and the mixture was stirred for 5 to 10 minutes. Then, the mixture was stirred within a mini-reactor in an oil bath at temperature of 120-130° C. for 3 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a yellowish brown compound CC-17. Mol. Wt.: 453.2743 ($C_{23}H_{14}Cl_2N_2O_4$); $R_f$: 53 (ethyl acetate:n-hexane=1:2); Yield: 51%; Mp.: 188-189° C. (EtOH); HRMS (EI) m/z: calcd $[M]^+$, 452.0331 ($C_{23}H_{14}Cl_2N_2O_4^+$). Found, 436.0330. $^1$H-NMR (300 MHz, DMSO-$d_6$) δ (ppm): 4.43 (s, 2H, —$CH_2Cl$), 7.72-7.64 (m, 2H, Ar—H), 7.87-7.91 (m, 2H, Ar—H), 8.02-8.19 (m, 4H, Ar—H), 8.26 (d, J=8.4 Hz, 1H, Ar—H), 8.45 (d, J=8.4 Hz, 1H, Ar—H), 9.79 (s, 1H, Ar—NH—), 10.49 (s, 1H, Ar—NH—); $^{13}$C-NMR (75 MHz, DMSO-$d_6$) δ (ppm): 43.28, 126.11, 126.24, 126.36, 126.79, 127.01, 127.88, 128.01, 128.37, 128.74, 130.36, 130.53, 131.73, 132.27, 133.33, 134.17, 134.26, 134.41, 134.60, 136.28, 165.23 (NCO), 165.64 (NCO), 181.61 (CO), 183.36 (CO).

Example 20

1-(3-chlorobenzamido)-2-(chloroacetamido)-anthraquinone (CC-17)

Example 21

1-(4-chlorobenzamido)-2-(chloroacetamido)-anthraquinone (CC-18)

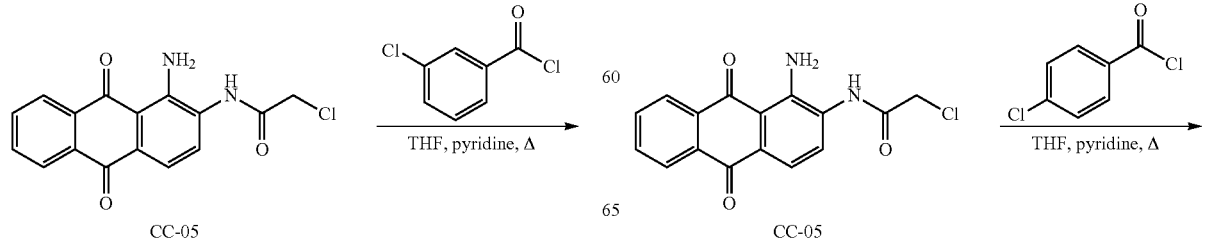

-continued

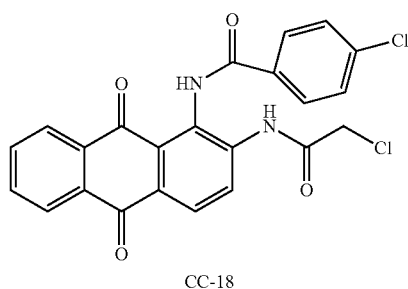

CC-18

-continued

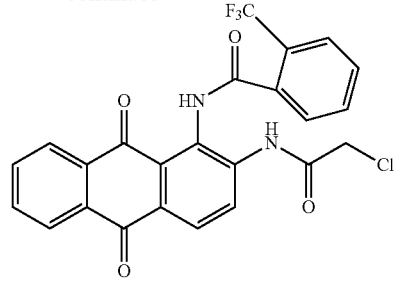

CC-19

Compound CC-05 (1.28 g, 4 mmole) was dissolved in anhydrous tetrahydrofuran (30 ml). To the solution, pyridine (0.5 ml), and 4-chlorobenzoyl chloride (1.44 ml, 12 mmole) were added successively at room temperature and the mixture was stirred for 5 to 10 minutes. Then, the mixture was stirred within a mini-reactor in an oil bath at temperature of 120-130° C. for 3 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a yellowish brown compound CC-18. Mol. Wt.: 453.2743 ($C_{23}H_{14}Cl_2N_2O_4$); $R_f$: 0.64 (ethyl acetate:n-hexane=1:2); Yield: 67%; Mp.: 224-225° C. (EtOH); HRMS (EI) m/z: calcd [M]$^+$, 452.0331 ($C_{23}H_{14}Cl_2N_2O_4^+$). Found, 436.0333. $^1$H-NMR (300 MHz, DMSO-$d_6$) δ (ppm): 4.42 (s, 2H, —CH$_2$Cl), 7.68-7.71 (m, 2H, Ar—H), 7.88-7.91 (m, 2H, Ar—H), 8.08-8.18 (m, 4H, Ar—H), 8.25 (d, J=8.4 Hz, 1H, Ar—H), 8.43 (d, J=8.7 Hz, 1H, Ar—H), 9.86 (s, 1H, Ar—NH—), 10.52 (s, 1H, Ar—NH—); $^{13}$C-NMR (75 MHz, DMSO-$d_6$) δ (ppm): 43.23, 126.06, 126.33, 126.96, 128.21, 128.61, 129.06, 129.93, 130.40, 132.25, 132.92, 134.38, 134.56, 136.91, 139.87, 165.50 (NCO), 165.53 (NCO), 181.58 (CO), 183.51 (CO).

Compound CC-05 (1.28 g, 4 mmole) was dissolved in anhydrous tetrahydrofuran (30 ml). To the solution, pyridine (0.5 ml), and 2-(trifluoromethyl)benzoyl chloride (1.78 ml, 12 mmole) were added successively at room temperature and the mixture was stirred for 5 to 10 minutes. Then, the mixture was stirred within a mini-reactor in an oil bath at temperature of 120-130° C. for 4 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a chartreuse compound CC-19. Mol. Wt.: 486.8272 ($C_{24}H_{14}ClF_3N_2O_4$); $R_f$: 0.42 (ethyl acetate:n-hexane=1:2); Yield: 32%; Mp.: 248-250° C. (EtOH); HRMS (EI) m/z: calcd [M]$^+$, 486.0594 ($C_{24}H_{14}ClF_3N_2O_4^+$). Found, 486.0587. $^1$H-NMR (300 MHz, DMSO-$d_6$) δ (ppm): 4.38 (s, 2H, —CH$_2$Cl), 7.80 (t, J=7.4 Hz, 1H, Ar—H), 7.90-7.97 (m, 4H, Ar—H), 8.13-8.29 (m, 4H, Ar—H), 8.37 (d, J=8.4 Hz, 1H, Ar—H), 9.72 (s, 1H, Ar—NH—), 10.49 (s, 1H, Ar—NH—); $^{13}$C-NMR (125 MHz, DMSO-$d_6$) δ (ppm): 43.32, 126.27, 126.33, 126.63, 126.87, 128.13, 128.64, 129.01, 130.66, 130.76, 132.18, 132.59, 134.23, 134.35, 134.58, 139.39, 165.31 (NCO), 166.00 (NCO), 181.45 (CO), 183.24 (CO).

Example 22

1-[2-(trifluoromethyl)benzamido]-2-(chloroacetamido)-anthraquinone (CC-19)

Example 23

1-[3-(trifluoromethyl)benzamido]-2-(chloroacetamido)-anthraquinone (CC-20)

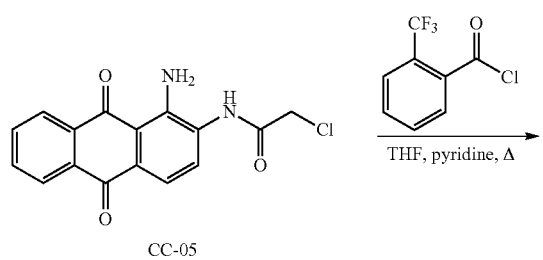

CC-05

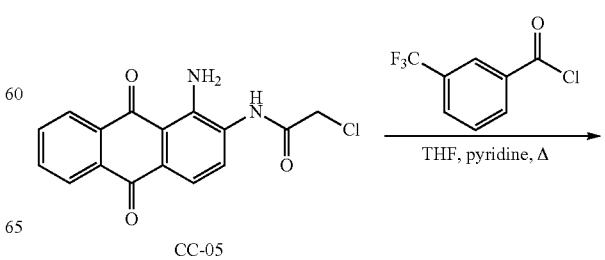

CC-05

-continued

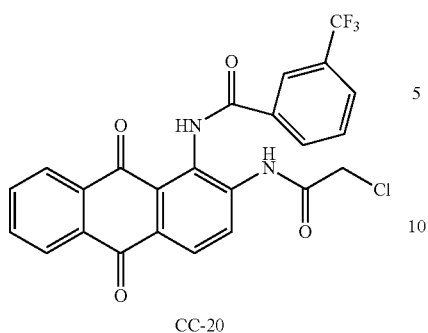

CC-20

Compound CC-05 (1.28 g, 4 mmole) was dissolved in anhydrous tetrahydrofuran (30 ml). To the solution, pyridine (0.5 ml), and 3-(trifluoromethyl)benzoyl chloride (1.78 ml, 12 mmole) were added successively at room temperature and the mixture was stirred for 5 to 10 minutes. Then, the mixture was stirred within a mini-reactor in an oil bath at temperature of 120-130° C. for 4 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a gold compound CC-20. Mol. Wt.: 486.8272 ($C_{24}H_{14}ClF_3N_2O_4$); $R_f$: 0.52 (ethyl acetate:n-hexane=1:2); Yield: 48%; Mp.: 190-191° C. (EtOH); HRMS (EI) m/z: calcd [M]$^+$, 486.0594 ($C_{24}H_{14}ClF_3N_2O_4^+$). Found, 486.0596. $^1$H-NMR (300 MHz, DMSO-$d_6$) δ (ppm): 4.38 (s, 2H, —CH$_2$Cl), 7.84-7.93 (m, 3H, Ar—H), 8.04 (d, J=7.5 Hz, 1H, Ar—H), 8.08-8.11 (m, 1H, Ar—H), 8.16-8.19 (m, 1H, Ar—H), 8.27 (d, J=9.0 Hz, 1H, Ar—H), 8.38-8.49 (m, 3H, Ar—H), 9.90 (s, 1H, Ar—NH—), 10.58 (s, 1H, Ar—NH—); $^{13}$C-NMR (75 MHz, DMSO-$d_6$) δ (ppm): 43.25, 124.66, 126.32, 126.96, 127.98, 128.39, 128.48, 128.55, 129.82, 130.34, 132.07, 132.25, 134.22, 134.37, 134.55, 135.27, 140.30, 165.24 (NCO), 165.63 (NCO), 181.56 (CO), 183.25 (CO).

Example 24

1-[4-(trifluoromethyl)benzamido]-2-(chloroacetamido)-anthraquinone (CC-21)

-continued

CC-21

Compound CC-05 (1.28 g, 4 mmole) was dissolved in anhydrous tetrahydrofuran (30 ml). To the solution, pyridine (0.5 ml), and 4-(trifluoromethyl)benzoyl chloride (1.78 ml, 12 mmole) were added successively at room temperature and the mixture was stirred for 5 to 10 minutes. Then, the mixture was stirred within a mini-reactor in an oil bath at temperature of 120-130° C. for 4 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a brown compound CC-21. Mol. Wt.: 486.8272 ($C_{24}H_{14}ClF_3N_2O_4$), $R_f$: 0.63 (ethyl acetate:n-hexane=1:2); Yield: 57%; Mp.: 203-204° C. (EtOH); HRMS (EI) m/z: calcd [M]$^+$, 486.0594 ($C_{24}H_{14}ClF_3N_2O_4^+$). Found, 486.0597. $^1$H-NMR (300 MHz, DMSO-$d_6$) δ (ppm): 4.43 (s, 2H, —CH$_2$Cl), 7.88-7.91 (m, 2H, Ar—H), 8.01 (d, J=8.4 Hz, 2H, Ar—H), 8.08-8.11 (m, 1H, Ar—H), 8.16-8.19 (m, 1H, Ar—H), 8.25-8.32 On, 3H, Ar—H), 8.45 (d, J=8.3 Hz, 1H, Ar—H), 9.90 (s, 1H, Ar—NH—), 10.60 (s, 1H, Ar—NH—); $^{13}$C-NMR (75 MHz, DMSO-$d_6$) δ (ppm): 43.25, 122.15, 125.48, 125.53, 125.77, 126.27, 126.34, 126.95, 128.11, 128.39, 128.66, 128.93, 130.37, 131.56, 131.99, 132.26, 134.24, 134.39, 134.57, 138.02, 140.12, 165.42 (NCO), 165.61 (NCO), 181.57 (CO), 183.35 (CO).

Example 25

1-1-[2,5-bis-(trifluoromethyl)benzamido]-2-(chloroacetamido)-anthraquinone (CC-22)

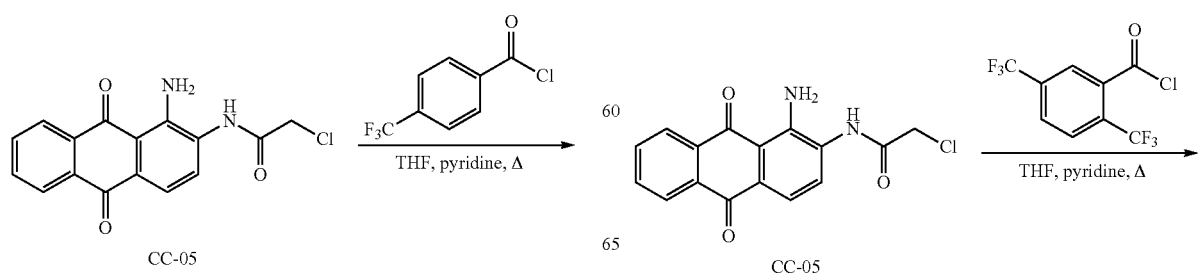

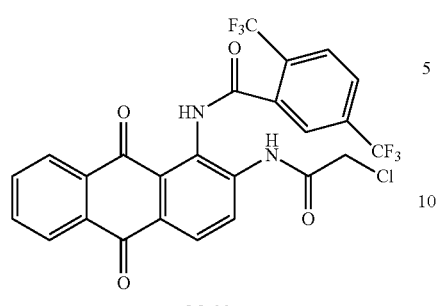

CC-22

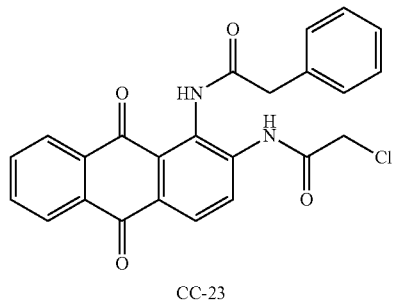

CC-23

Compound CC-05 (1.28 g, 4 mmole) was dissolved in anhydrous tetrahydrofuran (30 ml). To the solution, pyridine (0.5 ml), and 2,5-bis-(trifluoromethyl)benzoyl chloride (1 ml, 6 mmole) were added successively at room temperature and the mixture was stirred for 5 to 10 minutes. Then, the mixture was stirred within a mini-reactor in an oil bath at temperature of 120-130° C. for 4 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a khaki compound CC-22. Mol. Wt.: 554.8251 ($C_{24}H_{14}ClF_3N_2O_4$); $R_f$: 0.63 (ethyl acetate:n-hexane=1:2); Yield: 42%; Mp.: 187-188° C. (EtOH); HRMS (EI) m/z: calcd [M]$^+$, 554.0468 ($C_{24}H_{14}ClF_3N_2O_4^+$). Found, 554.0468. $^1$H-NMR (300 MHz, DMSO-$d_6$) δ (ppm): 4.38 (s, 2H, —CH$_2$Cl), 7.90-7.95 (m, 2H, Ar—H), 8.11-8.22 (m, 5H, Ar—H), 8.29 (d, J=8.4 Hz, 1H, Ar—H), 8.40 (d, J=8.7 Hz, 1H, Ar—H), 8.69 (s, 1H, Ar—H), 9.85 (s, 1H, Ar—NH—), 10.69 (s, 1H, Ar—NH—); $^{13}$C-NMR (300 MHz, DMSO-$d_6$) δ (ppm): 42.94, 126.35, 126.59, 126.83, 127.77, 127.90, 128.21, 128.27, 128.68, 128.75, 130.75, 134.21, 134.42, 134.63, 136.22, 139.90, 164.63 (NCO), 165.39 (NCO), 181.50 (CO), 183.26 (CO).

Compound CC-05 (1.28 g, 4 mmole) was dissolved in anhydrous tetrahydrofuran (30 ml). To the solution, pyridine (0.5 ml), and phenylacetyl chloride (1.6 ml, 12 mmole) were added successively at room temperature and the mixture was stirred for 5 to 10 minutes. Then, the mixture was stirred within a mini-reactor in an oil bath at temperature of 120-130° C. for 4 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a Clay brown compound CC-23. Mol. Wt.: 432.8558 ($C_{24}H_{17}ClN_2O_4$); $R_f$: 0.46 (ethyl acetate:n-hexane=1:2); Yield: 34%; Mp.: 184-185° C. (EtOH); HRMS (EI) m/z: calcd [M]$^+$, 432.0877 ($C_{24}H_{17}ClN_2O_4^+$). Found, 432.0885. $^1$H-NMR (300 MHz, DMSO-$d_6$) δ (ppm): 3.86 (s, 2H, —CH$_2$—), 4.36 (s, 2H, —CH$_2$Cl), 7.23-7.93 (m, 5H, Ar—H), 7.89-7.93 (m, 2H, Ar—H), 8.11-8.20 (m, 3H, Ar—H), 8.31 (d, J=8.7 Hz, 1H, Ar—H), 9.66 (s, 1H, Ar—NH—), 10.25 (s, 1H, Ar—NH—); $^{13}$C-NMR (125 MHz, DMSO-$d_6$) δ (ppm): 25.08, 42.51, 43.20, 43.34, 66.97, 125.59, 126.26, 126.53, 126.83, 127.92, 128.15, 128.86, 129.30, 129.66, 128.75, 130.30, 132.16, 134.22, 134.29, 134.52, 135.35, 142.78, 145.07, 165.25 (NCO), 170.57 (NCO), 181.51 (CO), 183.25 (CO).

Example 26

1-[2-(phenyl)acetylamino]-2-(chloroacetamido)-anthraquinone (CC-23)

Example 27

1-[2-(4-fluorophenyl)acetylamino]-2-(chloroacetamido)-anthraquinone (CC-24)

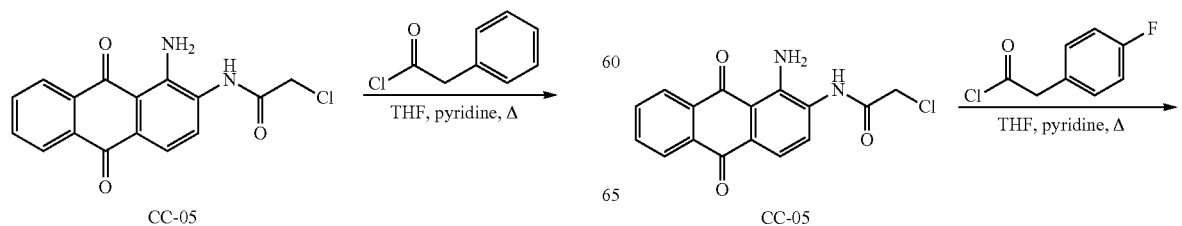

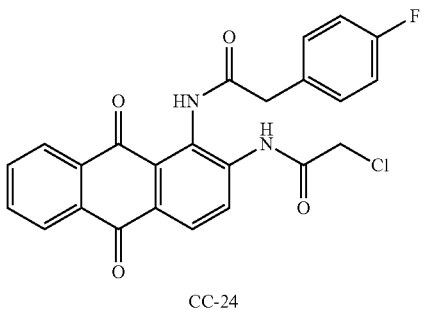

CC-24

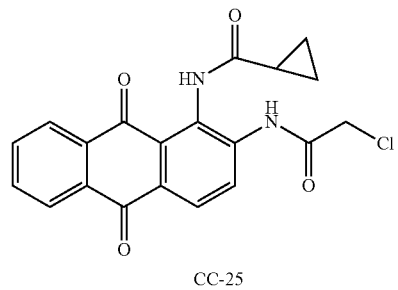

CC-25

Compound CC-05 (1.28 g, 4 mmole) was dissolved in anhydrous tetrahydrofuran (30 ml). To the solution, pyridine (0.5 ml), and 4-fluorophenylacetyl chloride (1.7 ml, 12 mmole) were added successively at room temperature and the mixture was stirred for 5 to 10 minutes. Then, the mixture was stirred within a mini-reactor in an oil bath at temperature of 120-130° C. for 4 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a Clay brown compound CC-24. Mol. Wt.: 450.8462 ($C_{24}H_{16}ClFN_2O_4$); $R_f$: 0.37 (ethyl acetate:n-hexane=1:2); Yield: 37%; Mp.: 213-214° C. (EtOH); HRMS (EI) m/z: calcd [M]$^+$, 450.0783 ($C_{24}H_{16}ClFN_2O_4^+$). Found, 450.0782. $^1$H-NMR (300 MHz, DMSO-d$_6$) δ (ppm): 3.86 (s, 2H, —CH$_2$—), 4.37 (s, 2H, —CH$_2$Cl), 7.17 (t, J=9.0 Hz, 1H, Ar—H), 7.42-7.47 (m, 2H, Ar—H), 7.90-7.93 (m, 2H, Ar—H), 8.11-8.23 (m, 3H, Ar—H), 8.32 (d, J=8.7 Hz, 1H, Ar—H), 9.64 (s, 1H, Ar—NH—), 10.20 (s, 1H, Ar—NH—); $^{13}$C-NMR (300 MHz, DMSO-d$_6$) δ (ppm): 41.48, 43.03, 114.69, 114.97, 125.67, 126.26, 126.79, 127.79, 128.15, 128.28, 129.14, 130.45, 131.42, 131.53, 132.23, 134.27, 134.50, 139.18, 165.23 (NCO), 170.70 (NCO), 181.54 (CO), 183.46 (CO).

Example 28

1-[(cyclopropanecarbonyl)amino]-2-(chloroacetamido)-anthraquinone (CC-25)

Compound CC-05 (1.28 g, 4 mmole) was dissolved in anhydrous tetrahydrofuran (30 ml). To the solution, pyridine (0.5 ml), and cyclopropanecarbonyl chloride (0.6 ml, 6 mmole) were added successively at room temperature and the mixture was stirred for 5 to 10 minutes. Then, the mixture was stirred within a mini-reactor in an oil bath at temperature of 120-130° C. for 4 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a yellowish-brown compound CC-25. Mol. Wt.: 382.7971 ($C_{20}H_{15}ClN_2O_4$); $R_f$: 0.43 (ethyl acetate:n-hexane=1:2); Yield: 27%; Mp.: 191-192° C. (EtOH); HRMS (EI) m/z: calcd [M]$^+$, 382.0720 ($C_{20}H_{15}ClN_2O_4^+$). Found, 382.0712. $^1$H-NMR (300 MHz, CDCl$_3$) δ (ppm): 1.02-1.08 (m, 2H, —CH$_2$—), 1.26-1.80 (m, 2H, —CH$_2$—), 1.92-1.97 (m, 1H, —C$_{1-12}$—), 4.20 (s, 2H, —CH$_2$Cl), 7.80-7.85 (m, 2H, Ar—H), 8.26-8.33 (m, 4H, Ar—H), 10.01 (s, 1H, Ar—NH—), 11.75 (s, 1H, Ar—NH—); $^{13}$C-NMR (75 MHz, CDCl$_3$) δ (ppm): 0.86, 9.16, 16.15, 43.14, 123.55, 125.35, 127.21, 127.53, 131.49, 131.80, 132.61, 132.94, 134.33, 134.75, 136.41, 165.29 (NCO), 175.30 (NCO), 181.69 (CO), 187.40 (CO).

Example 29

1-[(cyclohexanecarbonyl)amino]-2-(chloroacetamido)-anthraquinone (CC-26)

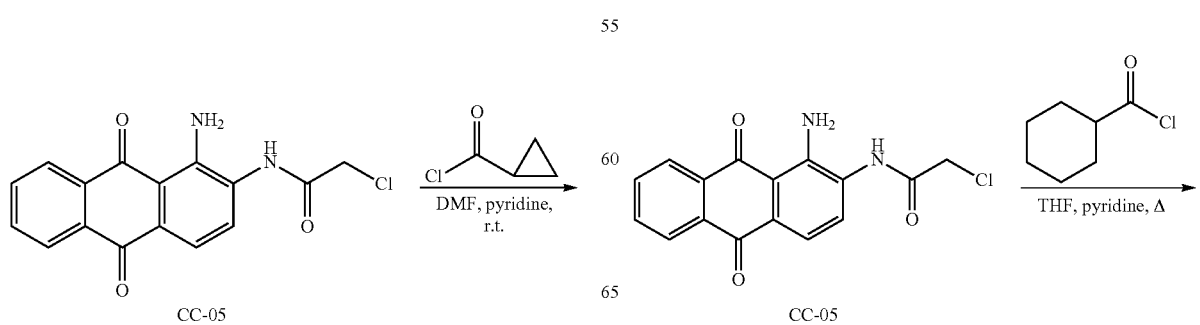

-continued

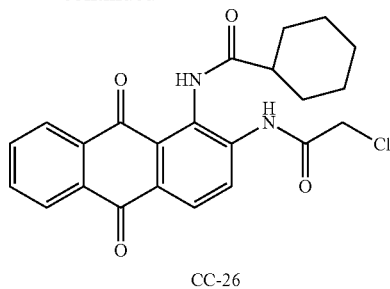

CC-26

Compound CC-05 (1.28 g, 4 mmole) was dissolved in anhydrous tetrahydrofuran (30 ml). To the solution, pyridine (0.5 ml), and cyclohexanecarbonyl chloride (0.88 ml, 6 mmole) were added successively at room temperature and the mixture was stirred for 5 to 10 minutes. Then, the mixture was stirred within a mini-reactor in an oil bath at temperature of 120-130° C. for 4 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a yellowish-brown compound CC-26. Mol. Wt.: 424.8768 ($C_{23}H_{21}ClN_2O_4$); $R_f$: 0.47 (ethyl acetate:n-hexane=1:2); Yield: 52%; Mp.: 216-217° C. (EtOH); HRMS (EI) m/z: calcd [M]$^+$, 424.1190 ($C_{23}H_{21}ClN_2O_4^+$). Found, 424.1194. $^1$H-NMR (300 MHz, DMSO-$d_6$) δ (ppm): 1.20-1.49 (m, 6H, —CH$_2$—), 1.67-1.83 (m, 2H, —CH$_2$—), 2.06 (d, J=11.4 Hz, 2H, —CH$_2$—), 4.43 (s, 2H, —CH$_2$Cl), 7.89-7.92 (m, 2H, Ar—H), 8.13-8.19 (m, 3H, Ar—H), 8.28 (d, J=8.7 Hz, 1H, Ar—H), 9.57 (s, 1H, Ar—NH—), 10.12 (s, 1H, Ar—NH—); $^{13}$C-NMR (75 MHz, DMSO-$d_6$) δ (ppm): 25.03, 25.32, 28.68, 43.15, 44.36, 125.34, 126.30, 126.92, 127.27, 128.74, 129.89, 130.61, 132.22, 134.29, 134.32, 134.55, 138.65, 165.16 (NCO), 175.60 (NCO), 181.61 (CO), 183.80 (CO).

-continued

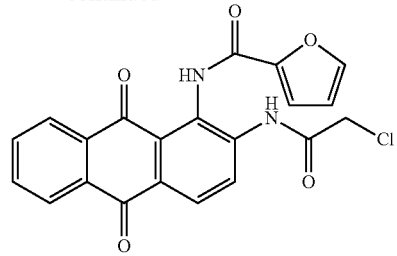

CC-27

Compound CC-05 (1.28 g, 4 mmole) was dissolved in anhydrous tetrahydrofuran (30 ml). To the solution, pyridine (0.5 ml), and 2-furoyl chloride (1.22 ml, 12 mmole) were added successively at room temperature and the mixture was stirred for 5 to 10 minutes. Then, the mixture was stirred within a mini-reactor in an oil bath at temperature of 120-130° C. for 4 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a brown compound CC-27. Mol. Wt.: 408.7913 ($C_{21}H_{13}ClN_2O_5$); $R_f$: 0.57 (ethyl acetate:n-hexane=1:2); Yield: 63%; Mp.: 211-212° C. (EtOH); HRMS (EI) m/z: calcd [M]$^+$, 408.0513 ($C_{21}H_{13}ClN_2O_5^+$). Found, 408.0518. $^1$H-NMR (300 MHz, DMSO-$d_6$) δ (ppm): 4.43 (s, 2H, —CH$_2$Cl), 6.77-6.79 (m, 2H, —HC=CH—), 7.38 (d, J=3.0 Hz, 1H, —HC=CH—), 7.88-7.92 (m, 2H, Ar—H), 8.06 (d, J=0.9 Hz, 1H, —HC=CH—), 8.22 (d, J=8.7 Hz, 1H, Ar—H), 8.39 (d, J=8.7 Hz, 1H, Ar—H), 9.93 (s, 1H, Ar—NH—), 10.60 (s, 1H, Ar—NH—); $^{13}$C-NMR (75 MHz, DMSO-$d_6$) δ (ppm): 43.26, 112.51, 115.71, 125.74, 126.37, 127.05, 127.56, 128.59, 128.82, 130.37, 132.27, 134.26, 134.47, 134.61, 139.34, 157.15 (NCO), 165.60 (NCO), 181.60 (CO), 184.03 (CO).

Example 30

1-[(2-furoyl)amino]-2-(chloroacetamido)-anthraquinone (CC-27)

Example 31

1-[(2-thiophenecarbonyl)amino]-2-(chloroacetamido)-anthraquinone (CC-28)

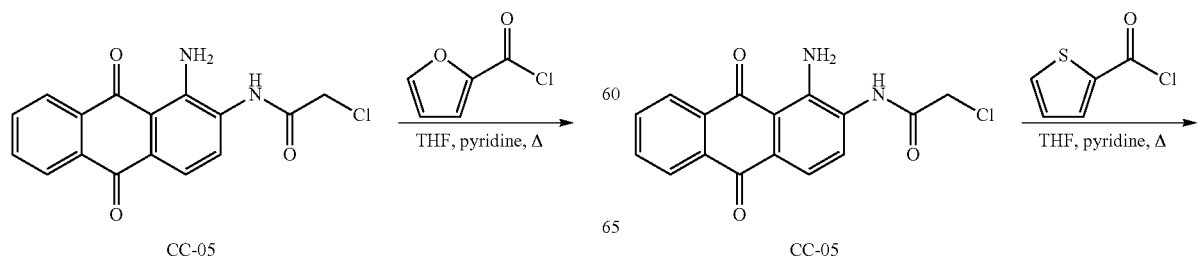

-continued

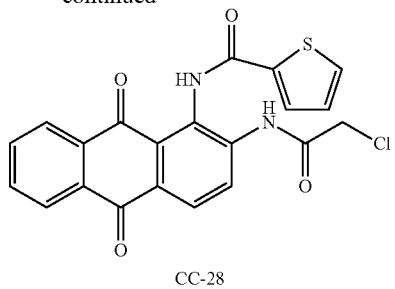

CC-28

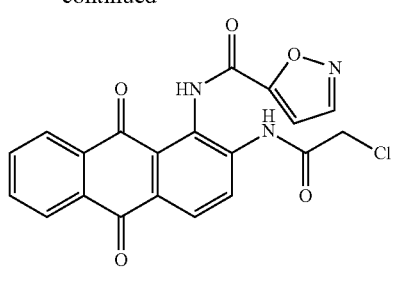

CC-29

Compound CC-05 (1.28 g, 4 mmole) was dissolved in anhydrous tetrahydrofuran (30 ml). To the solution, pyridine (0.5 ml), and 2-thiophenecarbonyl chloride (1.28 ml, 12 mmole) were added successively at room temperature and the mixture was stirred for 5 to 10 minutes. Then, the mixture was stirred within a mini-reactor in an oil bath at temperature of 120-130° C. for 4 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a red-brown compound CC-28. Mol. Wt.: 424.8569 ($C_{21}H_{13}ClN_2O_4S$); $R_f$: 52 (ethyl acetate:n-hexane=1:2); Yield: 55%; Mp.: 190-191° C. (EtOH); HRMS (EI) m/z: calcd [M]+, 424.0285 ($C_{21}H_{13}ClN_2O_4S^+$). Found, 424.0288. $^1$H-NMR (300 MHz, DMSO-$d_6$) δ (ppm): 4.45 (s, 2H, —CH$_2$Cl), 7.30-7.33 (m, 1H, —HC=CH—), 7.88-7.94 (m, 1H, —HC=CH—), 7.88-7.94 (m, 3H, Ar—H), 8.10-8.20 (m, 1H, —HC=CH—), 8.10-8.20 (m, 1H, Ar—H), 8.24 (d, J=8.4 Hz, 1H, Ar—H), 8.42 (d, J=6.9 Hz, 1H, Ar—H), 9.45 (s, 1H, Ar—NH—), 10.53 (s, 1H, Ar—NH—); $^{13}$C-NMR (75 MHz, DMSO-$d_6$) δ (ppm): 43.25, 125.95, 126.36, 127.01, 128.04, 128.24, 128.37, 128.88, 130.3, 132.26, 134.26, 134.42, 134.60, 139.08, 139.79, 161.17 (NCO), 165.60 (NCO), 181.55, 181.61 (CO), 183.59 (CO).

Example 32

1-[(5-isoxazolecarbonyl)amino]-2-(chloroacetamido)-anthraquinone (CC-29)

Compound CC-05 (1.28 g, 4 mmole) was dissolved in anhydrous tetrahydrofuran (30 ml). To the solution, pyridine (0.5 ml), and isoxazole-5-carbonyl chloride (1.14 ml, 12 mmole) were added successively at room temperature and the mixture was stirred for 5 to 10 minutes. Then, the mixture was stirred within a mini-reactor in an oil bath at temperature of 120-130° C. for 2 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a brown compound CC-29. Mol. Wt.: 409.7794 ($C_{20}H_{12}ClN_3O_5$); $R_f$: 0.43 (ethyl acetate:n-hexane=1:2); Yield: 52%; Mp.: 212-213° C. (EtOH); HRMS (EI) m/z: calcd [M]+, 409.0465 ($C_{20}H_{12}ClN_3O_5^+$). Found, 409.0472. $^1$H-NMR (300 MHz, DMSO-$d_6$) δ (ppm): 4.43 (s, 2H, —CH$_2$Cl), 7.31 (d, J=1.8 Hz, 1H, —HC=CH—), 7.88-7.94 (m, 1H, —HC=CH—), 7.88-7.92 (m, 2H, Ar—H), 8.08-8.11 (m, 1H, Ar—H), 8.15-8.18 (m, 1H, Ar—H), 8.27 (d, J=8.7 Hz, 1H, Ar—H), 8.49 (d, J=8.7 Hz, 1H, Ar—H), 8.88 (d, J=1.8 Hz, 1H, —HC=N—), 10.03 (s, 1H, Ar—NH—), 10.69 (s, 1H, Ar—NH—); $^{13}$C-NMR (75 MHz, DMSO-$d_6$) δ (ppm): 43.25, 107.12, 126.35, 126.66, 126.82, 126.98, 127.84, 128.56, 130.17, 132.24, 134.18, 134.42, 134.59, 140.46, 151.99, 155.50, 162.77 (NCO), 165.79 (NCO), 181.50 (CO), 183.06 (CO).

Example 33

1-[(2,5-dimethyl-3-furoyl)amino]-2-(chloroacetamido)-anthraquinone (CC-30)

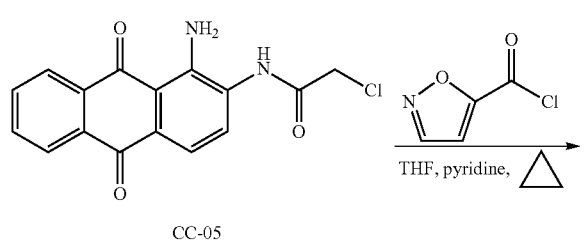

CC-05

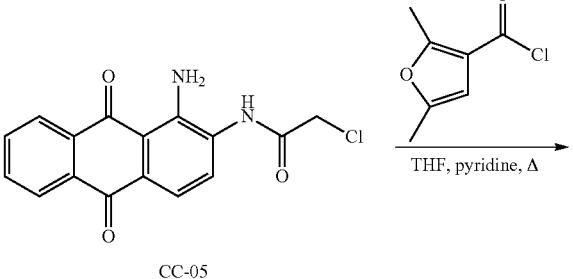

CC-05

-continued

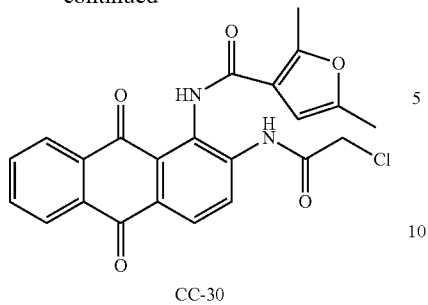

CC-30

-continued

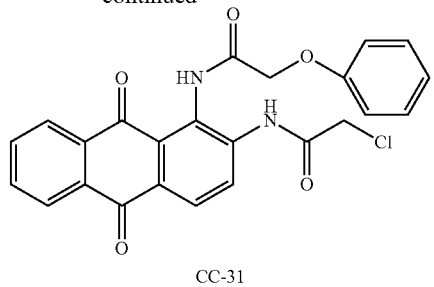

CC-31

Compound CC-05 (1.28 g, 4 mmole) was dissolved in anhydrous tetrahydrofuran (30 ml). To the solution, pyridine (0.5 ml), and 2,5-dimethylfuran-3-carbonyl chloride (1.51 ml, 12 mmole) were added successively at room temperature and the mixture was stirred for 5 to 10 minutes. Then, the mixture was stirred within a mini-reactor in an oil bath at temperature of 120-130° C. for 2 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a yellow compound CC-30. Mol. Wt.: 436.8445 ($C_{23}H_{17}ClN_2O_5$); $R_f$: 0.54 (ethyl acetate:n-hexane=1:2); Yield: 63%; Mp.: 207-208° C. (EtOH); HRMS (EI) m/z: calcd [M]$^+$, 436.0826 ($C_{23}H_{17}ClN_2O_5^+$). Found, 436.0832. $^1$H-NMR (300 MHz, DMSO-$d_6$) δ (ppm): 2.33 (s, 3H, —CH$_3$), 2.52 (s, 3H, —CH$_3$), 4.44 (s, 2H, —CH$_2$Cl), 6.70 (s, 1H, —HC═CCH$_3$), 7.89-7.92 (m, 2H, Ar—H), 8.13-8.19 (m, 2H, Ar—H), 8.21 (d, J=8.7 Hz, 1H, Ar—H), 8.34 (d, J=8.7 Hz, 1H, Ar—H), 9.83 (s, 1H, Ar—NH—), 10.29 (s, 1H, Ar—NH—); $^{13}$C-NMR (75 MHz, DMSO-$d_6$) δ (ppm): 12.74, 13.04, 43.14, 105.21, 116.20, 125.29, 126.29, 126.98, 128.82, 129.93, 130.50, 132.23, 134.23, 134.39, 134.52, 138.67, 149.74, 156.05, 162.99 (NCO), 165.30 (NCO), 181.55 (CO), 184.22 (CO).

Compound CC-05 (1.28 g, 4 mmole) was dissolved in anhydrous tetrahydrofuran (30 ml). To the solution, pyridine (0.5 ml), and phenoxyacetyl chloride (1.65 ml, 12 mmole) were added successively at room temperature and the mixture was stirred for 5 to 10 minutes. Then, the mixture was stirred within a mini-reactor in an oil bath at temperature of 120-130° C. for 2 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a yellow-green compound CC-31. Mol. Wt.: 448.8552 ($C_{24}H_{17}ClN_2O_5$); $R_f$:0.61 (ethyl acetate:n-hexane=1:2); Yield: 55%; Mp.: 217-218° C. (EtOH); HRMS (EI) m/z: calcd [M]$^+$, 448.0826 ($C_{24}H_{17}ClN_2O_5^+$). Found, 448.0824. $^1$H-NMR (300 MHz, DMSO-$d_6$) δ (ppm): 4.40 (s, 2H, —CH$_2$Cl), 4.82 (s, 2H, —CH$_2$O—), 7.02 (t, J=6.0 Hz, 1H, Ar—H), 7.16 (d, J=7.5 Hz, 1H, Ar—H), 7.35-7.40 (m, 2H, Ar—H), 7.90-7.93 (m, 2H, Ar—H), 8.13-8.18 (m, 2H, Ar—H), 8.20 (d, J=8.7 Hz, 1H, Ar—H), 8.33 (d, J=8.4 Hz, 1H, Ar—H), 9.86 (s, 1H, Ar—NH—), 10.58 (s, 1H, Ar—NH—); $^{13}$C-NMR (75 MHz, DMSO-$d_6$) δ (ppm): 43.12, 67.24, 114.94, 118.49, 121.48, 125.60, 126.29, 126.89, 127.44, 128.64, 129.54, 132.22, 134.21, 134.37, 134.52, 135.11, 138.87, 157.66, 165.41 (NCO), 168.03 (NCO), 181.50 (CO), 183.94 (CO).

Example 34

1-[2-(phenoxy)acetylamino]-2-(chloroacetamido)-anthraquinone (CC-31)

Example 35

1-[2-(phenylsulfanyl)acetylamino]-2-(chloroacetamido)-anthraquinone (CC-32)

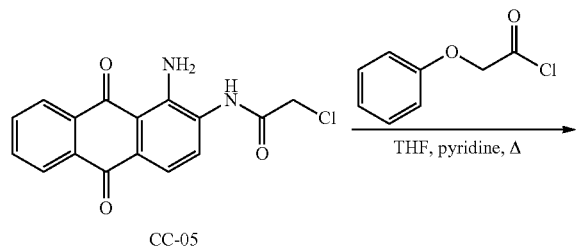

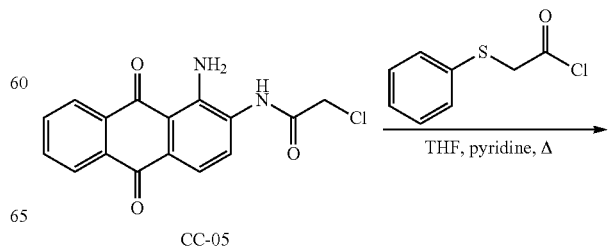

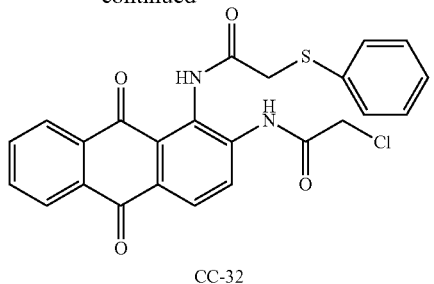

CC-32

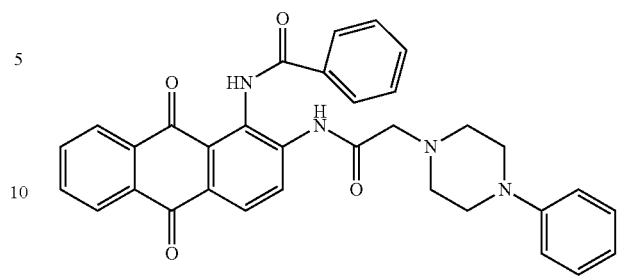

CC-33

Compound CC-05 (1.28 g, 4 mmole) was dissolved in anhydrous tetrahydrofuran (30 ml). To the solution, pyridine (0.5 ml), and (phenylthio)acetyl chloride (1.79 ml, 12 mmole) were added successively at room temperature and the mixture was stirred for 5 to 10 minutes. Then, the mixture was stirred within a mini-reactor in an oil bath at temperature of 120-130° C. for 2 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a brown compound CC-32. Mol. Wt.: 464.9208 ($C_{24}H_{17}ClN_2O_4S$); $R_f$: 0.57 (ethyl acetate:n-hexane=1:2); Yield: 59%; Mp.: 161-162° C. (EtOH); HRMS (EI) m/z: calcd [M]$^+$, 464.0598 ($C_{24}H_{17}ClN_2O_4S^+$). Found, 464.0602. $^1$H-NMR (300 MHz, DMSO-$d_6$) δ (ppm): 4.10 (s, 2H, —CH$_2$S—), 4.43 (s, 2H, —CH$_2$Cl), 7.33 (td, J=6.6 Hz, J=1.8 Hz, 2H, Ar—H), 7.45 (d, J=7.2 Hz, 2H, Ar—H), 7.86-7.93 (m, 2H, Ar—H), 8.08-8.16 (m, 2H, Ar—H), 8.21 (d, J=8.7 Hz, 1H, Ar—H), 8.30 (d, J=8.7 Hz, 1H, Ar—H), 9.71 (s, 1H, Ar—NH—), 10.46 (s, 1H, Ar—NH—); $^{13}$C-NMR (75 MHz, DMSO-$d_6$) δ (ppm): 43.82, 126.43, 126.58, 127.00, 127.51, 128.56, 129.20, 129.52, 129.66, 131.16, 132.93, 134.96, 135.23, 136.69, 139.82, 166.05 (NCO), 168.92 (NCO), 182.23 (CO), 184.16 (CO).

Compound CC-09 (0.83 g, 2 mmole) was dissolved in anhydrous tetrahydrofuran (30 ml), and to the solution was added successively with DIPEA (1 ml, 6 mmole) and N-phenylpiperazine (1.22 ml, 8 mmole) under stirring for 5 to 10 minutes. This mixture was heated under reflux for 16 hours. After completion of reaction, the mixture was filtered and the crude product was isolated from the upper layer of the filtrate and recrystallized in hot ethanol to obtain kelly green compounds CC-33. Mol. Wt.: 544.5998 ($C_{33}H_{28}N_4O_4$); $R_f$: 0.33 (ethyl acetate:n-hexane=1:2); Yield: 57%; Mp.: 225-226° C. (EtOH); HRMS (EI) m/z: calcd [M]$^+$, 544.2111 ($C_{33}H_{28}N_4O_4^+$). Found, 544.2119. $^1$H-NMR (300 MHz, DMSO-$d_6$) δ (ppm): 2.56 (br, 4H, —CH$_2$—), 2.78 (br, 4H, —CH$_2$—), 3.23 (s, 2H, —CH$_2$N—), 6.25 (d, J=7.8 Hz, 2H, Ar—H), 6.78 (t, J=7.2 Hz, 1H, Ar—H), 7.18 (t, J=8.7 Hz, 2H, Ar—H), 7.37 (t, J=7.5 Hz, 2H, Ar—H), 7.47 (1. J=7.5 Hz, 1H, Ar—H), 7.87-7.93 (m, 2H, Ar—H), 8.10 (d, J=6.0 Hz, 2H, Ar—H), 8.16-8.19 (m, 2H, Ar—H), 8.30 (d, J=8.7 Hz, 1H, Ar—H), 8.79 (d, J=8.7 Hz, 1H, Ar—H), 10.06 (s, 1H, Ar—NH—), 10.58 (s, 1H, Ar—NH—); $^{13}$C-NMR (75 MHz, DMSO-$d_6$) δ (ppm): 47.81, 52.74, 61.47, 115.56, 118.87, 125.38, 126.29, 126.65, 126.91, 127.72, 127.91, 128.03, 128.48, 128.62, 129.35, 132.14, 132.31, 133.10, 134.12, 134.44, 140.53, 150.77, 166.36 (NCO), 169.06 (NCO), 181.42 (CO), 183.64 (CO).

Example 36

1-(benzamido)-2-[2-(4-phenylpiperazino)acetylamino]-anthraquinone (CC-33)

Example 37

1-(benzamido)-2-[2-[4-(2-fluorophenyl)piperazino]acetylamino]-anthraquinone (CC-34)

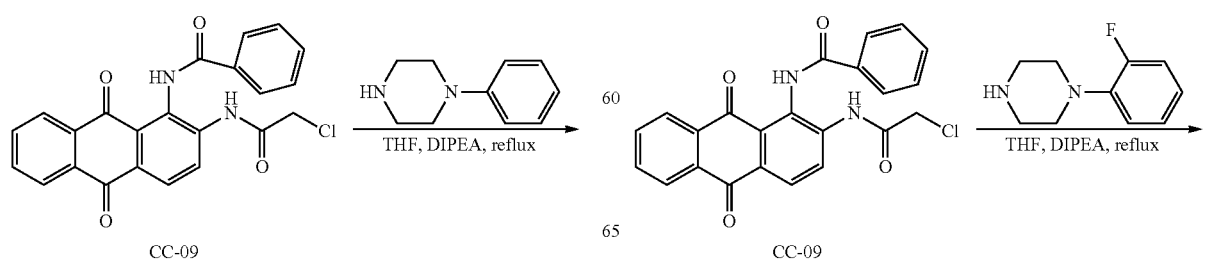

39
-continued

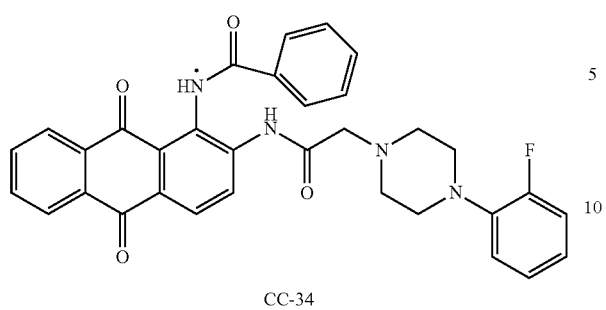

CC-34

40
-continued

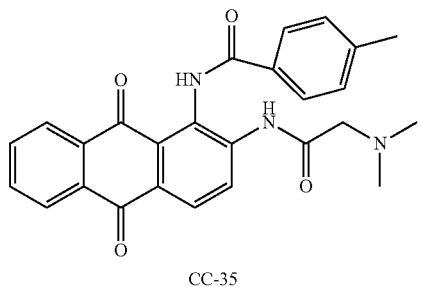

CC-35

Compound CC-09 (0.83 g, 2 mmole) was dissolved in anhydrous tetrahydrofuran (30 ml), and to the solution was added successively with DIPEA (1 ml, 6 mmole) and 1-(2-fluorophenyl)piperazine (1.26 ml, 8 mmole) under stirring for 5 to 10 minutes. This mixture was heated under reflux for 16 hours. After completion of reaction, the mixture was filtered and the crude product was isolated from the upper layer of the filtrate and recrystallized in hot ethanol to obtain reddish orange compounds CC-34. Mol. Wt.: 562.5903 ($C_{33}H_{27}FN_4O_4$); $R_f$: 37 (ethyl acetate:n-hexane=1:2); Yield: 65%; Mp.: 228-229° C. (EtOH); HRMS. (EI) m/z: calcd [M]$^+$, 562.2016 ($C_{33}H_{27}FN_4O_4{}^+$). Found, 562.2012. $^1$H-NMR (300 MHz, DMSO-d$_6$) δ (ppm): 2.59 (br, 4H, —CH$_2$—), 2.61 (br, 41-1, —CH$_2$—), 3.23 (s, 2H, —CH$_2$N—), 6.41 (t, J=8.1 Hz, 1H, Ar—H), 6.95-7.10 (m, 3H, Ar—H), 7.48-7.60 (m, 3H, Ar—H), 7.87-7.93 (m, 2H, Ar—H), 8.09-8.20 (m, 4H, Ar—H), 8.30 (d, =8.7 Hz, 1H, Ar—H), 8.80 (d, J=9.0 Hz, 1H, Ar—H), 10.06 (s, 1H, Ar—NH—), 10.62 (s, 1H, Ar—NH—); $^{13}$C-NMR (75 MHz, DMSO-d$_6$) δ (ppm): 49.53, 52.81, 61.50, 114.20, 115.51, 115.78, 119.13, 119.17, 122.24, 122.35, 124.47, 124.51, 125.31, 126.30, 126.67, 126.92, 127.69, 128.01, 128.66, 129.34, 132.28, 133.27, 134.11, 134.44, 139.32, 139.43, 140.50, 153.20, 156.44, 166.38 (NCO), 169.03 (NCO), 181.41 (CO), 183.68 (CO).

Compound CC-12 (0.86 g, 2 mmole) was dissolved in anhydrous tetrahydrofuran (30 ml), and to the solution was added successively with DIPEA (1 ml, 6 mmole) and dimethylamine (0.8 ml, 8 mmole) under stirring for 5 to 10 minutes. This mixture was heated under reflux for 16 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a yellowish-brown compound CC-35. Mol. Wt.: 441.4785 ($C_{26}H_{23}N_3O_4$); $R_f$: 0.33 (ethyl acetate:n-hexane=1:2); Yield: 54%; Mp.: 190-191° C. (EtOH); HRMS (EI) m/z: calcd [M]$^+$, 441.1689 ($C_{26}H_{23}N_3O_4{}^+$). Found, 441.1689. $^1$H-NMR (300 MHz, DMSO-d$_6$) δ (ppm): 2.11 (s, 6H, —NCH$_3$), 2.44 (s, 3H, —CH$_3$), 3.09 (s, 2H, —CH$_2$N—), 7.43 (d, J=8.1 Hz, 1H, Ar—H), 7.88-7.91 (m, 2H, Ar—H), 8.11-8.19 (m, 2H, Ar—H), 8.26 (d, J=8.7 Hz, 1H, Ar—H), 8.64 (d, J=8.4 Hz, 1H, Ar—H), 10.16 (s, 1H, Ar—NH—), 10.54 (s, 1H, Ar—NH—); $^{13}$C-NMR (75 MHz, DMSO-d$_6$) δ (ppm): 20.86, 45.16, 62.82, 125.73, 126.30, 126.47, 127.79, 127.99, 128.12, 128.89, 129.09, 129.39, 130.93, 132.32, 134.13, 134.36, 134.43, 140.34, 142.23, 166.35 (NCO), 169.14 (NCO), 181.45 (CO), 183.63 (CO).

Example 38

1-(4-methylbenzamido)-2-[2-(dimethylamino)acetylamino]-anthraquinone (CC-35)

Example 39

1-(4-methylbenzamido)-2-[2-[(1,3-dioxolan-2-ylmethyl)(methyl)amino]acetylamino]-anthraquinone (CC-36)

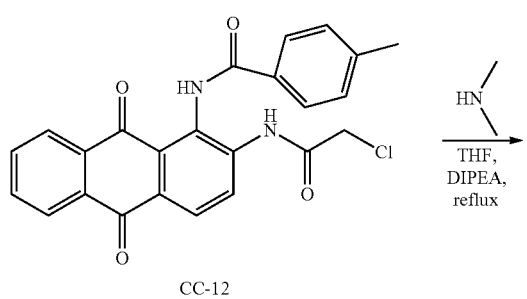

CC-12

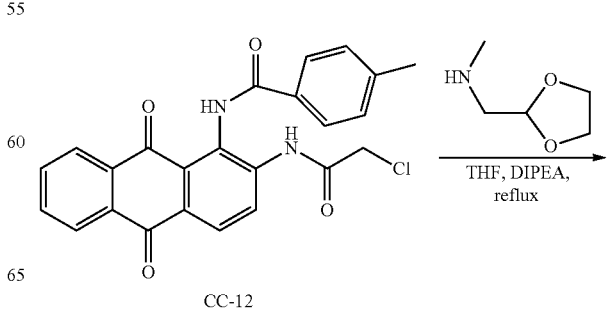

CC-12

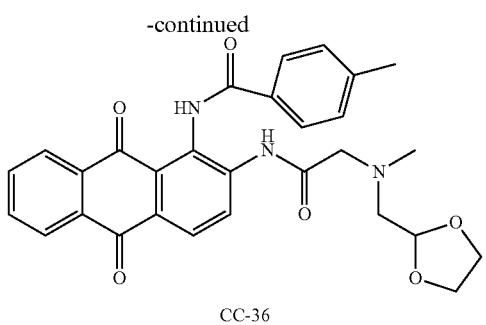

CC-36

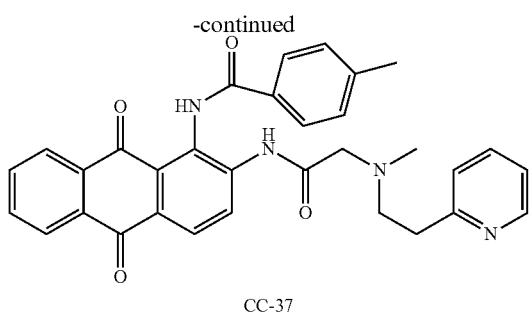

CC-37

Compound CC-12 (0.86 g, 2 mmole) was dissolved in anhydrous tetrahydrofuran (30 ml), and to the solution was added successively with DIPEA (1 ml, 6 mmole) and 2-methylaminomethyl-1,3 dioxolane (0.91 ml, 8 mmole) under stirring for 5 to 10 minutes. This mixture was heated under reflux for 16 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a kelly green compound CC-36. Mol. Wt.: 513.5412 ($C_{29}H_{27}N_3O_6$); $R_f$: 0.31 (ethyl acetate: n-hexane=1:2); Yield: 43%; Mp.: 156-157° C. (EtOH); HRMS (EI) m/z: calcd [M]$^+$, 513.1900 ($C_{29}H_{27}N_3O_6^+$). Found, 513.1902. $^1$H-NMR (300 MHz, DMSO-$d_6$) δ (ppm): 2.18 (s, 3H, —CH$_3$), 2.44 (s, 3H, —CH$_3$), 2.54 (d, J=8.7 Hz, 2H, —NCH$_2$—), 3.26 (s, 2H, —CH$_2$N—), 3.52-3.55 (m, 2H, —OCH$_2$—), 3.72-3.77 (m, 2H, —OCH$_2$—), 4.58 (t, J=4.5 Hz, 1H, —OCHO—), 7.43 (d, J=7.8 Hz, 2H, Ar—H), 7.88-7.92 (m, 2H, Ar—H), 8.04 (d, J=8.1 Hz, 2H, Ar—H), 8.10-8.19 (m, 2H, Ar—H), 8.27 (d, J=8.4 Hz, 1H, Ar—H), 8.70 (d, J=8.7 Hz, 1H, Ar—H), 10.15 (s, 1H, Ar—NH—), 10.53 (s, 1H, Ar—NH—); $^{13}$C-NMR (75 MHz, DMSO-$d_6$) δ (ppm): 20.87, 43.49, 59.43, 61.73, 63.91, 102.61, 125.50, 126.31, 126.48, 126.90, 127.89, 128.06, 129.06, 129.31, 130.75, 132.33, 134.16, 134.38, 134.45, 140.42, 142.29, 166.25 (NCO), 169.59 (NCO), 181.46 (CO), 183.70 (CO).

Example 40

4-methyl-N-(2-(2-(methyl(2-(pyridin-2-yl)ethyl)amino)acetamido)-9,10-dioxo-9,10-dihydroanthracen-1-yl)benzamide (CC-37)

Compound CC-12 (0.86 g, 2 mmole) was dissolved in anhydrous tetrahydrofuran (30 ml), and to the solution was added successively with DIPEA (1 ml, 6 mmole) and 2-(2-methylaminoethyl pyridine) (1.1 ml, 8 mmole) under stirring for 5 to 10 minutes. This mixture was heated under reflux for 16 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a glassy yellow compound CC-37. Mol. Wt.: 532.5891 ($C_{32}H_{28}N_4O_4$); $R_f$: 0.29 (ethyl acetate:n-hexane=1:2); Yield: 32%; Mp.: 166-167° C. (EtOH); HRMS (EI) m/z: calcd [M]$^+$, 532.2111 ($C_{32}H_{28}N_4O_4^+$). Found, 532.2119. $^1$H-NMR (300 MHz, DMSO-$d_6$) δ (ppm): 2.15 (s, 3H, —CH$_3$), 2.40 (s, 3H, —CH$_3$), 2.68 (d, J=7.2 Hz, 4H, —CH$_2$—), 3.20 (s, 2H, —CH$_2$N—), 7.03 (d, J=7.0 Hz, 1H, Ar—H), 7.13-7.18 (m, 1H, Ar—H), 7.39 (d, =8.1 Hz, 2H, Ar—H), 7.60-7.65 (m, 1H, Ar—H), 7.89-7.93 (m, 2H, Ar—H), 8.03 (d, J=8.1 Hz, 2H, Ar—H), 8.11-8.20 (m, 2H, Ar—H), 8.28 (d, J=8.7 Hz, 1H, Ar—H), 8.40-8.42 (m, 1H, Ar—H), 8.69 (d, J=8.7 Hz, 1H, Ar—H), 10.18 (s, 1H, Ar—NH—), 10.54 (s, 1H, Ar—NH—); $^{13}$C-NMR (75 MHz, DMSO-$d_6$) δ (ppm): 20.81, 42.45, 56.92, 61.03, 63.91, 121.62, 122.81, 125.50, 126.29, 126.44, 126.88, 127.83, 127.88, 128.07, 129.08, 129.30, 130.72, 132.33, 134.13, 134.36, 134.42, 136.24, 140.37, 142.30, 148.86, 159.40, 166.19 (NCO), 169.59 (NCO), 181.43 (CO), 183.74 (CO).

Example 41

1-(4-methylbenzamido)-2-[2-(tetrahydro-1H-1-pyrrolyl)acetylamino]-anthra quinone (CC-38)

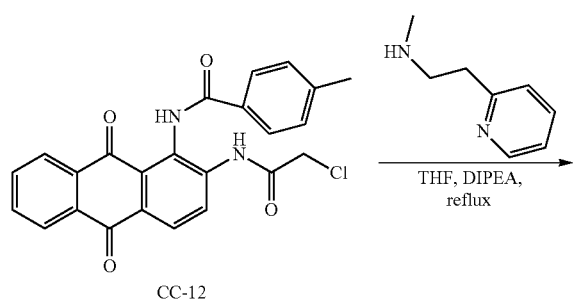

CC-12

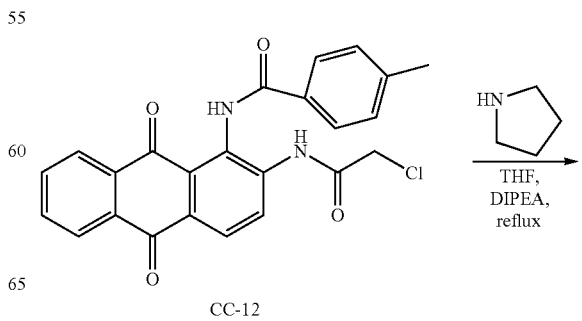

CC-12

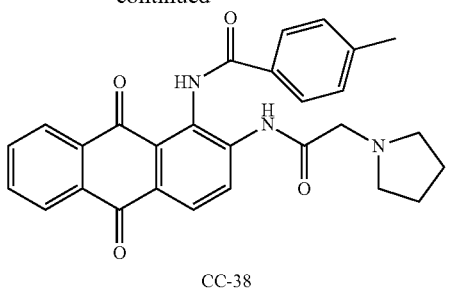

CC-38

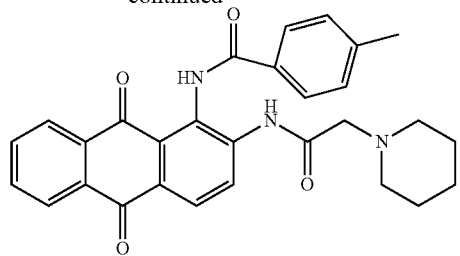

CC-39

Compound CC-12 (0.86 g, 2 mmole) was dissolved in anhydrous tetrahydrofuran (30 ml), and to the solution was added successively with DIPEA (1 ml, 6 mmole) and pyrrolidine (0.8 ml, 8 mmole) under stirring for 5 to 10 minutes. This mixture was heated under reflux for 16 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a deep brown compound CC-38. Mol. Wt.: 467.5158 ($C_{28}H_{25}N_3O_4$); 0.37 (ethyl acetate:n-hexane=1:2); Yield: 39%; Mp.: 193-194° C. (EtOH); HRMS (EI) m/z: calcd [M]$^+$, 467.1845 ($C_{28}H_{25}N_3O_4^+$). Found, 467.1840. $^1$H-NMR (300 MHz, DMSO-$d_6$) δ (ppm): 1.31 (br, 10H, —$CH_2$—), 2.43 (s, 3H, —$CH_3$), 3.27 (s, 2H, —$CH_2$N—), 7.42 (d, J=8.1 Hz, 2H, Ar—H), 7.87-7.91 (m, 2H, Ar—H), 8.09-8.19 (m, 2H, Ar—H), 8.27 (d, J=8.7 Hz, 1H, Ar—H), 8.73 (d, J=8.4 Hz, 1H, Ar—H), 10.12 (s, 1H, Ar—NH—), 10.54 (s, 1H, Ar—NH—); $^{13}$C-NMR (75 MHz, DMSO-$d_6$) δ (ppm): 20.86, 23.20, 53.65, 59.09, 126.30, 126.54, 126.88, 127.80, 127.88, 127.92, 129.05, 129.25, 130.59, 132.33, 134.12, 134.38, 134.42, 136.24, 140.44, 142.43, 166.26 (NCO), 169.56 (NCO), 181.42 (CO), 183.68 (CO).

Example 42

N-(9,10-dioxo-2-(2-(piperidin-1-yl)acetamido)-9,10-dihydroanthracen-1-yl)-4-methylbenzamide (CC-39)

Compound CC-12 (0.86 g, 2 mmole) was dissolved in anhydrous tetrahydrofuran (30 ml), and to the solution was added successively with DIPEA (1 ml, 6 mmole) and piperidine (0.79 ml, 8 mmole) under stirring for 5 to 10 minutes. This mixture was heated under reflux for 16 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a kelly green compound CC-39. Mol. Wt.: 481.5424 ($C_{29}H_{27}N_3O_4$); $R_f$: 0.36 (ethyl acetate:n-hexane=1:2); Yield: 43%; Mp.: 213-214° C. (EtOH); HRMS (EI) m/z: calcd [M]$^+$, 481.2002 ($C_{29}H_{27}N_3O_4^+$). Found, 481.2000. $^1$H-NMR (300 MHz, DMSO-$d_6$) δ (ppm): 1.08 (d, J=3.6 Hz, 2H, —$CH_2$—), 1.19 (br, 4H, —$CH_2$—), 2.33 (br, 4H, —$CH_2$—), 2.43 (s, 3H, —$CH_3$), 3.07 (s, 2H, —$CH_2$N—), 7.43 (d, J=7.8 Hz, 1H, Ar—H), 7.87-7.91 (m, 2H, Ar—H), 8.07-8.19 (m, 4H, Ar—H), 8.27 (d, J=8.7 Hz, 1H, Ar—H), 8.78 (d, J=8.7 Hz, 1H, Ar—H), 10.13 (s, 1H, Ar—NH—), 10.52 (s, 1H, Ar—NH—); $^{13}$C-NMR (75 MHz, DMSO-$d_6$) δ (ppm): 20.85, 22.80, 24.79, 54.13, 62.39, 125.19, 126.27, 126.53, 126.89, 127.84, 127.92, 128.02, 129.00, 129.22, 130.57, 132.31, 134.13, 134.36, 134.42, 140.63, 142.40, 166.25 (NCO), 169.55 (NCO), 181.42 (CO), 183.67 (CO).

Example 43

1-(4-methylbenzamido)-2-[2-(1,4-dioxa-8-azaspiro[4.5]dec-8-yl)acetylamino]-anthraquinone (CC-40)

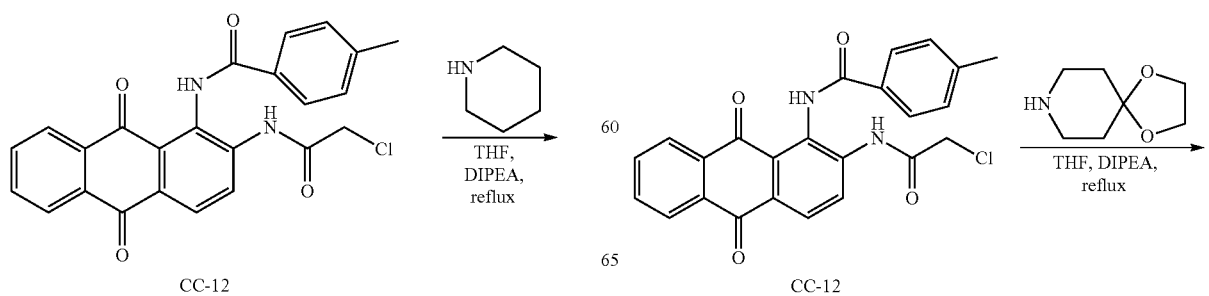

CC-12

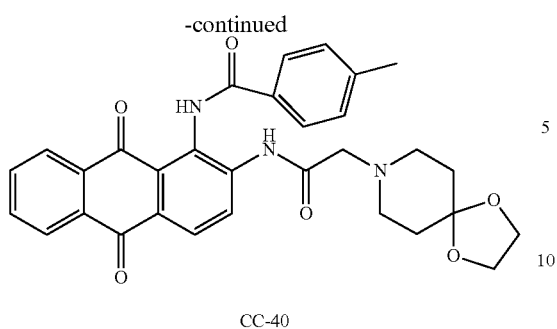

CC-40

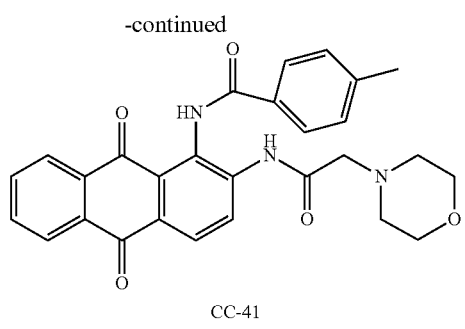

CC-41

Compound CC-12 (0.86 g, 2 mmole) was dissolved in anhydrous tetrahydrofuran (30 ml), and to the solution was added successively with DIPEA (1 ml, 6 mmole) and 1,4-dioxa-8-azaspiro[4.5]decane (1.03 ml, 8 mmole) under stirring for 5 to 10 minutes. This mixture was heated under reflux for 16 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a brown compound CC-40. Mol. Wt.: 539.5785 ($C_{31}H_{29}N_3O_6$); $R_f$: 0.34 (ethyl acetate:n-hexane=1:2); Yield: 55%; Mp.: 197-198° C. (EtOH); HRMS (EI) m/z: calcd [M]$^+$, 539.2056 ($C_{31}H_{29}N_3O_6^+$). Found, 539.2051. $^1$H-NMR (300 MHz, DMSO-d$_6$) δ (ppm): 1.39 (d, J=5.4 Hz, 8H, —CH$_2$—), 2.43 (s, 3H, —CH$_3$), 3.15 (s, 2H, —CH$_2$N—), 3.77 (s, 4H, —CH$_2$—), 7.41 (d, J=7.8 Hz, 1H, Ar—H), 7.88-7.91 (m, 2H, Ar—H), 8.06 (d, J=8.1 Hz, 2H, Ar—H), 8.10-8.19 (m, 2H, Ar—H), 8.26 (d, J=8.7 Hz, 1H, Ar—H), 8.70 (d, J=8.7 Hz, 1H, Ar—H), 10.03 (s, 1H, Ar—NH—), 10.60 (s, 1H, Ar—NH—); $^{13}$C-NMR (75 MHz, DMSO-d$_6$) δ (ppm): 20.88, 33.68, 51.35, 61.29, 63.34, 63.52, 105.58, 125.90, 126.28, 126.32, 126.91, 127.75, 127.86, 128.18, 129.18, 129.40, 130.44, 132.29, 134.13, 134.38, 134.44, 140.32, 142.46, 166.29 (NCO), 169.31 (NCO), 181.44 (CO), 183.81 (CO).

Example 44

1-(4-methylbenzamido)-2-[(2-morpholinoacetyl)amino]-anthraquinone (CC-41)

Compound CC-12 (0.86 g, 2 mmole) was dissolved in anhydrous tetrahydrofuran (30 ml), and to the solution was added successively with DIPEA (1 ml, 6 mmole) and morpholine (0.69 ml, 8 mmole) under stirring for 5 to 10 minutes. This mixture was heated under reflux for 16 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a kelly green compound CC-41. Mol. Wt.: 483.5152 ($C_{28}H_{25}N_3O_5$); $R_f$: 0.38 (ethyl acetate:n-hexane=1:2); Yield: 47%; Mp.: 225-226° C. (EtOH); HRMS (EI) m/z: calcd [M]$^+$, 483.1794 ($C_{28}H_{25}N_3O_5^+$). Found, 483.1793. $^1$H-NMR (300 MHz, DMSO-d$_6$) δ (ppm): 2.39 (br, 4H, —CH$_2$—), 2.45 (s, 3H, —CH$_3$), 3.15 (s, 2H, —CH$_2$N—), 3.22 (br, 4H, —CH$_2$—), 7.45 (d, J=7.8 Hz, 2H, Ar—H), 7.88-7.91 (m, 2H, Ar—H), 8.07-8.12 (m, 3H, Ar—H), 8.27 (d, J=8.7 Hz, 1H, Ar—H), 8.73 (d, J=8.7 Hz, 1H, Ar—H), 9.99 (s, 1H, Ar—NH—), 10.61 (s, 1H, Ar—NH—); $^{13}$C-NMR (75 MHz, DMSO-d$_6$) δ (ppm): 20.95, 53.17, 61.94, 65.59, 125.73, 126.37, 126.53, 126.98, 127.82, 128.05, 129.28, 129.46, 130.55, 132.35, 134.16, 134.53, 140.31, 142.66, 166.32 (NCO), 168.97 (NCO), 181.50 (CO), 183.84 (CO).

Example 45

1-(4-methylbenzamido)-2-[2-(1,4-thiazinan-4-yl)acetylamino]-anthraquinone (CC-42)

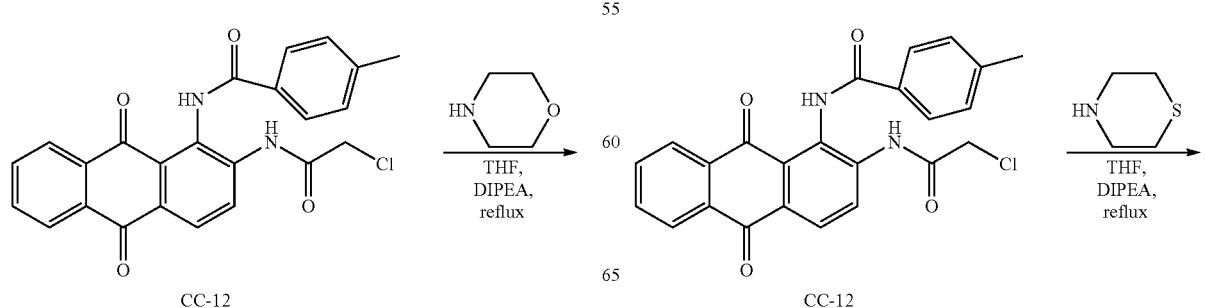

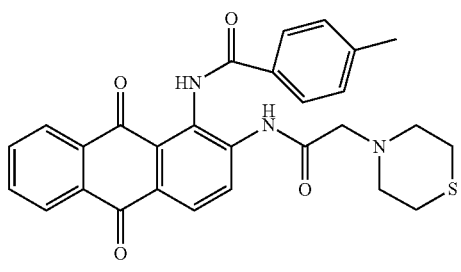

CC-42

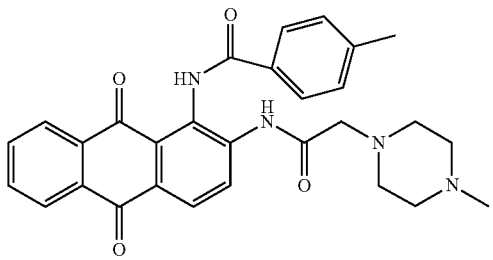

CC-43

Compound CC-12 (0.86 g, 2 mmole) was dissolved in anhydrous tetrahydrofuran (30 ml), and to the solution was added successively with DIPEA (1 ml, 6 mmole) and thiomorpholine (0.80 ml, 8 mmole) under stirring for 5 to 10 minutes. This mixture was heated under reflux for 16 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a kelly green compound CC-42. Mol. Wt.: 499.5808 ($C_{28}H_{25}N_3O_4S$); $R_f$: 0.43 (ethyl acetate:n-hexane=1:2); Yield: 51%; Mp.: 210-211° C. (EtOH); HRMS (EI) m/z: calcd [M]$^+$, 499.1566 ($C_{28}H_{25}N_3O_4S^+$). Found, 499.1570. $^1$H-NMR (300 MHz, DMSO-$d_6$) δ (ppm): 2:39 (br, 4H, —CH$_2$—), 2.45 (s, 3H, —CH$_3$), 3.15 (s, 2H, —CH$_2$N—), 3.23 (br, 4H, —CH$_2$—), 7.45 (d, J=8.1 Hz, 2H, Ar—H), 7.88-7.91 (m, 2H, Ar—H), 8.07-8.19 (m, 4H, Ar—H), 8.27 (d, J=8.4 Hz, 1H, Ar—H), 8.73 (d, J=8.4 Hz, 1H, Ar—H), 10.00 (s, 1H, Ar—NH—), 10.61 (s, 1H, Ar—NH—); $^{13}$C-NMR (75 MHz, DMSO-$d_6$) δ (ppm): 20.89, 26.48, 53.13, 54.62, 61.92, 65.54, 127.72, 126.30, 126.40, 126.92, 127.69, 127.92, 127.98, 129.22, 129.43, 130.53, 132.30, 134.12, 134.41, 134.45, 140.21, 142.61, 166.27 (NCO), 168.89, 169.15 (NCO), 181.42 (CO), 183.84 (CO).

Compound CC-12 (0.86 g, 2 mmole) was dissolved in anhydrous tetrahydrofuran (30 ml), and to the solution was added successively with DIPEA (1 ml, 6 mmole) and N-methylpiperazine (0.88 ml, 8 mmole) under stirring for 5 to 10 minutes. This mixture was heated under reflux for 16 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a kelly green compound CC-43. Mol. Wt.: 496.5570 ($C_{29}H_{28}N_4O_4$); $R_f$: 0.28 (ethyl acetate:n-hexane=1:2); Yield: 55%; Mp.: 214-215° C. (EtOH); HRMS (EI) m/z: calcd [M]$^+$, 496.2111 ($C_{29}H_{28}N_4O_4^+$). Found, 496.2115. $^1$H-NMR (300 MHz, DMSO-$d_6$) δ (ppm): 1.76 (s, 3H, —CH$_3$), 1.96 (br, 4H, —CH$_2$—), 2.38 (br, 4H, —CH$_2$—), 2.43 (s, 3H, —CH$_3$), 3.13 (s, 2H, —CH$_2$N—), 7.45 (d, J=7.8 Hz, 2H, Ar—H), 7.87-7.93 (m, 2H, Ar—H), 8.08-8.16 (m, 4H, Ar—H), 8.27 (d, J=9.0 Hz, 1H, Ar—H), 8.81 (d, J=8.7 Hz, 1H, Ar—H), 10.01 (s, 1H, Ar—NH—), 10.50 (s, 1H, Ar—NH—); $^{13}$C-NMR (75 MHz, DMSO-$d_6$) δ (ppm): 20.89, 26.48, 53.13, 54.62, 61.92, 65.54, 127.72, 126.30, 126.40, 126.92, 127.69, 127.92, 127.98, 129.22, 129.43, 130.53, 132.30, 134.12, 134.41, 134.45, 140.21, 142.61, 166.27 (NCO), 168.89, 169.15 (NCO), 181.42 (CO), 183.84 (CO).

Example 46

1-(4-methylbenzamido)-2-[2-(4-methylpiperazino)acetylamino]-anthraquinone (CC-43)

Example 47

1-(4-methylbenzamido)-2-[2-(4-(2-hydroxyethyl)piperazino]acetylamino]-anthraquinone (CC-44)

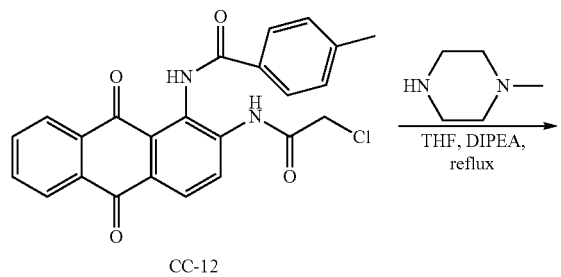

CC-12

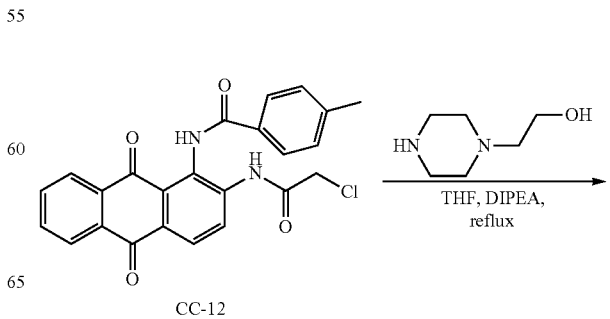

CC-12

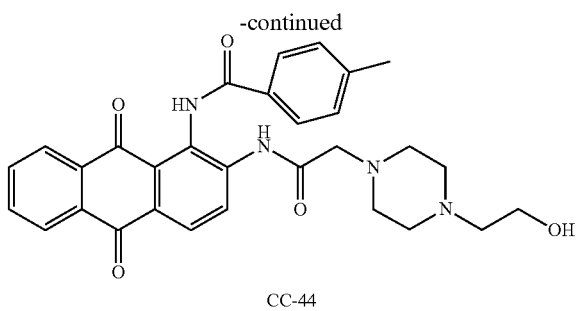

CC-44

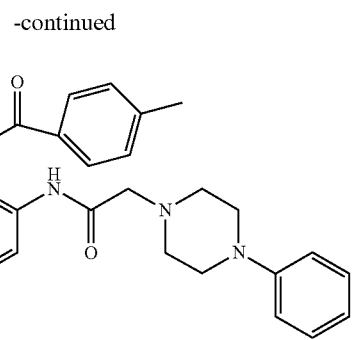

CC-45

Compound CC-12 (0.86 g, 2 mmole) was dissolved in anhydrous tetrahydrofuran (30 ml), and to the solution was added successively with DIPEA (1 ml, 6 mmole) and 2-(piperazin-1-yl)ethanol (0.97 ml, 8 mmole) under stirring for 5 to 10 minutes. This mixture was heated under reflux for 16 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a kelly green compound CC-44. Mol. Wt.: 526.5830 ($C_{30}H_{30}N_4O_5$); $R_f$: 0.41 (ethyl acetate:n-hexane=1:2); Yield: 48%; Mp.: 210-211° C. (EtOH); HRMS (EI) m/z: calcd [M]$^+$, 526.2216 ($C_{30}H_{30}N_4O_5{}^+$). Found, 526.2219. $^1$H-NMR (300 MHz, DMSO-$d_6$) δ (ppm): 1.92 (t, J=6.0 Hz, 2H, —NCH$_2$—), 2.03 (br, 4H, —CH$_2$—), 2.39 (br, 4H, —CH$_2$—), 2.43 (s, 3H, —CH$_3$), 3.01 (s, 2H, —CH$_2$N—), 3.26-3.30 (m, 2H, —CH$_2$OH), 4.29 (t, J=5.4 Hz, 1H, —CH$_2$OH), 7.43 (d, J=8.1 Hz, 2H, Ar—H), 7.87-7.91 (m, 2H, Ar—H), 8.07-8.19 (m, 4H, Ar—H), 8.27 (d, J=8.7 Hz, 1H, Ar—H), 8.79 (d, J=8.7 Hz, 1H, Ar—H), 10.00 (s, 1H, Ar—NH—), 10.50 (s, 1H, Ar—NH—); $^{13}$C-NMR (75 MHz, DMSO-$d_6$) δ (ppm): 20.93, 52.32, 52.93, 58.21, 59.1, 61.69, 125.11, 126.37, 126.72, 126.98, 127.81, 128.04, 128.33, 129.24, 130.53, 130.53, 140.68, 142.70, 166.37 (NCO), 169.28 (NCO), 181.50 (CO), 183.67 (CO).

Example 48

1-(4-methylbenzamido)-2-[2-(4-phenylpiperazino)acetylamino]-anthraquinone (CC-45)

Compound CC-12 (0.86 g, 2 mmole) was dissolved in anhydrous tetrahydrofuran (30 ml), and to the solution was added successively with DIPEA (1 ml, 6 mmole) and N-phenylpiperazine (1.22 ml, 8 mmole) under stirring for 5 to 10 minutes. This mixture was heated under reflux for 16 hours. After completion of reaction, the mixture was filtered and the crude product was isolated from the upper layer of the filtrate and recrystallized in ethanol to obtain kelly green compounds CC-45. Mol. Wt.: 558.6264 ($C_{34}H_{30}N_4O_4$); $R_f$: 0.36 (ethyl acetate:n-hexane=1:2); Yield: 53%; Mp.: 270-271° C. (EtOH); HRMS (EI) m/z: calcd [M]$^+$, 558.2267 ($C_{34}H_{30}N_4O_4{}^+$). Found, 558.2271. $^1$H-NMR (300 MHz, DMSO-$d_6$) δ (ppm): 2.21 (s, 3H, —CH$_3$), 2.55 (br, 4H, —CH$_2$—), 2.73 (br, 4H, —CH$_2$—), 3.22 (s, 2H, —CH$_2$N—), 6.64 (d, J=7.5 Hz, 2H, Ar—H), 6.79 (d, J=7.2 Hz, 1H, Ar—H), 7.12-7.21 (m, 4H, Ar—H), 7.87-7.92 (m, 2H, Ar—H), 7.98 (d, J=8.1 Hz, 2H, Ar—H), 8.08-8.19 (m, 2H, Ar—H), 8.29 (d, J=8.7 Hz, 1H, Ar—H), 8.80 (d, J=8.7 Hz, 1H, Ar—H), 10.07 (s, 1H, Ar—NH—), 10.52 (s, 1H, Ar—NH—); $^{13}$C-NMR (75 MHz, DMSO-$d_6$) δ (ppm): 20.76, 47.66, 52.81, 61.52, 115.40, 118.74, 125.16, 126.28, 126.57, 126.88, 127.84, 127.95, 128.58, 129.05, 129.27, 130.28, 134.11, 134.42, 140.51, 142.46, 150.77, 166.21 (NCO), 169.05 (NCO), 181.42 (CO), 183.65 (CO).

Example 49

1-(4-methylbenzamido)-2-[2-[4-(2-fluorophenyl)piperazino]acetylamino]-anthraquinone (CC-46)

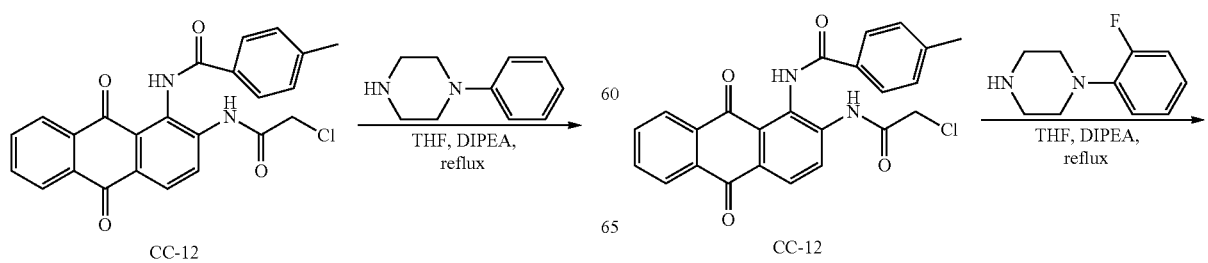

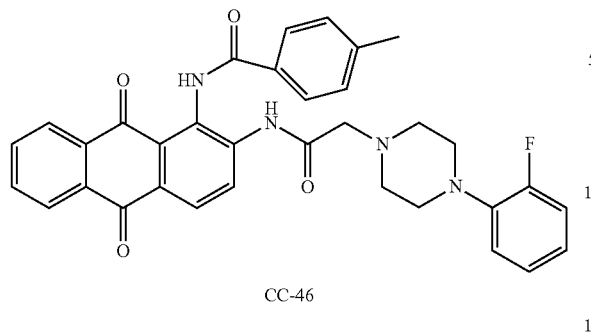

CC-46

CC-47

Compound CC-12 (0.86 g, 2 mmole) was dissolved in anhydrous tetrahydrofuran (30 ml), and to the solution was added successively with DIPEA (1 ml, 6 mmole) and 1-(2-fluorophenyl)piperazine (1.26 ml, 8 mmole) under stirring for 5 to 10 minutes. This mixture was heated under reflux for 16 hours. After completion of reaction, the mixture was filtered and the crude product was isolated from the upper layer of the filtrate and recrystallized in ethanol to obtain orangered compounds CC-46. Mol. Wt.: 576.6169 ($C_{34}H_{29}FN_4O_4^+$); $R_f$: 0.32 (ethyl acetate:n-hexane=1:2); Yield: 62%; Mp.: 228-229° C. (EtOH); HRMS (EI) m/z: calcd [M]$^+$, 576.2173 ($C_{34}H_{29}FN_4O_4^+$). Found, 576.2181. $^1$H-NMR (300 MHz, DMSO-d$_6$) δ (ppm): 2.29 (s, 3H, —CH$_3$), 2.58 (br, 8H, —CH$_2$—), 3.17 (s, 2H, —CH$_2$N—), 6.42 (t, J=7.2 Hz, 1H, Ar—H), 6.97-7.10 (m, 3H, Ar—H), 7.30 (d, J=7.5 Hz, 2H, Ar—H), 7.87-7.91 (m, 2H, Ar—H), 8.04-8.11 (m, 4H, Ar—H), 8.16-8.19 (m, 1H, Ar—H), 8.29 (d, J=8.4 Hz, 1H, Ar—H), 8.81 (d, J=8.4 Hz, 1H, Ar—H), 10.06 (s, 1H, Ar—NH—), 10.56 (s, 1H, Ar—NH—); $^{13}$C-NMR (75 MHz, DMSO-d$_6$) δ (ppm): 21.54, 50.19, 53.61, 62.30, 114.94, 116.26, 116.54, 119.71, 122.85, 122.96, 127.04, 127.33, 127.65, 128.61, 128.81, 129.97, 130.04, 131.26, 133.07, 134.86, 135.18, 141.20, 143.28, 153.96, 167.00 (NCO), 169.77 (NCO), 182.17 (CO), 184.48 (CO).

Compound CC-12 (0.86 g, 2 mmole) was dissolved in anhydrous tetrahydrofuran (30 ml), and to the solution was added successively with DIPEA (1 ml, 6 mmole) and 1-(2-cyanophenyl)piperazine (1.35 ml, 8 mmole) under stirring for 5 to 10 minutes. This mixture was heated under reflux for 16 hours. After completion of reaction, the mixture was filtered and the crude product was isolated from the upper layer of the filtrate and recrystallized in ethanol to obtain yellow compounds CC-47. Mol. Wt.: 583.6359 ($C_{35}H_{29}N_5O_4$); $R_f$:0.37 (ethyl acetate:n-hexane=1:2); Yield: 55%; Mp.: 238-239° C. (EtOH); HRMS (EI) m/z: calcd [M]$^+$, 583.2220 ($C_{35}H_{29}N_5O_4^+$). Found, 583.6359. $^1$H-NMR (300 MHz, DMSO-d$_6$) δ (ppm): 2.30 (s, 3H, —CH$_3$), 2.62 (br, 4H, —CH$_2$—), 2.71 (br, 4H, —CH$_2$—), 3.22 (s, 2H, —CH$_2$N—), 6.50 (d, J=8.4 Hz, 1H, Ar—H), 7.11 (t, J=7.5 Hz, 1H, Ar—H), 7.34 (d, J=8.1 Hz, 2H, Ar—H), 7.58 (t, J=8.4 Hz, 1H, Ar—H), 7.66 (dd, J=9.0 Hz, J=1.5 Hz, 2H, Ar—H), 7.87-7.91 (m, 2H, Ar—H), 8.06-8.19 (m, 4H, Ar—H), 8.29 (d, J=9.0 Hz, 1H, Ar—H), 8.82 (d, 0.1=8.7 Hz, 1H, Ar—H), 10.06 (s, 1H, Ar—NH—), 10.58 (s, 1H, Ar—NH—); $^{13}$C-NMR (75 MHz, DMSO-d$_6$) δ (ppm): 21.54, 50.19, 53.61, 62.30, 114.94, 116.26, 116.54, 119.71, 122.85, 122.96, 127.04, 127.33, 127.65, 128.61, 128.81, 129.97, 130.04, 131.26, 133.07, 134.86, 135.18, 141.20, 143.28, 153.96, 167.00 (NCO), 169.77 (NCO), 182.17 (CO), 184.48 (CO).

Example 50

1-(4-methylbenzamido)-2-[2-[4-(2-cyanophenyl)piperazino]acetylamino]-anthraquinone (CC-47)

Example 51

1-(4-methylbenzamido)-2-[2-[4-(2-methoxyphenyl)piperazino]acetylamino]-anthraquinone (CC-48)

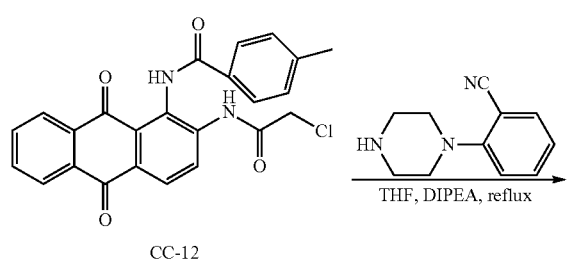

CC-12

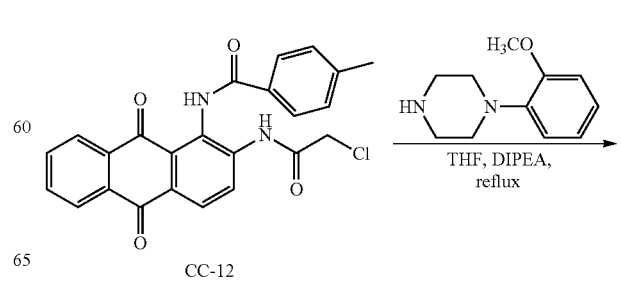

CC-12

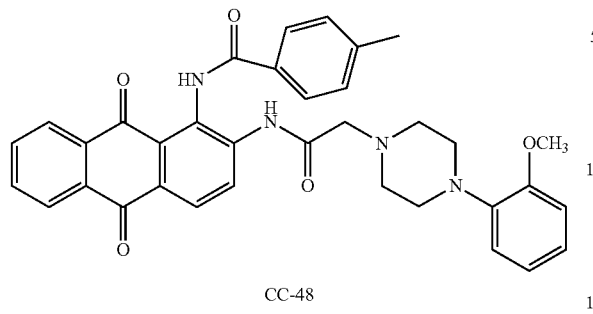

CC-48

Compound CC-12 (0.86 g, 2 mmole) was dissolved in anhydrous tetrahydrofuran (30 ml), and to the solution was added successively with DIPEA (1 ml, 6 mmole) and 1-(2-methoxyphenyl)piperazine (1.38 ml, 8 mmole) under stirring for 5 to 10 minutes. This mixture was heated under reflux for 16 hours. After completion of reaction, the mixture was filtered and the crude product was isolated from the upper layer of the filtrate and recrystallized in ethanol to obtain saffron yellow compounds CC-48. Mol. Wt.: 588.6524 ($C_{35}H_{32}N_4O_5$), $R_f$: 0.34 (ethyl acetate:n-hexane=1:2); Yield: 58%; Mp.: 215-216° C. (EtOH); HRMS (EI) m/z: calcd [M]$^+$, 588.2373 ($C_{35}H_{32}N_4O_5^+$). Found, 588.2378. $^1$H-NMR (300 MHz, DMSO-d$_6$) δ (ppm): 2.20 (s, 3H, —CH$_3$), 2.69 (br, 8H, —CH$_2$—), 3.22 (s, 2H, —CH$_2$N—), 3.72 (s, 3H, —OCH$_3$), 6.16 (t, J=2.4 Hz, 1H, Ar—H), 6.24 (d, J=8.1 Hz, 1H, Ar—H), 6.38 (d, J=9.0 Hz, 1H, Ar—H), 7.05-7.14 (m, 2H, Ar—H), 7.88-7.93 (m, 2H, Ar—H), 7.97 (d, J=8.1 Hz, 2H, Ar—H), 8.08-8.19 (m, 2H, Ar—H), 8.29 (d, J=8.7 Hz, 1H, Ar—H), 8.80 (d, J=8.7 Hz, 1H, Ar—H), 10.08 (s, 1H, Ar—NH—), 10.52 (s, 1H, Ar—NH—); $^{13}$C-NMR (125 MHz, DMSO-d$_6$) δ (ppm): 20.86, 47.63, 52.86, 54.81, 61.53, 101.53, 103.94, 108.06, 124.95, 126.32, 126.74, 126.90, 127.65, 127.97, 129.04, 129.25, 130.12, 132.26, 134.06, 134.41, 134.48, 140.55, 142.50, 153.05, 159.97, 163.71, 166.17 (NCO), 169.05 (NCO), 181.35 (CO), 183.44 (CO).

Example 52

1-(4-methylbenzamido)-2-[2-[4-(2-pyridyl)piperazino]acetylamino]-anthraquinone (CC-49)

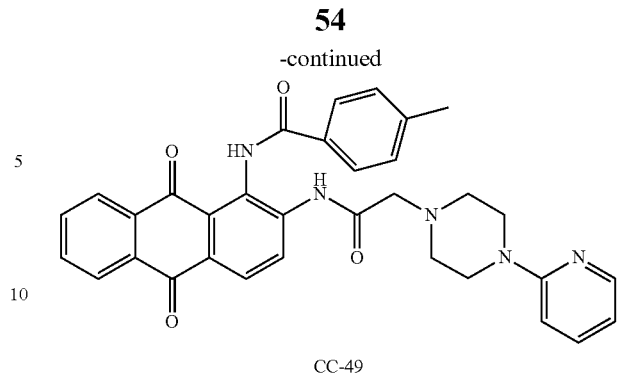

CC-49

Compound CC-12 (0.86 g, 2 mmole) was dissolved in anhydrous tetrahydrofuran (30 ml), and to the solution was added successively with DIPEA (1 ml, 6 mmole) and 1-(2-pyridyl)piperazine (1.21 ml, 8 mmole) under stirring for 5 to 10 minutes. This mixture was heated under reflux for 16 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a earth orange compound CC-49. Mol. Wt.: 559.6145 ($C_{33}H_{29}N_5O_4$); $R_f$: 0.28 (ethyl acetate:n-hexane=1: 2); Yield: 63%; Mp.: 258-259° C. (EtOH); HRMS (EI) m/z: calcd [M]$^+$, 559.2220 ($C_{33}H_{29}N_5O_4^+$). Found, 559.2224. $^1$H-NMR (300 MHz, DMSO-d$_6$) δ (ppm): 2.16 (s, 3H, —CH$_3$), 3.05 (br, 8H, —CH$_2$—), 3.22 (s, 2H, —CH$_2$N—), 6.54 (d, J=8.4 Hz, 1H, Ar—H), 6.66 (t, J=6.3 Hz, 1H, Ar—H), 7.08 (d, J=7.8 Hz, 2H, Ar—H), 7.52 (td, J=7.7 Hz, J=2.1 Hz, 1H, Ar—H), 7.87-7.91 (m, 2H, Ar—H), 7.97 (d, J=8.1 Hz, 2H, Ar—H), 8.07-8.19 (m, 2H, Ar—H), 8.29 (d, =8.7 Hz, 1H, Ar—H), 8.82 (d, J=9.0 Hz, 1H, Ar—H), 10.16 (s, 1H, Ar—NH—), 10.51 (s, 1H, Ar—NH—); $^{13}$C-NMR (75 MHz, DMSO-d$_6$) δ (ppm): 20.88, 44.21, 52.56, 61.54, 107.00, 113.11, 124.91, 126.42, 126.89, 126.99, 127.63, 128.03, 128.21, 129.01, 129.29, 132.26, 133.39, 134.19, 134.52, 134.58, 137.30, 140.73, 142.51, 147.49, 159.15, 166.26, 166.31 (NCO), 169.23 (NCO), 181.54 (CO), 183.63 (CO).

Example 53

1-(4-methylbenzamido)-2-[2-[4-(2-pyrimidinyl)piperazino]acetylamino]-anthraquinone (CC-50)

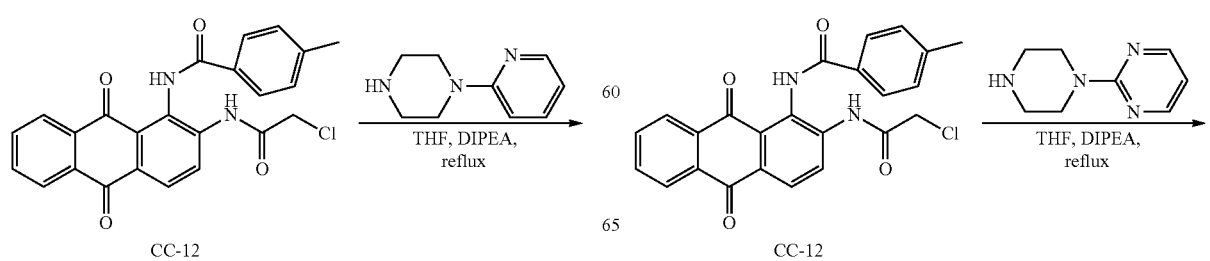

CC-12              CC-12

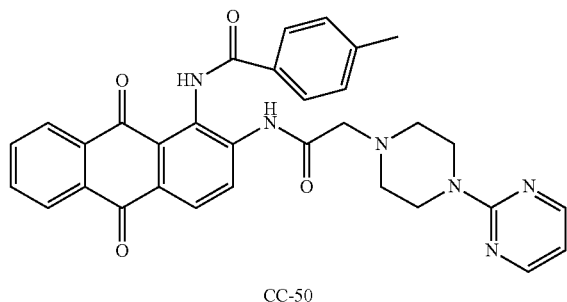

CC-50

Compound CC-12 (0.86 g, 2 mmole) was dissolved in anhydrous tetrahydrofuran (30 ml), and to the solution was added successively with DIPEA (1 ml, 6 mmole) and 1-(2-pyrimidyl)piperazine (1.13 ml, 8 mmole) under stirring for 5 to 10 minutes. This mixture was heated under reflux for 16 hours. After the completion of the reaction, the mixture was filtered, and the filtrate was concentrated by reduced pressure concentrator (such as Vacuum Evaporator). The residue was extracted with ethyl acetate for several times. The extract was dried on magnesium sulfate, and concentrated under reduced pressure. The crude product was washed with ethyl acetate/hexane. Finally, the crude product was recrystallized in hot ethanol to obtain a kelly green compound CC-50. Mol. Wt.: 560.6025 ($C_{32}H_{28}N_6O_4$), $R_f$: 0.32 (ethyl acetate:n-hexane=1:2); Yield: 41%; Mp.: 267-268° C. (EtOH); HRMS (EI) m/z: calcd [M]$^+$, 560.2172 ($C_{32}H_{28}N_6O_4^+$). Found, 560.2170. $^1$H-NMR (300 MHz, DMSO-$d_6$) δ (ppm): 2.20 (s, 3H, —CH$_3$), 3.05 (br, 8H, —CH$_2$—), 3.11 (s, 2H, —CH$_2$N—), 3.22 (br, 8H, —CH$_2$—), 6.66 (d, J=4.8 Hz, 1H, Ar—H), 7.16 (d, J=7.8 Hz, 1H, Ar—H), 7.87-7.91 (m, 2H, Ar—H), 8.01 (d, J=6.0 Hz, 2H, Ar—H), 8.08-8.19 (m, 2H, Ar—H), 8.32 (d, =7.2 Hz, 1H, Ar—H), 8.82 (d, J=8.7 Hz, 1H, Ar—H), 10.19 (s, 1H, Ar—NH—), 10.54 (s, 1H, Ar—NH—); $^{13}$C-NMR (125 MHz, DMSO-$d_6$) δ (ppm): 20.98, 42.53, 43.01, 52.46, 61.44, 110.28, 111.11, 124.77, 126.32, 126.89, 127.44, 127.92, 128.14, 128.90, 129.18, 130.18, 132.26, 134.06, 134.48, 142.39, 157.65, 158.07, 161.24, 166.12, (NCO), 169.08 (NCO), 181.35 (CO), 183.39 (CO).

Example 54

Figure 5A:
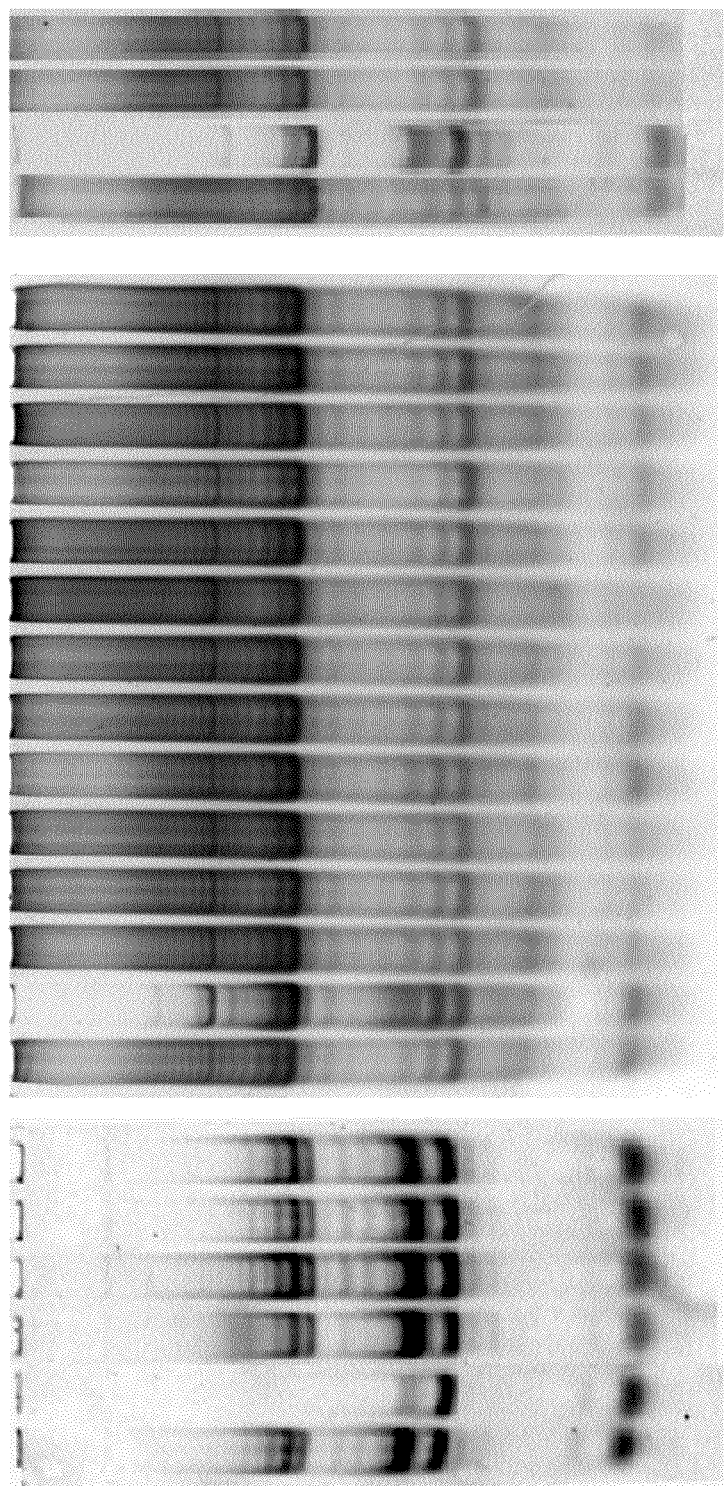
FIG. 5A depicts the result of the compound CC-01 to CC-18 in TRAP assay.
Figure 5B:
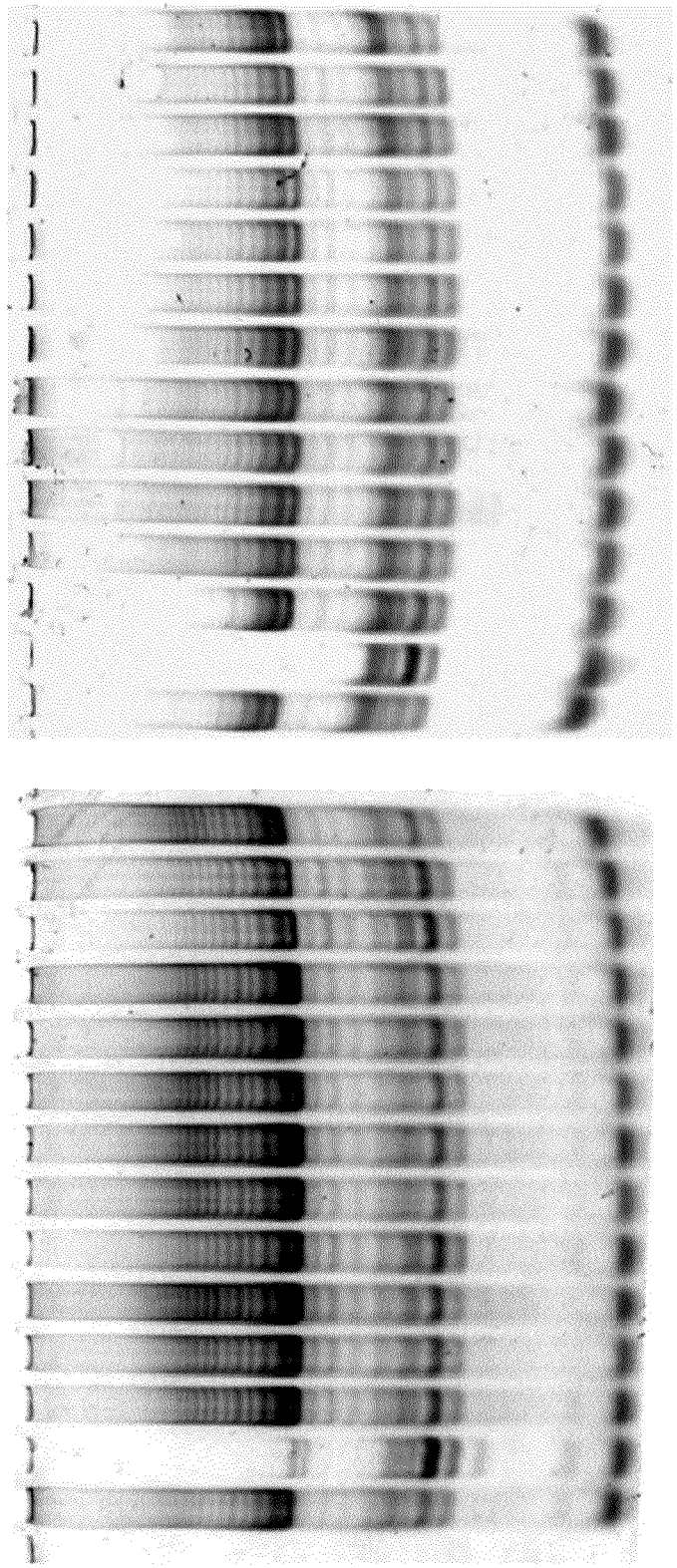
FIG. 5B depicts the result of the compound CC-19 to CC-42 in TRAP assay.
Figure 5C:
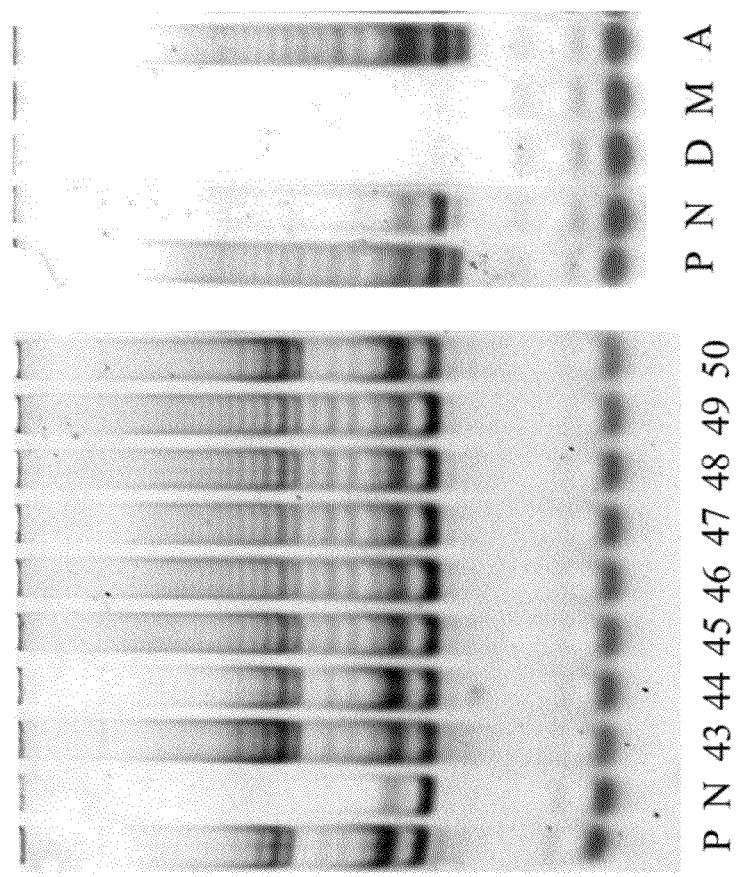
FIG. 5C depicts the result of the compound CC-43 to CC-50 in TRAP assay. P represents positive control, N represents negative control, D represents doxorubicin, M represents mitoxantrone, A represents 1,2-diaminoanthrquione.

Screening Telomerase Inhibitor by Telomere Repeat Amplification Protocol (TRAP) Assay In the FIG. 5A to 5C, a positive control group (P) was water that had been sterilized; while a negative control group (N) was 5 µl of 0.1 mg/ml RNase A (CLONTECH). It could be seen that a number of telomeric fragments were presented in the positive control group (P), while no fragments was presented in the negative control group (N). 10 µM was selected as the concentration used to screen compounds. All compounds were allowed to go through a preliminary screening. Then, more effective compounds among them were screened at different concentration. The results were shown in FIG. 5A to 5C. All of compounds CC-01 to CC-50 did not exhibit significant inhibition effect against telomerase. Therefore, it was suggested that, either symmetrically di-substituted or asymmetrically di-substituted 1,2-disubstituted amido anthraquinone derivatives exhibited poor inhibiting effect for the telomerase.

Example 55

Results of Secreted Alkaline Phosphatase Assay (SEAP Assay) and MTT Assay

Results of SEAP and MTT analysis were shown in Table 1 to 5. It indicated that compounds having symmetric (CC-01 to CC-03) or asymmetric (CC-06 to CC-08) side-chain structures exhibited better cell toxicity than 1, 2-diaminoanthraquinone at concentration of 1 µM, 10 µM, and 100 µM. Further, compounds CC-01 and CC-06 exhibited higher cell toxicity activity than mitoxantrone and doxorubicin. Most of compounds CC-09 to CC-22 exhibited very strong cell toxicity activity at high concentrations (100 µM, 10 µM). In addition, it could be found that two compounds CC-14 and CC-15 possessed very strong cell toxicity activity even at low concentration (1 µM), with a inhibitory activity even better than mitoxantrone and doxorubicin. Furthermore, among compounds CC-23 to CC-32, it could be found that the cancer cell inhibitory activity of compound CC-28 was similar with mitoxantrone and doxorubicin, even better. Compounds CC-33 to CC-50 exhibited lower cell toxicity activity at high concentrations (100 µM, 10 µM), with a significant lower cell toxicity at 10 µM. Only compounds CC-43 and CC-44 possessed higher inhibitory activity among compounds CC-35 to CC-50.

In summary, the results of SEAP and MTT assays indicated that at low concentration (1 µM), compounds CC-01, CC-06, CC-14, CC-15 and CC-28 exhibited very strong cell toxicity activity (cell survival rate lower than 50%), namely, said compounds possessed cell toxicity activity against non-small-cell lung cancer cell strain H1299, with an effect even better than mitoxantrone and doxorubicin. Compound CC-33 exhibited no significant cell toxicity both at low and high concentrations (1 µM, 10 µM, and 100 µM). Other compounds possessed cell toxic activity at high concentration (100 µM, 10 µM).

TABLE 1

Structure formula and inhibition effects on cancer cell growth of 1,2-diaminoanthrquione, Mitoxantrone, and Doxrubicin

| Compd. | Conc. (μM) | P$_{hTERT}$-SEAP (H1299) Relative SEAP activity (%) | Relative MTT viability (%) |
|---|---|---|---|
| 1,2-diaminoanthrquione | 1 | 98.55 ± 11.68 | 104.66 ± 9.37 |
| | 10 | 77.33 ± 11.57 | 95.47 ± 3.75 |
| | 100 | 18.16 ± 4.45 | 39.32 ± 8.84 |
| | DMSO | 32.23 ± 6.29 | 64.54 ± 8.32 |
| Mitoxantrone | 1 | 20.83 ± 1.56 | 23.68 ± 8.06 |
| | 10 | 9.92 ± 4.80 | −8.51 ± 1.13 |
| | 100 | 7.19 ± 1.59 | −0.44 ± 1.01 |
| | DMSO | 32.23 ± 6.29 | 64.54 ± 8.32 |
| Doxrubicin | 1 | 33.78 ± 3.22 | 17.14 ± 5.37 |
| | 10 | 13.55 ± 3.56 | −9.79 ± 2.78 |
| | 100 | 5.18 ± 4.01 | −11.38 ± 4.34 |
| | DMSO | 32.23 ± 6.29 | 56.36 ± 13.09 |

The Substituents of Formula I:

The 1,2-disubstituted amido-anthraquinone derivatives represented by general formula I of the invention:

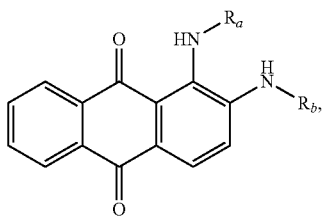

formula I wherein when $R_a$ and $R_b$ are same substituents that represented by $R_1$ in Table 2, then said 1,2-disubstituted amido-anthraquinone derivative is represented as compound CC-01, CC-02, CC-03 and CC-04;

wherein when $R_a$ represented by $R_2$ in Table 3, and $R_b$ represented by formula II:

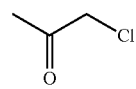

formula II, then said 1,2-disubstituted amido-anthraquinone derivative is one selected from the group consisting of compounds CC-05 to CC-32;

wherein when $R_a$ represented by formula III and $R_b$ represented by formula IV:

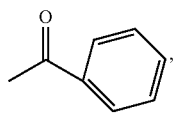

formula III

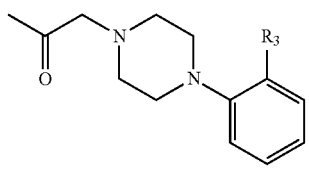

formula IV, and wherein $R_3$ is a hydrogen (H) or fluorine (F), then said 1,2-disubstituted amido-anthraquinone derivative is one selected from the group consisting of compounds CC-33 and CC-34;

wherein when $R_a$ represented by formula V and $R_b$ represented by formula VI:

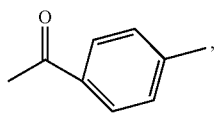

formula V

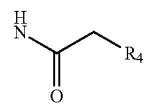

formula VI, and wherein $R_4$ is represented in Table 5, then said 1,2-disubstituted amido-anthraquinone derivative is one selected from the group consisting of compounds CC-35 to CC-50.

TABLE 2

Substituent and inhibition effects on cancer cell growth of compounds CC-01-CC-04

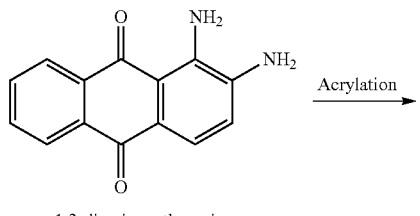

1,2-diaminoanthraquinone

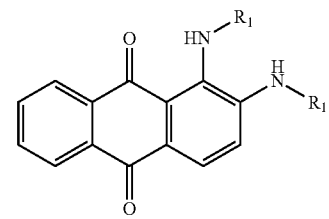

CC-01~CC-04

| Compd. | —$R_1$ | Conc. (μM) | $P_{hTERT}$-SEAP (H1299) Relative SEAP activity (%) | Relative MTT viability (%) |
|---|---|---|---|---|
| CC-01 |  | 1<br>10<br>100<br>DMSO | 15.88 ± 1.06<br>13.70 ± 1.41<br>13.70 ± 1.95<br>89.78 ± 2.59 | 8.10 ± 3.87<br>−4.79 ± 3.99<br>−6.27 ± 4.51<br>72.26 ± 7.45 |
| CC-02 |  | 1<br>10<br>100<br>DMSO | 96.26 ± 3.31<br>94.74 ± 5.06<br>15.96 ± 1.67<br>89.78 ± 2.59 | 101.18 ± 4.37<br>83.80 ± 6.94<br>5.38 ± 1.84<br>72.26 ± 7.45 |
| CC-03 | 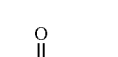 | 1<br>10<br>100<br>DMSO | 113.98 ± 6.14<br>92.87 ± 6.91<br>15.24 ± 1.13<br>89.78 ± 2.59 | 103.13 ± 7.01<br>79.89 ± 6.74<br>19.04 ± 5.31<br>72.26 ± 7.45 |
| CC-04 | 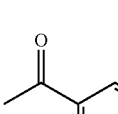 | 1<br>10<br>100<br>DMSO | 108.29 ± 9.03<br>97.13 ± 4.81<br>30.91 ± 2.54<br>89.78 ± 2.59 | 100.40 ± 4.40<br>116.64 ± 4.27<br>62.03 ± 5.40<br>72.26 ± 7.45 |

TABLE 3

Substituent and inhibition effects on cancer cell growth of compounds CC-05 to CC-32.

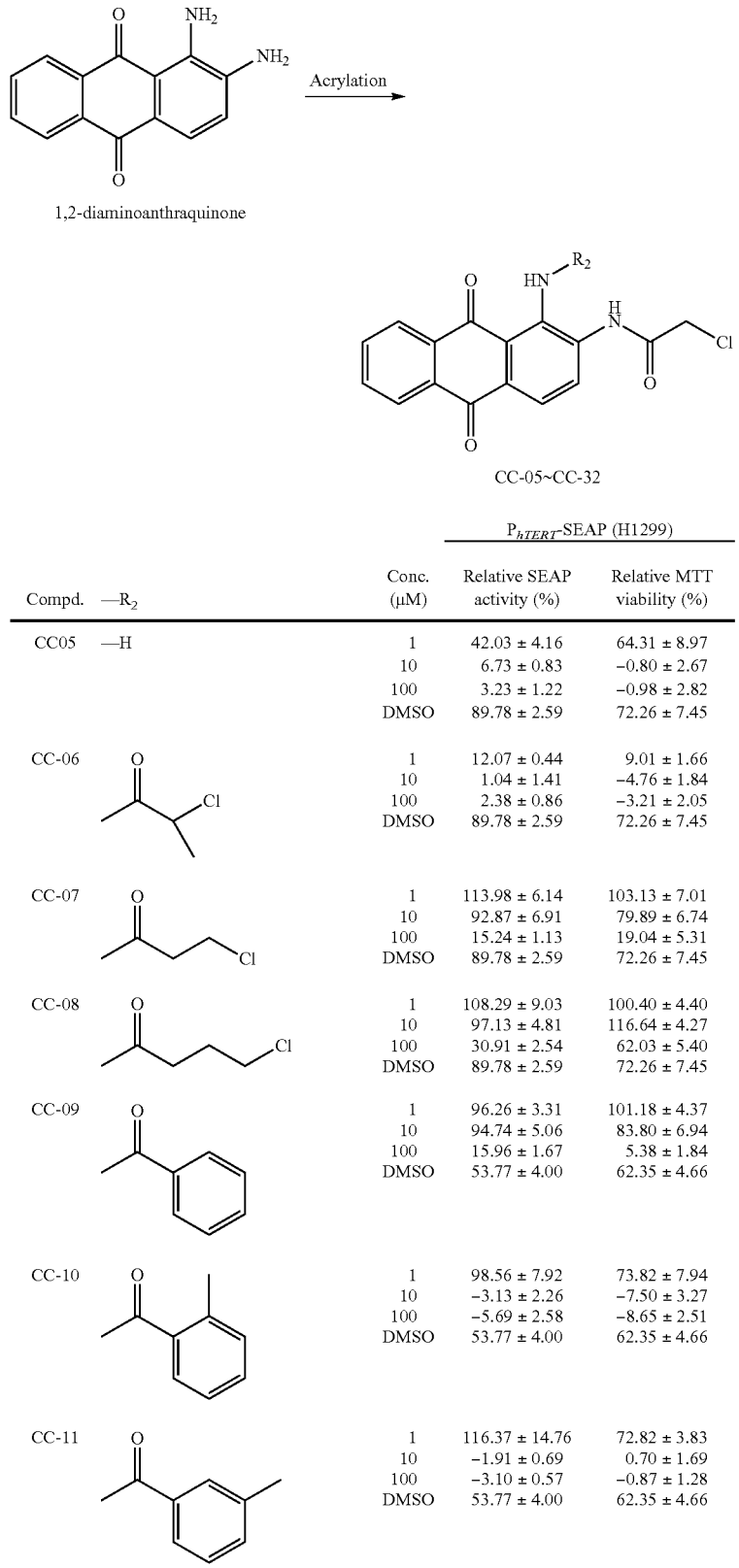

CC-05~CC-32

| Compd. | —$R_2$ | Conc. (μM) | $P_{hTERT}$-SEAP (H1299) Relative SEAP activity (%) | Relative MTT viability (%) |
|---|---|---|---|---|
| CC05 | —H | 1 | 42.03 ± 4.16 | 64.31 ± 8.97 |
| | | 10 | 6.73 ± 0.83 | −0.80 ± 2.67 |
| | | 100 | 3.23 ± 1.22 | −0.98 ± 2.82 |
| | | DMSO | 89.78 ± 2.59 | 72.26 ± 7.45 |
| CC-06 | (C(O)CH(CH₃)Cl) | 1 | 12.07 ± 0.44 | 9.01 ± 1.66 |
| | | 10 | 1.04 ± 1.41 | −4.76 ± 1.84 |
| | | 100 | 2.38 ± 0.86 | −3.21 ± 2.05 |
| | | DMSO | 89.78 ± 2.59 | 72.26 ± 7.45 |
| CC-07 | (C(O)CH₂CH₂Cl) | 1 | 113.98 ± 6.14 | 103.13 ± 7.01 |
| | | 10 | 92.87 ± 6.91 | 79.89 ± 6.74 |
| | | 100 | 15.24 ± 1.13 | 19.04 ± 5.31 |
| | | DMSO | 89.78 ± 2.59 | 72.26 ± 7.45 |
| CC-08 | (C(O)CH₂CH₂CH₂Cl) | 1 | 108.29 ± 9.03 | 100.40 ± 4.40 |
| | | 10 | 97.13 ± 4.81 | 116.64 ± 4.27 |
| | | 100 | 30.91 ± 2.54 | 62.03 ± 5.40 |
| | | DMSO | 89.78 ± 2.59 | 72.26 ± 7.45 |
| CC-09 | (C(O)Ph) | 1 | 96.26 ± 3.31 | 101.18 ± 4.37 |
| | | 10 | 94.74 ± 5.06 | 83.80 ± 6.94 |
| | | 100 | 15.96 ± 1.67 | 5.38 ± 1.84 |
| | | DMSO | 53.77 ± 4.00 | 62.35 ± 4.66 |
| CC-10 | (C(O)-2-MePh) | 1 | 98.56 ± 7.92 | 73.82 ± 7.94 |
| | | 10 | −3.13 ± 2.26 | −7.50 ± 3.27 |
| | | 100 | −5.69 ± 2.58 | −8.65 ± 2.51 |
| | | DMSO | 53.77 ± 4.00 | 62.35 ± 4.66 |
| CC-11 | (C(O)-3-MePh) | 1 | 116.37 ± 14.76 | 72.82 ± 3.83 |
| | | 10 | −1.91 ± 0.69 | 0.70 ± 1.69 |
| | | 100 | −3.10 ± 0.57 | −0.87 ± 1.28 |
| | | DMSO | 53.77 ± 4.00 | 62.35 ± 4.66 |

TABLE 3-continued

Substituent and inhibition effects on cancer cell growth of compounds CC-05 to CC-32.

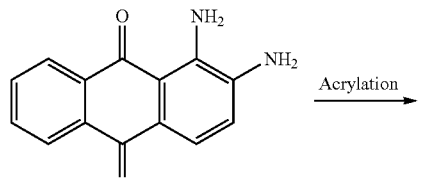

1,2-diaminoanthraquinone

Acrylation →

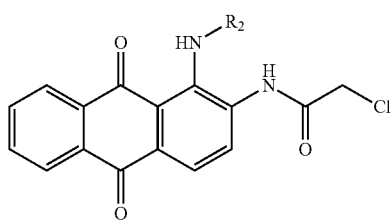

CC-05~CC-32

| Compd. | —R$_2$ | Conc. (μM) | P$_{hTERT}$-SEAP (H1299) | |
|---|---|---|---|---|
| | | | Relative SEAP activity (%) | Relative MTT viability (%) |
| CC-12 | (4-methylphenyl ketone) | 1<br>10<br>100<br>DMSO | 109.72 ± 2.99<br>−2.49 ± 0.92<br>−2.47 ± 0.48<br>53.77 ± 4.00 | 103.69 ± 7.83<br>2.77 ± 0.62<br>−0.09 ± 1.02<br>62.35 ± 4.66 |
| CC-13 | (2-fluorophenyl ketone) | 1<br>10<br>100<br>DMSO | 105.28 ± 12.67<br>5.89 ± 0.83<br>2.11 ± 0.49<br>44.93 ± 26.45 | 78.77 ± 7.83<br>2.77 ± 0.62<br>−0.09 ± 1.02<br>62.35 ± 4.66 |
| CC-14 | (3-fluorophenyl ketone) | 1<br>10<br>100<br>DMSO | 26.85 ± 11.59<br>1.77 ± 0.41<br>0.97 ± 0.46<br>44.93 ± 26.45 | 18.33 ± 13.54<br>8.06 ± 1.30<br>−1.59 ± 0.25<br>67.86 ± 6.20 |
| CC-15 | (4-fluorophenyl ketone) | 1<br>10<br>100<br>DMSO | 11.88 ± 9.77<br>2.58 ± 3.08<br>0.52 ± 2.33<br>44.93 ± 26.45 | 10.89 ± 2.92<br>4.20 ± 0.92<br>−3.13 ± 0.20<br>67.86 ± 6.20 |
| CC-16 | (2-chlorophenyl ketone) | 1<br>10<br>100<br>DMSO | 81.57 ± 48.25<br>5.35 ± 2.83<br>1.23 ± 2.17<br>44.93 ± 26.45 | 101.74 ± 4.26<br>6.63 ± 1.07<br>−2.09 ± 0.20<br>67.86 ± 6.20 |
| CC-17 | (3-chlorophenyl ketone) | 1<br>10<br>100<br>DMSO | 80.92 ± 3.90<br>6.65 ± 0.47<br>3.51 ± 0.57<br>44.47 ± 5.37 | 89.69 ± 2.74<br>5.08 ± 0.85<br>−4.31 ± 0.41<br>66.98 ± 2.44 |

TABLE 3-continued

Substituent and inhibition effects on cancer cell growth of compounds CC-05 to CC-32.

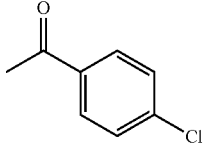

1,2-diaminoanthraquinone

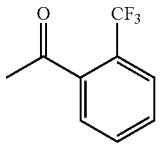

CC-05~CC-32

| Compd. | —R$_2$ | Conc. (μM) | P$_{hTERT}$-SEAP (H1299) Relative SEAP activity (%) | Relative MTT viability (%) |
|---|---|---|---|---|
| CC-18 | 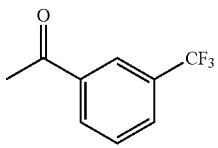 | 1<br>10<br>100<br>DMSO | 98.69 ± 5.60<br>6.26 ± 0.54<br>4.95 ± 0.47<br>44.47 ± 5.37 | 92.36 ± 7.16<br>5.17 ± 1.14<br>4.25 ± 0.41<br>66.98 ± 2.44 |
| CC-19 | 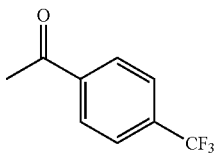 | 1<br>10<br>100<br>DMSO | 93.45 ± 6.11<br>4.89 ± 1.29<br>2.40 ± 0.63<br>44.47 ± 5.37 | 93.20 ± 2.95<br>3.42 ± 1.92<br>−4.30 ± 0.46<br>66.98 ± 2.44 |
| CC-20 | | 1<br>10<br>100<br>DMSO | 99.77 ± 4.15<br>4.53 ± 0.66<br>0.32 ± 1.26<br>44.47 ± 5.37 | 94.73 ± 3.59<br>5.15 ± 1.03<br>3.37 ± 1.01<br>66.98 ± 2.44 |
| CC-21 | | 1<br>10<br>100<br>DMSO | 85.93 ± 8.00<br>8.61 ± 0.61<br>6.49 ± 0.49<br>47.78 ± 3.60 | 86.27 ± 2.60<br>6.58 ± 0.92<br>−1.40 ± 0.31<br>61.60 ± 2.38 |
| CC-22 | 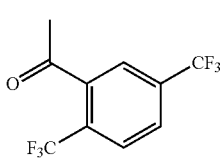 | 1<br>10<br>100<br>DMSO | 90.34 ± 1.77<br>5.11 ± 0.16<br>4.11 ± 0.40<br>47.78 ± 3.60 | 86.72 ± 2.13<br>8.81 ± 1.41<br>−0.92 ± 0.34<br>61.60 ± 2.38 |
| CC-23 | 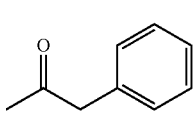 | 1<br>10<br>100<br>DMSO | 84.77 ± 3.12<br>9.49 ± 0.83<br>7.43 ± 0.61<br>47.78 ± 3.60 | 81.99 ± 1.79<br>5.94 ± 1.80<br>3.98 ± 1.00<br>61.60 ± 2.38 |

TABLE 3-continued
Substituent and inhibition effects on cancer cell growth of compounds CC-05 to CC-32.
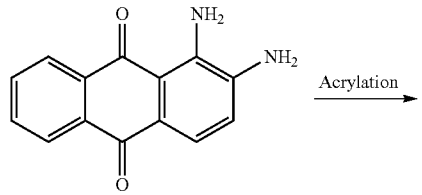
1,2-diaminoanthraquinone
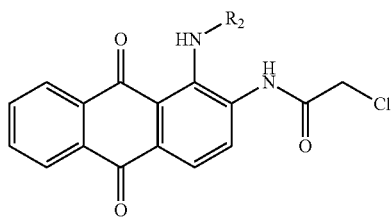
CC-05~CC-32
| Compd. | —R$_2$ | Conc. (μM) | P$_{hTERT}$-SEAP (H1299) | |
|---|---|---|---|---|
| | | | Relative SEAP activity (%) | Relative MTT viability (%) |
| CC-24 | | 1 | 93.11 ± 5.96 | 88.90 ± 5.07 |
| | | 10 | 8.40 ± 0.80 | 7.31 ± 0.53 |
| | | 100 | 1.75 ± 0.26 | 6.17 ± 0.68 |
| | | DMSO | 47.78 ± 3.60 | 61.60 ± 2.38 |
| CC-25 | | 1 | 83.77 ± 2.67 | 88.74 ± 3.92 |
| | | 10 | 3.46 ± 0.47 | −1.34 ± 0.74 |
| | | 100 | 1.38 ± 0.51 | −4.34 ± 0.75 |
| | | DMSO | 46.16 ± 3.11 | 65.23 ± 5.62 |
| CC-26 | | 1 | 82.49 ± 4.53 | 82.28 ± 4.40 |
| | | 10 | 3.07 ± 0.79 | 1.54 ± 0.62 |
| | | 100 | 1.76 ± 0.57 | −2.25 ± 0.61 |
| | | DMSO | 46.16 ± 3.11 | 65.23 ± 5.62 |
| CC-27 | | 1 | 84.73 ± 23.31 | 80.40 ± 3.56 |
| | | 10 | 2.94 ± 0.77 | −0.58 ± 0.21 |
| | | 100 | 2.62 ± 0.44 | −2.22 ± 0.32 |
| | | DMSO | 46.16 ± 3.11 | 65.23 ± 5.62 |
| CC-28 | | 1 | 5.81 ± 23.31 | −0.01 ± 0.91 |
| | | 10 | 3.03 ± 0.52 | −2.12 ± 0.60 |
| | | 100 | 2.20 ± 0.20 | −2.22 ± 0.46 |
| | | DMSO | 46.16 ± 3.11 | 65.23 ± 5.62 |

TABLE 3-continued

Substituent and inhibition effects on cancer cell growth of compounds CC-05 to CC-32.

1,2-diaminoanthraquinone → Acrylation → CC-05~CC-32

| Compd. | —R₂ | Conc. (μM) | P$_{hTERT}$-SEAP (H1299) Relative SEAP activity (%) | Relative MTT viability (%) |
|---|---|---|---|---|
| CC-29 | (5-acetylisoxazole) | 1 | 92.48 ± 0.99 | 105.04 ± 7.19 |
|  |  | 10 | 4.91 ± 0.39 | 3.47 ± 0.35 |
|  |  | 100 | 1.35 ± 0.49 | 0.11 ± 1.58 |
|  |  | DMSO | 54.56 ± 5.79 | 73.64 ± 4.37 |
| CC-30 | (acetyl-methylfuran) | 1 | 81.25 ± 1.85 | 96.03 ± 2.27 |
|  |  | 10 | 2.37 ± 0.54 | 2.93 ± 0.83 |
|  |  | 100 | 0.83 ± 0.40 | −2.46 ± 0.64 |
|  |  | DMSO | 54.56 ± 5.79 | 73.64 ± 4.37 |
| CC-31 | (phenoxyacetyl) | 1 | 82.96 ± 1.98 | 101.00 ± 4.91 |
|  |  | 10 | 72.86 ± 2.77 | 66.52 ± 1.59 |
|  |  | 100 | 4.70 ± 0.36 | 4.86 ± 0.88 |
|  |  | DMSO | 54.56 ± 5.79 | 73.64 ± 4.37 |
| CC-32 | (phenylthioacetyl) | 1 | 80.01 ± 4.39 | 88.54 ± 2.25 |
|  |  | 10 | 3.89 ± 0.43 | 5.73 ± 0.80 |
|  |  | 100 | −0.05 ± 0.29 | −0.08 ± 0.34 |
|  |  | DMSO | 54.56 ± 5.79 | 73.64 ± 4.37 |

TABLE 4

Substituent and inhibition effects on cancer cell growth of compounds CC-33 and CC-34.

CC-09 + piperazinyl-phenyl(R₃) → CC-33~CC-34

| Compd. | —R₃ | Conc. (μM) | P$_{hTERT}$-SEAP (H1299) Relative SEAP activity (%) | Relative MTT viability (%) |
|---|---|---|---|---|
| CC-33 | —H | 1 | 85.93 ± 8.01 | 86.27 ± 2.60 |
|  |  | 10 | 97.94 ± 4.82 | 109.92 ± 8.53 |

TABLE 4-continued

| | | | | |
|---|---|---|---|---|
| | | 100 | 89.57 ± 3.37 | 87.95 ± 6.32 |
| | | DMSO | 18.60 ± 0.87 | 23.09 ± 1.91 |
| CC-34 | —F | 1 | 98.72 ± 2.55 | 98.58 ± 2.29 |
| | | 10 | 79.62 ± 1.35 | 92.28 ± 2.41 |
| | | 100 | 15.56 ± 1.54 | 27.83 ± 4.82 |
| | | DMSO | 74.30 ± 2.43 | 51.65 ± 2.26 |

TABLE 5

Substituent and inhibition effects on cancer cell growth of compounds CC-35 to CC-50.

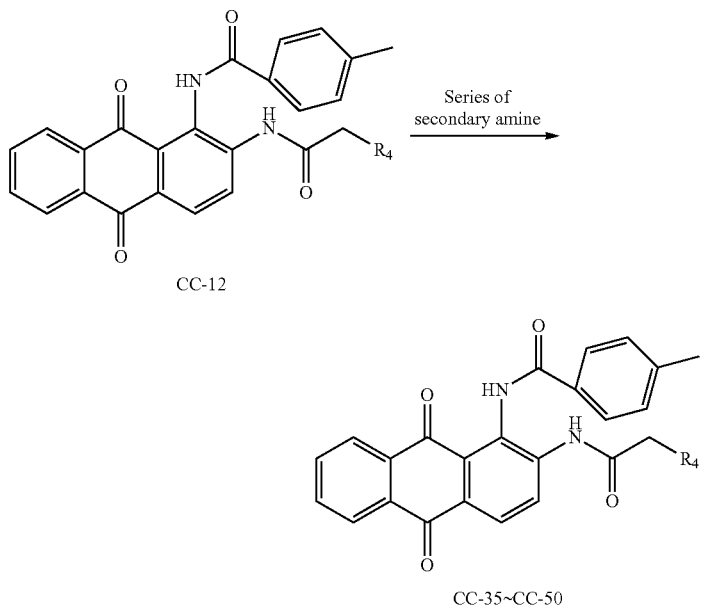

CC-12

CC-35~CC-50

| Compd. | —R$_4$ | Conc. (μM) | P$_{hTERT}$-SEAP (H1299) Relative SEAP activity (%) | Relative MTT viability (%) |
|---|---|---|---|---|
| CC-35 | N(CH$_3$)$_2$ | 1 | 99.53 ± 3.37 | 106.60 ± 2.85 |
| | | 10 | 78.51 ± 3.73 | 88.40 ± 5.93 |
| | | 100 | 9.61 ± 1.80 | −2.09 ± 0.42 |
| | | DMSO | 74.30 ± 2.43 | 51.65 ± 2.26 |
| CC-36 | N-methyl-1,3-dioxolan-2-ylmethyl | 1 | 100.85 ± 3.01 | 104.31 ± 2.12 |
| | | 10 | 76.49 ± 7.37 | 88.64 ± 7.31 |
| | | 100 | 10.18 ± 0.56 | 3.78 ± 0.80 |
| | | DMSO | 74.30 ± 2.43 | 51.65 ± 2.26 |
| CC-37 | N-methyl-2-(pyridin-2-yl)ethyl | 1 | 90.63 ± 1.48 | 94.86 ± 6.49 |
| | | 10 | 11.90 ± 2.55 | 46.25 ± 1.88 |
| | | 100 | 1.47 ± 1.35 | 22.00 ± 2.30 |
| | | DMSO | 33.64 ± 2.36 | 57.02 ± 3.67 |
| CC-38 | pyrrolidin-1-yl | 1 | 81.66 ± 4.80 | 88.15 ± 4.94 |
| | | 10 | 59.08 ± 2.42 | 69.02 ± 3.48 |
| | | 100 | 3.93 ± 0.65 | 5.05 ± 1.26 |
| | | DMSO | 33.64 ± 2.36 | 57.02 ± 3.67 |
| CC-39 | piperidin-1-yl | 1 | 85.41 ± 7.56 | 86.34 ± 6.52 |
| | | 10 | 70.14 ± 3.48 | 70.24 ± 2.98 |
| | | 100 | 8.30 ± 0.83 | 10.75 ± 2.62 |
| | | DMSO | 33.64 ± 2.36 | 57.02 ± 3.67 |
| CC-40 | 1,4-dioxa-8-azaspiro[4.5]dec-8-yl | 1 | 78.86 ± 3.67 | 74.31 ± 6.15 |
| | | 10 | 51.61 ± 5.06 | 55.55 ± 8.86 |
| | | 100 | 6.67 ± 0.99 | 16.75 ± 3.01 |
| | | DMSO | 33.64 ± 2.36 | 57.02 ± 3.67 |

TABLE 5-continued

| | | | | |
|---|---|---|---|---|
| CC-41 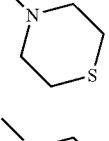 | | 1<br>10<br>100<br>DMSO | 98.37 ± 0.90<br>54.23 ± 3.69<br>3.75 ± 0.92<br>34.16 ± 9.78 | 81.55 ± 6.24<br>56.71 ± 5.24<br>15.50 ± 3.37<br>72.02 ± 6.50 |
| CC-42 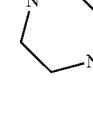 | | 1<br>10<br>100<br>DMSO | 88.00 ± 1.20<br>72.59 ± 3.12<br>12.21 ± 1.38<br>34.16 ± 9.78 | 85.81 ± 7.69<br>69.97 ± 3.69<br>20.02 ± 2.03<br>72.02 ± 6.50 |
| CC-43 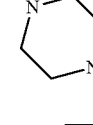 | | 1<br>10<br>100<br>DMSO | 77.43 ± 1.50<br>13.43 ± 4.92<br>3.15 ± 3.09<br>34.16 ± 9.78 | 78.75 ± 3.47<br>29.47 ± 7.97<br>8.11 ± 4.32<br>72.02 ± 6.50 |
| CC-44 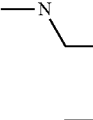 | | 1<br>10<br>100<br>DMSO | 76.99 ± 9.13<br>8.09 ± 3.61<br>−1.24 ± 0.89<br>34.16 ± 9.78 | 71.51 ± 5.12<br>44.78 ± 4.11<br>−3.84 ± 1.66<br>72.02 ± 6.50 |
| CC-45 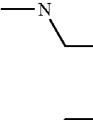 | | 1<br>10<br>100<br>DMSO | 93.21 ± 4.68<br>88.25 ± 9.64<br>15.95 ± 1.36<br>53.34 ± 4.06 | 80.80 ± 6.98<br>76.97 ± 7.98<br>23.19 ± 3.61<br>78.41 ± 0.73 |
| CC-46 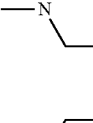 | | 1<br>10<br>100<br>DMSO | 85.04 ± 10.83<br>76.24 ± 6.66<br>20.10 ± 3.21<br>53.34 ± 4.06 | 79.83 ± 9.65<br>68.66 ± 13.38<br>40.83 ± 7.90<br>78.41 ± 0.73 |
| CC-47 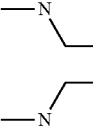 | | 1<br>10<br>100<br>DMSO | 80.95 ± 9.56<br>74.25 ± 1.35<br>20.75 ± 6.96<br>53.34 ± 4.06 | 72.04 ± 11.06<br>60.06 ± 4.35<br>48.23 ± 5.01<br>78.41 ± 0.73 |
| CC-48 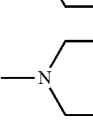 | | 1<br>10<br>100<br>DMSO | 83.34 ± 2.81<br>68.34 ± 7.39<br>12.25 ± 3.87<br>53.34 ± 4.06 | 76.36 ± 3.95<br>78.32 ± 6.62<br>22.72 ± 6.57<br>78.41 ± 0.73 |
| CC-49  | | 1<br>10<br>100<br>DMSO | 97.08 ± 7.43<br>64.30 ± 6.23<br>9.96 ± 2.44<br>32.23 ± 6.29 | 105.03 ± 3.65<br>100.14 ± 7.74<br>6.46 ± 9.47<br>64.54 ± 8.32 |
| CC-50 | | 1<br>10<br>100<br>DMSO | 87.09 ± 7.97<br>79.46 ± 3.50<br>19.99 ± 5.94<br>32.22 ± 6.29 | 102.41 ± 5.76<br>91.46 ± 5.77<br>59.00 ± 13.26<br>64.54 ± 8.32 |

Example 56

The Cytotoxicity Result of National Cancer Institute's Anticancer Drug Screen The screening system in United State National Cancer Institute (NCI) is consisted of 60 kinds of different human cancer cells, which can be used to assay the growth-inhibiting ability or cell toxicity of a compound against various cancer and tumor at a certain concentration.

Figure 6:
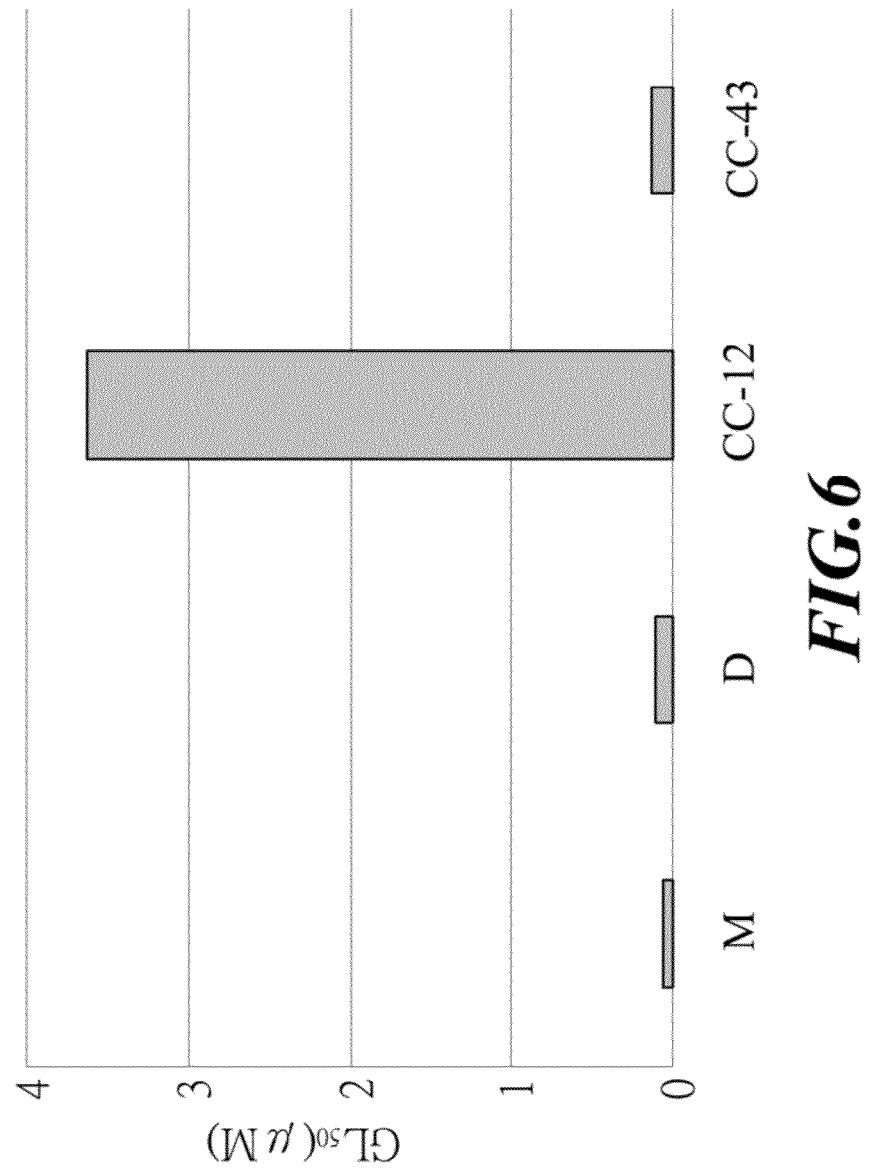
FIG. 6 depicts the concentration that causes 50% growth inhibition ($GI_{50}$) of the compound CC-12, CC-43, mitoxantrone (M) and doxorubicin (D).

Compounds CC-04, CC-12, CC-23, CC-38, and CC-43 were listed as test compounds (Table 6) in the NCI's screen. Results were shown in Table 7. Among these compounds, compound CC-12 exhibited growth-inhibiting effect against cancer cells such as leukemia, non-small cell lung cancer, colon cancer, central nervous system (CNS) cancer, melanoma, ovarian cancer, renal cancer, prostate cancer, breast cancer and the like. Compound CC-23 could inhibit the cancer cell growth of leukemia and melanoma. Compound CC-43 could inhibit the cancer cell growth of leukemia, melanoma, and ovarian cancer. In addition, in the assay against human multiple drug-resistant breast cancer cell NCI/ADR-RES (derived from ovarian cancer), compounds CC-12, CC-23 and CC-43 possessed drug-resistance against adriamycin (ADR). Under comparison the result of compounds CC-12 and CC-43 with mitoxantrone and doxorubicin in NCI database, it could be even found that the 50%-growth-inhibitory ability or 50% net growth inhibition ($GI_{50}$) of compound CC-43 (0.13 μM) was equivalent to that of doxorubicin (0.11 μM) (FIG. 6).

TABLE 6

The list of tested compounds in NCI's screen (One Dose Mean Graph)

Figure 7:
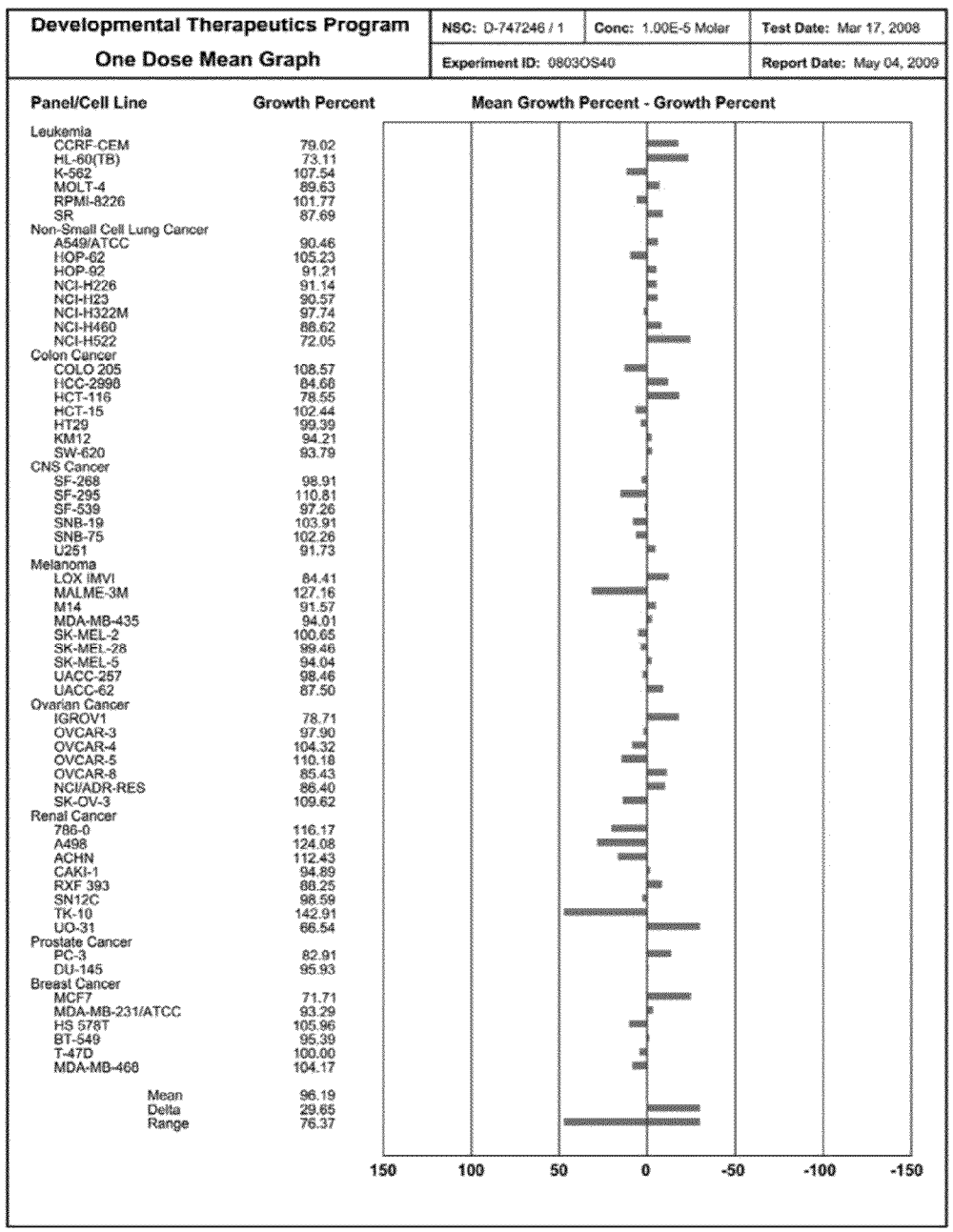
FIG. 7 to FIG. 11 depict the NCI result of compounds CC-04, CC-12, CC-23, CC-38 and CC-43, respectively.
Figure 8:
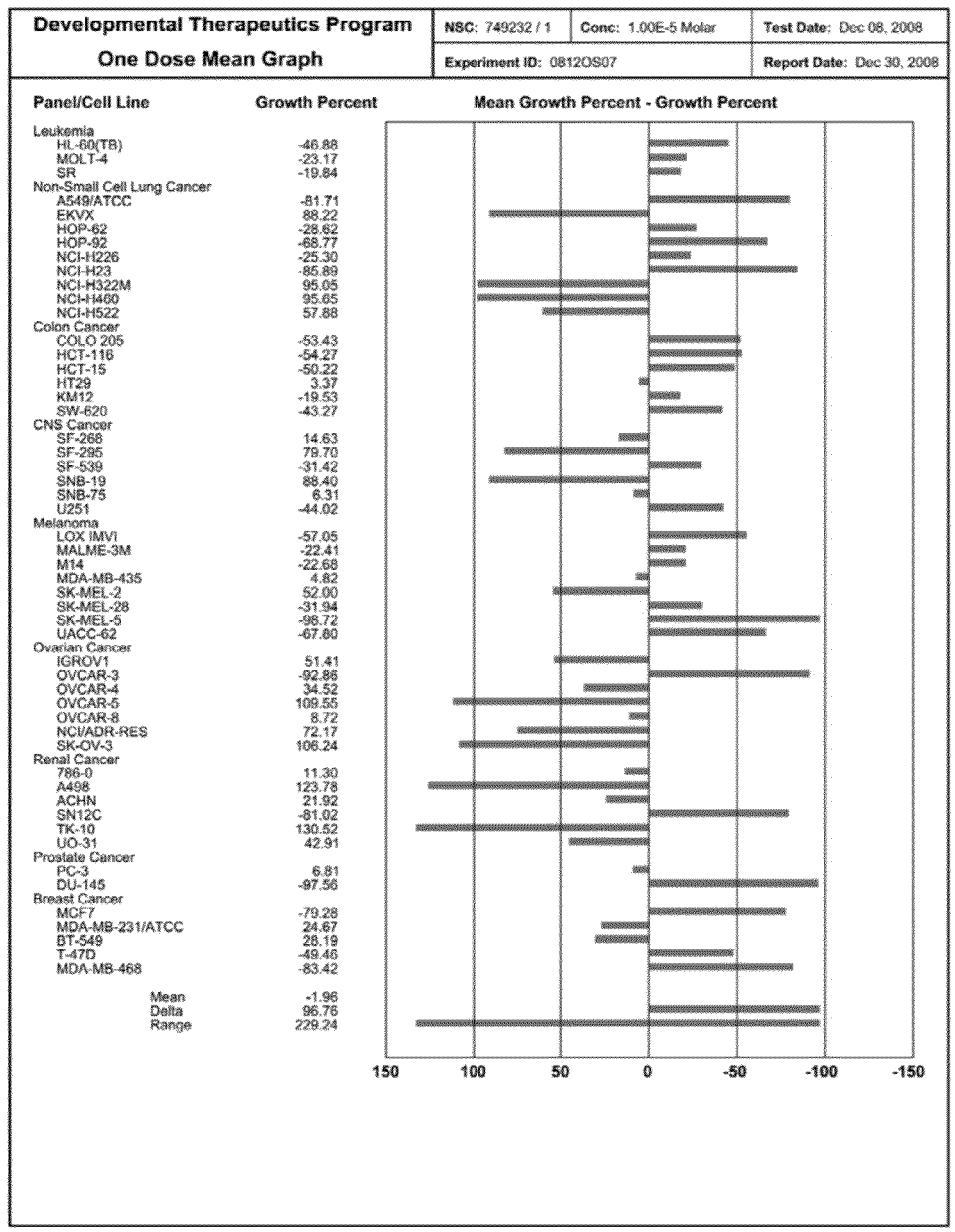
Figure 9:
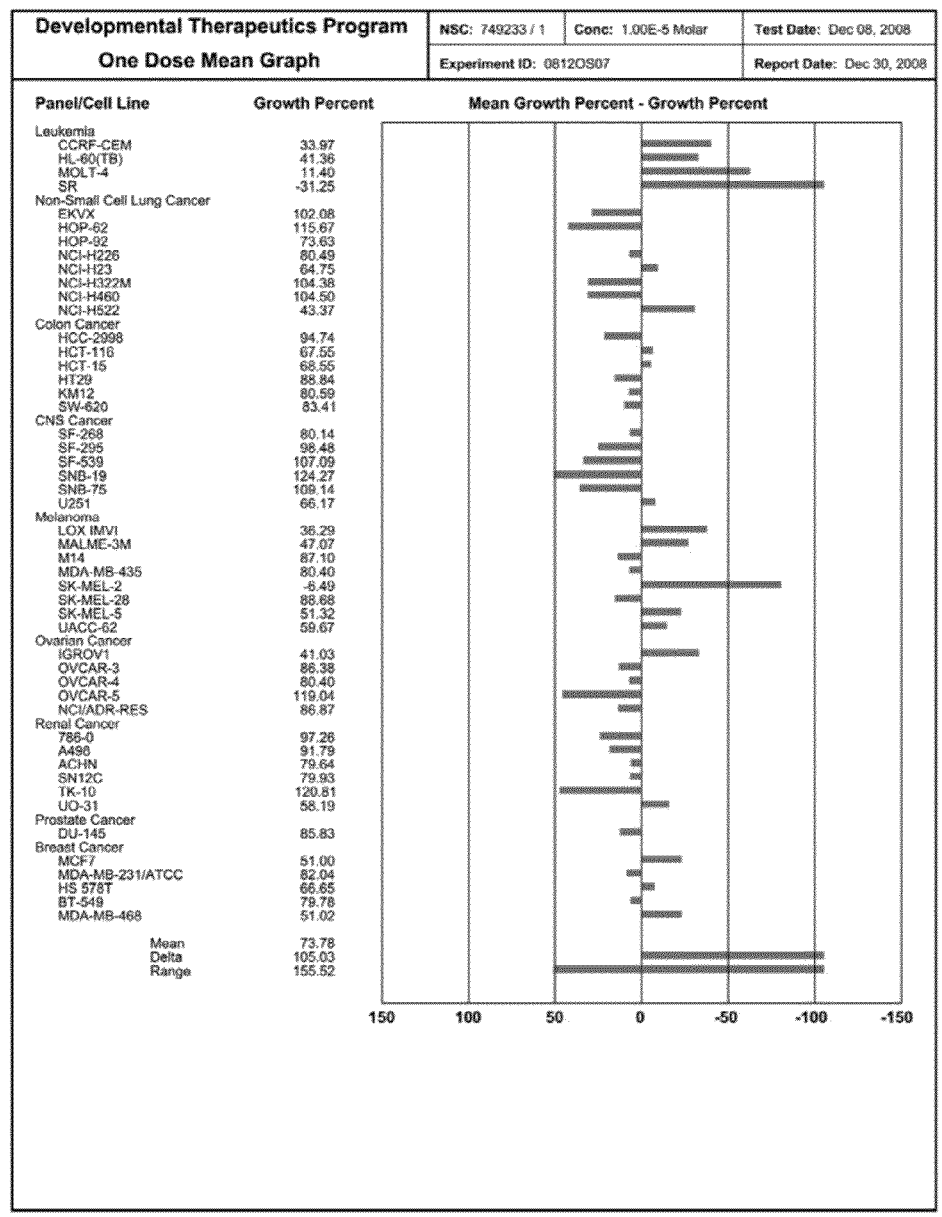
Figure 10:
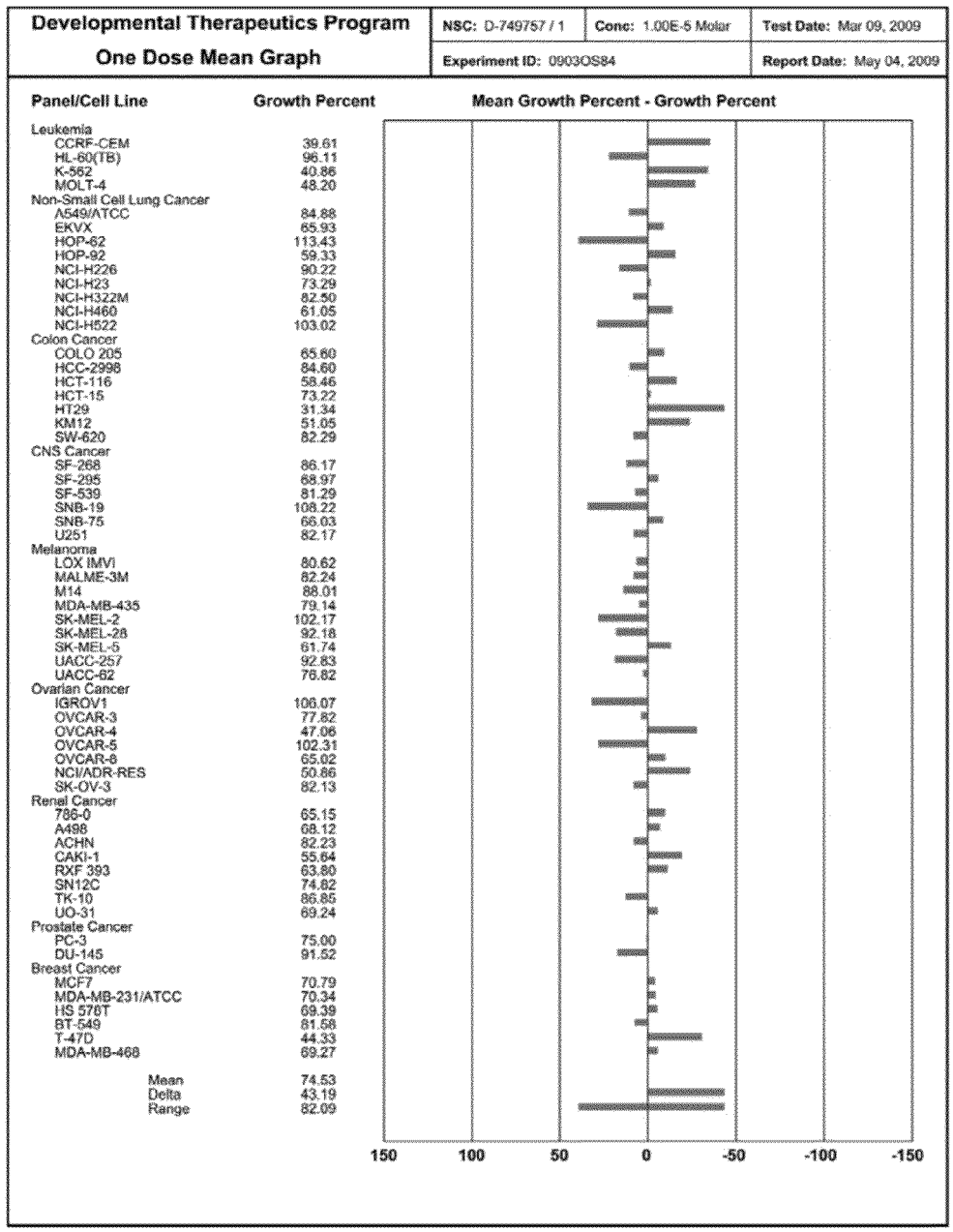
Figure 11:
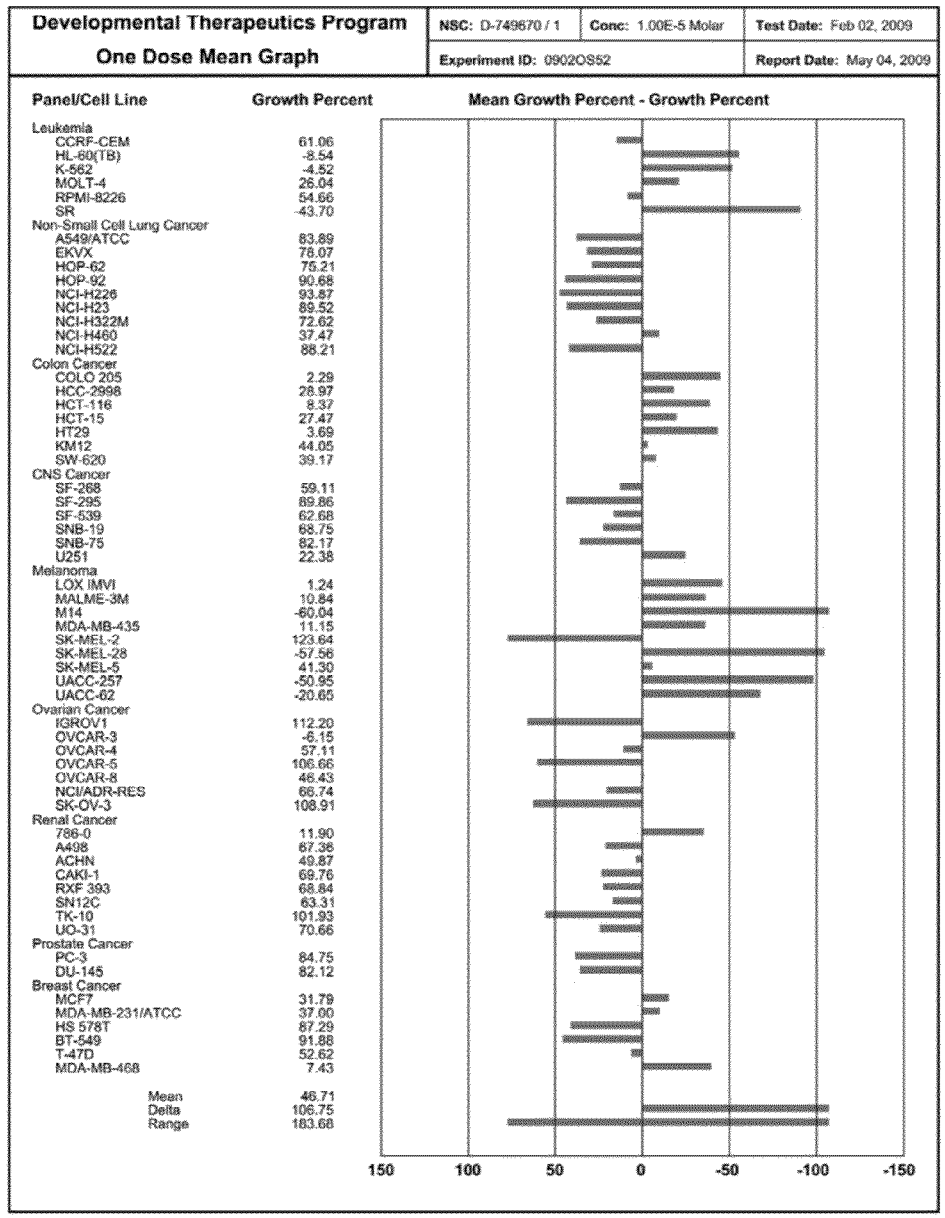

| No | Formula | Compound info. | Code | NSC no. |
|---|---|---|---|---|
| 1 | 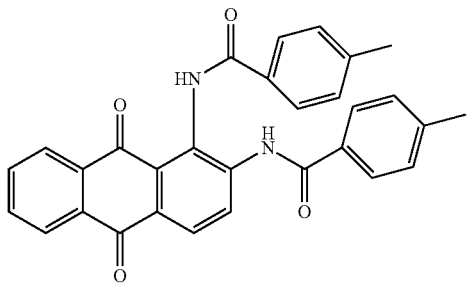 [SMILES: Cc1ccc(C(=O)Nc2ccc3c(c2NC(=O)c2ccc(C)cc2)C(=O)c2ccccc2C3=O)cc1] | 1,2-bis-(4-methylbenzamido)-anthraquinone<br>Chemical Formula: $C_{30}H_{22}N_2O_4$<br>Molecular Weight: 474.5067 | CC-04 | 747246 (FIG. 7) |
| 2 | 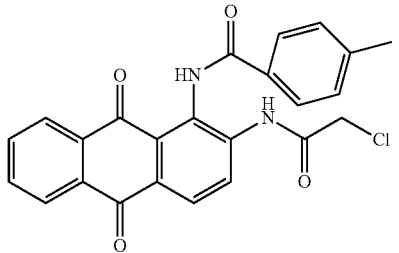 [SMILES: Cc1ccc(C(=O)Nc2c(NC(=O)CCl)ccc3c2C(=O)c2ccccc2C3=O)cc1] | 1-(4-methylbenzamido)-2-(chloroacetamido)-anthraquinone<br>Chemical Formula: $C_{24}H_{17}ClN_2O_4$<br>Molecular Weight: 432.8558 | CC-12 | 749232 (FIG. 8) |
| 3 | 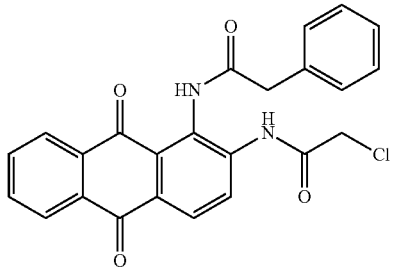 [SMILES: O=C(CCl)Nc1ccc2c(c1NC(=O)Cc1ccccc1)C(=O)c1ccccc1C2=O] | 1-[2-(phenyl)acetylamino]-2-(chloroacetamido)-anthraquinone<br>Chemical Formula: $C_{24}H_{17}ClN_2O_4$<br>Molecular Weight: 432.8558 | CC-23 | 749233 (FIG. 9) |
| 4 | 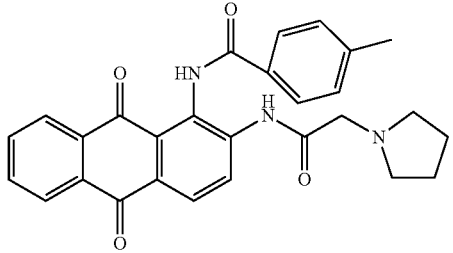 [SMILES: Cc1ccc(C(=O)Nc2c(NC(=O)CN3CCCC3)ccc3c2C(=O)c2ccccc2C3=O)cc1] | 1-(4-methylbenzamido)-2-[2-(tetrahydro-1H-1-pyrrolyl)acetylamino]-anthraquinone<br>Chemical Formula: $C_{28}H_{25}N_3O_4$<br>Molecular Weight: 467.5158 | CC-38 | 749757 (FIG. 10) |
| 5 | 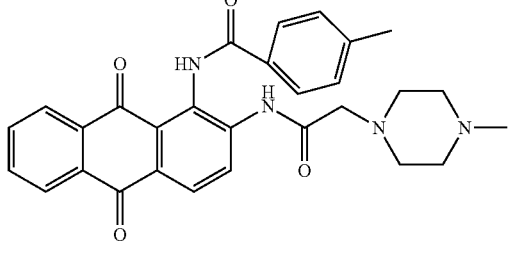 | 1-(4-methylbenzamido)-2-[2-(4-methylpiperazino)acetylamino]-anthraquinone<br>Chemical Formula: $C_{29}H_{28}N_4O_4$<br>Molecular Weight: 496.5570 | CC-43 | 749670 (FIG. 11) |

*The tested concentration of compounds is 1.00E−5 Molar.

TABLE 7

Cytotoxicity of selected compounds in the NCI drug screen

| Panel/Cell Line | Compound/Growth Percent[a] | | | | |
|---|---|---|---|---|---|
| | CC-04 747246 | CC-12 749232 | CC-23 749233 | CC-38 749757 | CC-43 749670 |
| Leukemia | | | | | |
| CCRF-CEM | 79.02 | — | 33.97 | 39.61 | 61.06 |
| HL-60(TB) | 73.11 | −46.88 | 41.36 | 96.11 | −8.54 |
| MOLT-4 | 89.63 | −23.17 | 11.40 | 48.20 | 26.04 |
| SR | 87.69 | −19.84 | −31.25 | — | −43.70 |
| K562 | 107.54 | — | — | 40.86 | −4.52 |
| RPMI-8226 | 101.77 | — | — | — | — |
| Non-Small Cell Lung Cancer | | | | | |
| EKVX | — | 88.22 | 102.08 | 65.93 | 78.07 |
| HOP-62 | 105.23 | −28.62 | 115.67 | 113.43 | 75.21 |
| HOP-92 | 91.21 | −68.77 | 73.63 | 59.33 | 90.68 |
| NCI-H226 | 91.14 | −25.30 | 80.49 | 90.22 | 93.87 |
| NCI-H23 | 90.57 | −85.89 | 64.75 | 73.29 | 89.52 |
| NCI-H322M | 97.74 | 95.05 | 104.38 | 82.50 | 72.60 |
| NCI-H460 | 88.62 | 95.65 | 104.50 | 61.05 | 37.47 |
| NCI-H522 | 72.05 | 57.88 | 43.37 | 103.02 | 88.21 |
| A549/ATCC | 90.46 | −81.71 | — | 84.88 | 83.89 |
| Colon Cancer | | | | | |
| COLO 205 | 108.57 | −53.43 | — | 65.60 | 2.29 |
| HCC-2998 | 84.68 | — | 94.74 | 84.60 | 28.97 |
| HCT-116 | 78.55 | −54.27 | 67.55 | 58.46 | 8.37 |
| HCT-15 | 102.44 | −50.22 | 68.55 | 73.22 | 27.47 |
| HT29 | 99.39 | 3.37 | 88.84 | 31.34 | 3.69 |
| KM12 | 94.21 | −19.53 | 80.59 | 51.05 | 44.05 |
| SW-620 | 93.79 | −43.27 | 83.41 | 82.29 | 39.17 |
| CNS Cancer | | | | | |
| SF-268 | 98.91 | 14.63 | 80.14 | 86.17 | 59.11 |
| SF-295 | 110.81 | 79.70 | 98.48 | 68.97 | 89.86 |
| SF-539 | 97.26 | −31.42 | 107.09 | 81.29 | 62.68 |
| SNB-19 | 103.91 | 88.40 | 124.27 | 108.22 | 68.75 |
| SNB-75 | 102.26 | 6.31 | 109.14 | 66.03 | 82.17 |
| U251 | 91.73 | −44.02 | 66.17 | 82.17 | 22.38 |
| Melanoma | | | | | |
| LOX IMVI | 84.41 | −57.05 | 36.29 | 80.62 | 1.24 |
| MALME-3M | 127.16 | −22.41 | 47.07 | 82.24 | 10.84 |
| M14 | 91.57 | −22.68 | 87.10 | 88.01 | −60.04 |
| MDA-MB-435 | — | 4.82 | 80.40 | 79.14 | 11.15 |
| SK-MEL-2 | 100.65 | 52.00 | −6.49 | 102.17 | 123.64 |
| SK-MEL-28 | 99.46 | −31.94 | 88.68 | 92.18 | −57.56 |
| SK-MEL-5 | 94.04 | −98.72 | 51.32 | 61.74 | 41.30 |
| UACC-62 | 87.50 | −67.80 | 59.67 | 76.82 | −20.65 |
| UACC-257 | 98.46 | — | — | 92.83 | −50.95 |
| Ovarian Cancer | | | | | |
| IGROV1 | 78.71 | 51.41 | 41.03 | 106.07 | 112.20 |
| OVCAR-3 | 97.90 | −92.86 | 86.38 | 77.82 | −6.15 |
| OVCAR-4 | 104.32 | 34.52 | 80.40 | 47.06 | 57.11 |
| OVCAR-5 | 110.18 | 109.55 | 119.04 | 102.31 | 106.66 |
| OVCAR-8 | 85.43 | 8.72 | — | 65.02 | 46.43 |
| NCI/ADR-RES | — | 72.17 | 86.87 | 50.86 | 66.74 |
| SK-OV-3 | 109.62 | 106.24 | — | 82.13 | 108.91 |
| Renal Cancer | | | | | |
| 786-0 | 116.17 | 11.30 | 97.26 | 65.15 | 11.90 |
| A489 | 124.08 | 123.78 | 91.79 | 68.12 | 67.36 |
| ACHN | 112.43 | 21.92 | 79.64 | 82.23 | 49.87 |
| SN12C | 98.59 | −81.02 | 79.93 | 74.82 | 63.31 |
| TK-10 | 124.91 | 130.52 | 120.81 | 86.85 | 101.93 |
| UO-31 | 66.54 | 42.91 | 58.19 | 69.24 | 70.66 |
| CAKI-1 | 94.89 | — | — | 55.64 | 69.76 |
| RXF 393 | 88.25 | — | — | 63.80 | 68.84 |
| Prostate Cancer | | | | | |
| DU145 | 95.93 | −97.56 | 85.83 | 91.52 | 82.12 |
| PC-3 | 82.91 | 6.81 | — | 75.00 | 84.75 |
| Breast Cancer | | | | | |
| MCF7 | 71.71 | −79.28 | 51.00 | 70.79 | 31.79 |
| MDA-MB-231/ATCC | 93.29 | 24.67 | 82.04 | 73.34 | 37.00 |
| HS 578-T | 105.96 | — | 66.65 | 69.39 | 87.29 |
| BT-549 | 95.39 | 28.19 | 79.78 | 81.58 | 91.88 |
| T-47D | 100.00 | −49.46 | — | 44.33 | 52.62 |
| MDA-MB-468 | 104.17 | −83.42 | 51.02 | 69.27 | 7.43 |
| Mean | 96.19 | −1.96 | 73.78 | 74.53 | 46.71 |
| Delta | 29.65 | 96.76 | 105.03 | 43.19 | 106.75 |
| Range | 76.37 | 229.24 | 155.52 | 82.09 | 183.68 |

[a]Data obtained from NCI in vitro 60-cell Drug Screen program at 1.00E−5 Molar concentration.
"—" represent "not test".

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:
1. A 1,2-disubstituted amido-anthraquinone derivative is selected from the group consisting of
 1,2-bis-(4-chlorobutyramido)-anthraquinone,
 1,2-bis-(4-methylbenzamido)-anthraquinone,
 1-(amino)-2-(chloroacetamido)-anthraquinone,
 1-[(2-chloropropanyl)amido]-2-(chloroacetamido)-anthraquinone,
 1-[(3-chloropropanyl)amido]-2-(chloroacetamido)-anthraquinone,
 1-[(4-chlorobutanyl)amido]-2-(chloroacetamido)-anthraquinone,
 1-(benzamido)-2-(chloroacetamido)-anthraquinone,
 1-(2-methylbenzamido)-2-(chloroacetamido)-anthraquinone,
 1-(3-methylbenzamido)-2-(chloroacetamido)-anthraquinone,
 1-(4-methylbenzamido)-2-(chloroacetamido)-anthraquinone,
 1-(2-fluorobenzamido)-2-(chloroacetamido)-anthraquinone,
 1-(3-fluorobenzamido)-2-(chloroacetamido)-anthraquinone,
 1-(4-fluorobenzamido)-2-(chloroacetamido)-anthraquinone,
 1-(2-chlorobenzamido)-2-(chloroacetamido)-anthraquinone,
 1-(3-chlorobenzamido)-2-(chloroacetamido)-anthraquinone,
 1-(4-chlorobenzamido)-2-(chloroacetamido)-anthraquinone,
 1-[2-(trifluoromethyl)benzamido]-2-(chloroacetamido)-anthraquinone,
 1-[3-(trifluoromethyl)benzamido]-2-(chloroacetamido)-anthraquinone,
 1-[4-(trifluoromethyl)benzamido]-2-(chloroacetamido)-anthraquinone,
 5-bis-(trifluoromethyl)benzamido]-2-(chloroacetamido)-anthraquinone,
 1-[2-(phenyl)acetylamino]-2-(chloroacetamido)-anthraquinone,

1-[2-(4-fluorophenyl)acetylamino]-2-(chloroacetamido)-anthraquinone,
1-[(cyclopropanecarbonyl)amino]-2-(chloroacetamido)-anthraquinone,
1-[(cyclohexanecarbonyl)amino]-2-(chloroacetamido)-anthraquinone,
1-[(2-furoyl)amino]-2-(chloroacetamido)-anthraquinone,
1-[(2-thiophenecarbonyl)amino]-2-(chloroacetamido)-anthraquinone,
1-[(5-isoxazolecarbonyl)amino]-2-(chloroacetamido)-anthraquinone,
1-[(2,5-dimethyl-3-furoyl)amino]-2-(chloroacetamido)-anthraquinone,
1-[2-(phenoxy)acetylamino]-2-(chloroacetamido)-anthraquinone,
1-[2-(phenylsulfanyl)acetylamino]-2-(chloroacetamido)-anthraquinone,
1-(benzamido)-2-[2-(4-phenylpiperazino)acetylamino]-anthraquinone,
1-(benzamido)-2-[2-[4-(2-fluorophenyl)piperazino]acetylamino]-anthraquinone,
1-(4-methylbenzamido)-2-[2-(dimethylamino)acetylamino]-anthraquinone,
1-(4-methylbenzamido)-2-[2-[(1,3-dioxolan-2-ylmethyl)(methyl)amino]acetylamino]-anthraquinone,
4-methyl-N-(2-(2-(methyl(2-(pyridin-2-yl)ethyl)amino)acetamido)-9,10-dioxo-9,10-dihydroanthracen-1-yl)benzamide,
1-(4-methylbenzamido)-2-[2-(tetrahydro-1H-1-pyrrolyl)acetylamino]-anthraquinone,
N-(9,10-dioxo-2-(2-(piperidin-1-yl)acetamido)-9,10-dihydroanthracen-1-yl)-4-methylbenzamide,
1-(4-methylbenzamido)-2-[2-(1,4-dioxa-8-azaspiro[4.5]dec-8-yl)acetylamino]-anthraquinone,
1-(4-methylbenzamido)-2-[(2-morpholinoacetyl)amino]-anthraquinone,
1-(4-methylbenzamido)-2-[2-(1,4-thiazinan-4-yl)acetylamino]-anthraquinone,
1-(4-methylbenzamido)-2-[2-(4-methylpiperazino)acetylamino]-anthraquinone,
1-(4-methylbenzamido)-2-[2-[4-(2-hydroxyethyl)piperazino]acetylamino]-anthraquinone,
1-(4-methylbenzamido)-2-[2-(4-phenylpiperazino)acetylamino]-anthraquinone, 1-(4-methylbenzamido)-2-[2-[4-(2-fluorophenyl)piperazino]acetylamino]-anthraquinone,
1-(4-methylbenzamido)-2-[2-[4-(2-cyanophenyl)piperazino]acetylamino]-anthraquinone,
1-(4-methylbenzamido)-2-[2-[4-(2-methoxyphenyl)piperazino]acetylamino]-anthraquinone,
1-(4-methylbenzamido)-2-[2-[4-(2-pyridyl)piperazino]acetylamino]-anthraquinone, and
1-(4-methylbenzamido)-2-[2-[4-(2-pyrimidinyl)piperazino]acetylamino]-anthraquinone.

2. A method for preparing 1,2-disubstituted amido-anthraquinone derivative comprising the following steps:
step 1: dissolving 1,2-diaminoanthraquinone in N,N-dimethylformamide, and to the solution, adding separately (1) pyridine and chloroacetyl chloride; (2) triethylamine and 3-chloropropionyl chloride; or (3) pyridine and 4-chlorobutyryl chloride under stirring; after completion of reaction, lowering the temperature of the mixture, obtaining the precipitate through filtration, and finally, washing said precipitate with ethanol to obtain compound 1,2-bis-(4-chlorobutyramido)-anthraquinone;
step 2: dissolving 1,2-diaminoanthraquinone in tetrahydrofuran, adding thereto successively with pyridine and 4-toluoyl chloride under stirring, stirring this mixture in a oil bath at temperature of 120-130° C.; after completion of reaction, filtering the mixture, concentrating the filtrate by reduced pressure concentrator, extracting the residue with ethyl acetate, drying by $MgSO_4$, then concentrating the extract under reduced pressure, washing the crude product with ethyl acetate/n-hexane, and finally, recrystallizing the crude product in ethanol to obtain compound 1,2-bis-(4-methylbenzamido)-anthraquinone;
step 3: dissolving 1,2-diaminoanthraquinone in N,N-dimethylformamide, adding thereto with chloroacetyl chloride under stirring; after completion of reaction, lowering the temperature of the mixture, filtering to obtain the precipitate, and finally, washing the precipitate with ethanol to obtain compound 1-(amino)-2-(chloroacetamido)-anthraquinone;
step 4: dissolving compound 1-(amino)-2-(chloroacetamido)-anthraquinone in N,N-dimethylformamide, adding thereto successively with (1) pyridine and 2-chloropropionyl chloride, (2) pyridine and 3-chloropropionyl chloride, or (3) pyridine and 4-chlorobutyryl chloride under stirring; after completion of reaction, lowering the temperature of the mixture, filtering to obtain the precipitate, and finally, washing the precipitate with ethanol and recrystallizing to obtain compounds 1-[(2-chloropropanyl)amido]-2-(chloroacetamido)-anthraquinone, 1-[(3-chloropropanyl)amido]-2-(chloroacetamido)-anthraquinone and 1-[(4-chlorobutanyl)amido]-2-(chloroacetamido)-anthraquinone, respectively;
step 5: dissolving compound 1-(amino)-2-(chloroacetamido)-anthraquinone in tetrahydrofuran, adding thereto with pyridine, then adding separately with (1) benzoyl chloride, (2) 2-toluoyl chloride, (3) 3-toluoyl chloride, (4) 4-toluoyl chloride, (5) 2-fluorobenzoyl chloride, (6) 3-fluorobenzoyl chloride, (7) 4-fluorobenzoyl chloride, (8) 2-chlorobenzoyl chloride, (9) 3-chlorobenzoyl chloride, (10) 4-chlorobenzoyl chloride, (11) 2-(trifluoromethyl)benzoyl chloride, (12) 3-(trifluoromethyl)benzoyl chloride, (13) 4-(trifluoromethyl)benzoyl chloride, (14) 2,5-bis-(trifluoromethyl)benzoyl chloride, (15) phenylacetyl chloride, (16) 4-fluorophenylacetyl chloride, (17) cyclopropanecarbonyl chloride, (18) cyclohexanecarbonyl chloride, (19) 2-furoyl chloride, (20) 2-thiophenecarbonyl chloride, (21) isoxazole-5-carbonyl chloride, (22) 2,5-dimethylfuran-3-carbonyl chloride, (23) phenoxyacetyl chloride or (24) (phenylthio)acetyl chloride, under stirring to obtain a mixed solution, reacting this mixed solution by stirring in an oil bath at temperature of 120-130° C.; after completion of reaction, filtering the mixed solution and concentrating the filtrate by reduced pressure concentrator; extracting the residue with ethyl acetate, drying by $MgSO_4$, then concentrating under reduced pressure, washing the crude product with ethyl acetate/n-hexane, and finally, recrystallizing the crude product in ethanol to obtain compounds
1-(benzamido)-2-(chloroacetamido)-anthraquinone,
1-(2-methylbenzamido)-2-(chloroacetamido)-anthraquinone,
1-(3-methylbenzamido)-2-(chloroacetamido)-anthraquinone,
1-(4-methylbenzamido)-2-(chloroacetamido)-anthraquinone,
1-(2-fluorobenzamido)-2-(chloroacetamido)-anthraquinone, 1-(3-fluorobenzamido)-2-(chloroacetamido)-anthraquinone,
1-(4-fluorobenzamido)-2-(chloroacetamido)-anthraquinone,
1-(2-chlorobenzamido)-2-(chloroacetamido)-anthraquinone,
1-(3-chlorobenzamido)-2-(chloroacetamido)-anthraquinone,
1-(4-chlorobenzamido)-2-(chloroacetamido)-anthraquinone,
1-[2-(trifluoromethyl)benzamido]-2-(chloroacetamido)-anthraquinone,
1-[3-(trifluoromethyl)benzamido]-2-(chloroacetamido)-anthraquinone,
1-[4-(trifluoromethyl)benzamido]-2-(chloroacetamido)-anthraquinone,
5-bis-(trifluoromethyl)benzamido]-2-(chloroacetamido)-anthraquinone,
1-[2-(phenyl)acetylamino]-2-(chloroacetamido)-anthraquinone,
1-[2-(4-fluorophenyl)acetylamino]-2-(chloroacetamido)-anthraquinone,
1-[(cyclopropanecarbonyl)amino]-2-(chloroacetamido)-anthraquinone,
1-[(cyclohexanecarbonyl)amino]-2-(chloroacetamido)-anthraquinone,
1-[(2-furoyl)amino]-2-(chloroacetamido)-anthraquinone,
1-[(2-thiophenecarbonyl)amino]-2-(chloroacetamido)-anthraquinone,
1-[(5-isoxazolecarbonyl)amino]-2-(chloroacetamido)-anthraquinone,
1-[(2,5-dimethyl-3-furoyl)amino]-2-(chloroacetamido)-anthraquinone,
1-[2-(phenoxy)acetylamino]-2-(chloroacetamido)-anthraquinone, and
1-[2-(phenylsulfanyl)acetylamino]-2-(chloroacetamido)-anthraquinone, respectively;

step 6: dissolving compound 1-(benzamido)-2-(chloroacetamido)-anthraquinone in tetrahydrofuran, adding thereto at first with N,N-Diisopropylethylamine, then adding separately with (1) N-phenylpiperazine or (2) 1-(2-fluorophenyl)piperazine under stirring, heating this mixed solution under reflux; after completion of reaction, filtering said mixed solution, isolating the crude product from the upper layer of the filtrate, recrystallizing said crude product in ethanol to obtain compounds 1-(benzamido)-2-[2-(4-phenylpiperazino)acetylamino]-anthraquinone and 1-(benzamido)-2-[2-[4-(2-fluorophenyl)piperazino]acetylamino]-anthraquinone, respectively;

step 7: dissolving compound 1-(4-methyl benzamido)-2-(chloroacetamido)-anthraquinone in tetrahydrofuran, adding thereto at first with N,N-Diisopropylethylamine, adding then separately with (1) dimethylamine, (2) 2-methylaminomethyl-1, 3 dioxolane, (3) pyrrolidine, (4) piperidine, (5) 1,4-dioxa-8-azaspiro[4.5]decane, (6) morpholine, (7) thiomorpholine, (8) 2-(piperazin-1-yl)ethanol, (9) N-phenylpiperazine, (10) 1-(2-fluorophenyl)piperazine, (11) 1-(2-cyanophenyl)piperazine, (12) 1-(2-methoxyphenyl)piperazine, (13) 1-(2-pyridyl)piperazine, or (14) 1-(2-pyrimidyl)piperazine under stirring to obtain a mixed solution, heating this mixed solution under reflux; after completion of reaction, filtering the mixed solution, concentrating the filtrate by reduced pressure concentrator, extracting the residue with ethyl acetate, drying by $MgSO_4$, then concentrating under reduced pressure, washing the crude product with ethyl acetate/n-hexane, and finally, recrystallizing the crude product in ethanol to obtain compounds
1-(4-methylbenzamido)-2-[2-(dimethylamino)acetylamino]-anthraquinone,
1-(4-methylbenzamido)-2-[2-[(1,3-dioxolan-2-ylmethyl)(methyl)amino]acetylamino]-anthraquinone,
4-methyl-N-(2-(2-(methyl(2-(pyridin-2-yl)ethyl)amino)acetamido)-9,10-dioxo-9,10-dihydroanthracen-1-yl)benzamide,
1-(4-methylbenzamido)-2-[2-(tetrahydro-1H-1-pyrrolyl)acetylamino]-anthraquinone,
N-(9,10-dioxo-2-(2-(piperidin-1-yl)acetamido)-9,10-dihydroanthracen-1-yl)-4-methylbenzamide, 1-(4-methylbenzamido)-2-[2-(1,4-dioxa-8-azaspiro[4.5]dec-8-yl)acetylamino]-anthraquinone,
1-(4-methylbenzamido)-2-[(2-morpholinoacetyl)amino]-anthraquinone,
1-(4-methylbenzamido)-2-[2-(1,4-thiazinan-4-yl)acetylamino]-anthraquinone,
1-(4-methylbenzamido)-2-[2-(4-methylpiperazino)acetylamino]-anthraquinone,
1-(4-methylbenzamido)-2-[2-(4-(2-hydroxyethyl)piperazino]acetylamino]-anthraquinone,
1-(4-methylbenzamido)-2-[2-(4-phenylpiperazino)acetylamino]-anthraquinone,
1-(4-methylbenzamido)-2-[2-[4-(2-fluorophenyl)piperazino]acetylamino]-anthraqcuinone,
1-(4-methylbenzamido)-2-[2-[4-(2-cyanophenyl)piperazino]acetylamino]-anthraquinone,
1-(4-methylbenzamido)-2-[2-[4-(2-methoxyphenyl)piperazino]acetylamino]-anthraquinone,
1-(4-methylbenzamido)-2-[2-[4-(2-pyridyl)piperazino]acetylamino]-anthraquinone, and
1-(4-methylbenzamido)-2-[2-[4-(2-pyrimidinyl)piperazino]acetylamino]1-anthraquinone, respectively.

3. A pharmaceutical composition for treating cancer, comprising a therapeutically effective amount of compound as recited in claim 1, and a pharmaceutically acceptable excipient.

* * * * *